(12) United States Patent
Klijn et al.

(10) Patent No.: US 11,859,252 B2
(45) Date of Patent: Jan. 2, 2024

(54) DIAGNOSTIC AND THERAPEUTIC METHODS FOR CANCER

(71) Applicant: Genentech, Inc., South San Francisco, CA (US)

(72) Inventors: Christiaan Nicolaas Klijn, San Francisco, CA (US); Shiva Malek, Burlingame, CA (US); Ivana Yen, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 404 days.

(21) Appl. No.: 16/644,902

(22) PCT Filed: Sep. 7, 2018

(86) PCT No.: PCT/US2018/050056
§ 371 (c)(1),
(2) Date: Mar. 5, 2020

(87) PCT Pub. No.: WO2019/051296
PCT Pub. Date: Mar. 14, 2019

(65) Prior Publication Data
US 2020/0190596 A1 Jun. 18, 2020

Related U.S. Application Data

(60) Provisional application No. 62/556,277, filed on Sep. 8, 2017.

(51) Int. Cl.
*C12Q 1/6886* (2018.01)
*A61P 35/00* (2006.01)
*A61K 31/519* (2006.01)
*A61K 31/553* (2006.01)
*A61K 45/06* (2006.01)

(52) U.S. Cl.
CPC .......... *C12Q 1/6886* (2013.01); *A61K 31/519* (2013.01); *A61K 31/553* (2013.01); *A61K 45/06* (2013.01); *A61P 35/00* (2018.01); *C12Q 2600/106* (2013.01); *C12Q 2600/156* (2013.01)

(58) Field of Classification Search
None
See application file for complete search history.

(56) References Cited

U.S. PATENT DOCUMENTS

| 2015/0057275 A1 | 2/2015 | Dias-Santagata et al. |
| 2015/0307947 A1 | 10/2015 | Basu et al. |

FOREIGN PATENT DOCUMENTS

| CN | 103429238 A | 12/2013 |
| CN | 106414738 A | 2/2017 |
| JP | 2015-527874 A | 9/2015 |
| WO | WO-2012/095505 A1 | 7/2012 |
| WO | WO-2013/100632 A1 | 7/2013 |
| WO | WO-2013/178581 A1 | 12/2013 |
| WO | WO-2015/189106 A1 | 12/2015 |
| WO | WO-2015/200377 A1 | 12/2015 |
| WO | WO-2017/121877 A1 | 7/2017 |
| WO | WO-2019/051296 A1 | 3/2019 |

OTHER PUBLICATIONS

Adjei et al. "A Phase I Study of the Safety, Pharmacokinetics, and Pharmacodynamics of Combination Therapy with Refametinib plus Sorafenib in Patients with Advanced Cancer," Clin Cancer Res; 22(10) May 15, 2016. (Year: 2016).*
Peng et al. Cancer Cell 28, 384-398, Sep. 14, 2015 (Year: 2015).*
Inoue et al. Oncology Reports 28: 1579-1584, 2012. (Year: 2012).*
Hatzivvassiliou et al. Nature 502 1-5 published online Aug. 2013 (Year: 2013).*
Bae et al. Cancer Res (2015) 75 (15_Supplement): 2606. (Year: 2015).*
Whittaker et al. Mol Cancer Ther; 14(12) Dec. 2015 (Year: 2015).*
Atefi et al., "Combination of pan-RAF and MEK Inhibitors in NRAS Mutant Melanoma," Mol Cancer. 14(1):27 (2015) (12 pages).
Jin et al., "Synergistic Action of a RAF Inhibitor and a Dual PI3K/mTOR Inhibitor in Thyroid Cancer," Clin Cancer Res. 17(20):6482-9 (2011).
Little et al., "Mechanisms of Acquired Resistance to ERK1/2 Pathway Inhibitors," Oncogene. 32(10):1207-15 (2013).
McCubrey et al., "Ras/Raf/MEK/ERK and PI3K/PTEN/Akt/mTOR Cascade Inhibitors: How Mutations Can Result in Therapy Resistance and How to Overcome Resistance," Oncotarget. 3(10):1068-111 (2012).
Nakamura et al., "Antitumor Activity of the Selective pan-RAF Inhibitor TAK-632 in BRAF Inhibitor-Resistant Melanoma," Cancer Res. 73(23):7043-55 (2013).
Whittaker et al., "Combined Pan-RAF and MEK Inhibition Overcomes Multiple Resistance Mechanisms to Selective RAF Inhibitors," Mol Cancer Ther. 14(12): 2700-11 (2015).
International Preliminary Report on Patentability for International Application No. PCT/US2018/050056, dated Mar. 10, 2020 (9 pages).

(Continued)

*Primary Examiner* — Jeffrey S Lundgren
*Assistant Examiner* — Michael J Schmitt
(74) *Attorney, Agent, or Firm* — Clark & Elbing LLP; Thomas J. Takara

(57) ABSTRACT

The present invention provides diagnostic and therapeutic methods and compositions for cancer. The invention provides methods of determining whether an individual having a cancer is likely to respond to treatment comprising a pan-RAF dimer inhibitor and a MEK or PI3K inhibitor, methods of predicting responsiveness of an individual having a cancer to treatment comprising a pan-RAF dimer inhibitor and a MEK or PI3K inhibitor, methods of selecting a therapy for an individual having a cancer, and methods of treating an individual having cancer based on the presence of a biomarker of the invention (e.g., a KRAS activating mutation, e.g., a KRAS-G13D mutation, or an NRAS activating mutation).

5 Claims, 46 Drawing Sheets

Specification includes a Sequence Listing.

(56) References Cited

OTHER PUBLICATIONS

International Search Report and Written Opinion for International Application No. PCT/US2018/050056, dated Dec. 12, 2018 (19 pages).

Notice of Reasons for Rejection for Japanese Patent Application No. 2020-512855, dated Aug. 9, 2022 (8 pages).

Hunter et al., "Biochemical and Structural Analysis of Common Cancer-Associated KRAS Mutations," Mol Cancer. 13(9): 1325-35 (2015).

Tejpar et al., "Association of KRAS G13D Tumor Mutations With Outcome in Patients With Metastatic Colorectal Cancer Treated With First-Line Chemotherapy With or Without Cetuximab," Journal of Clinical Oncology. 30(29):3570-7 (2012).

* cited by examiner

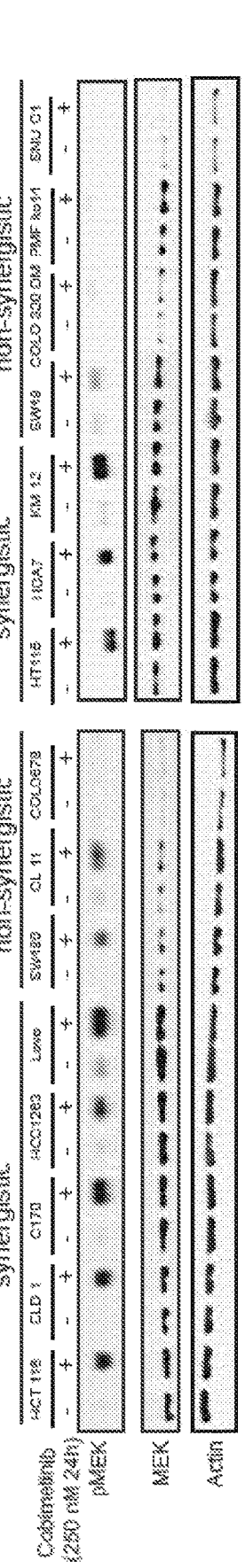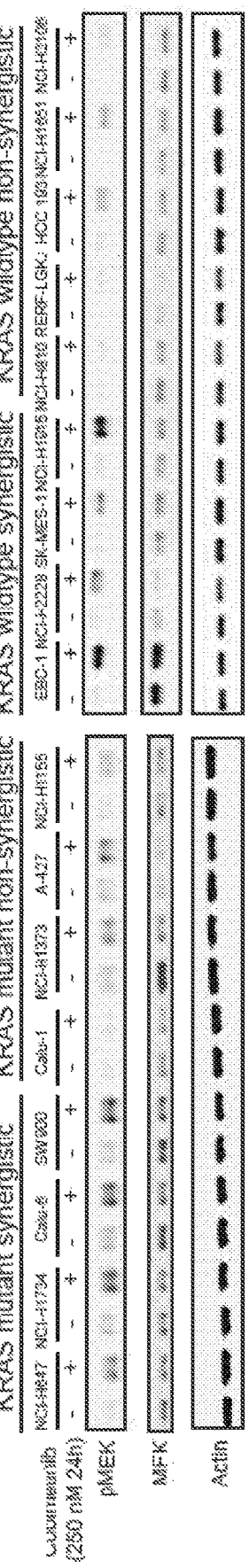

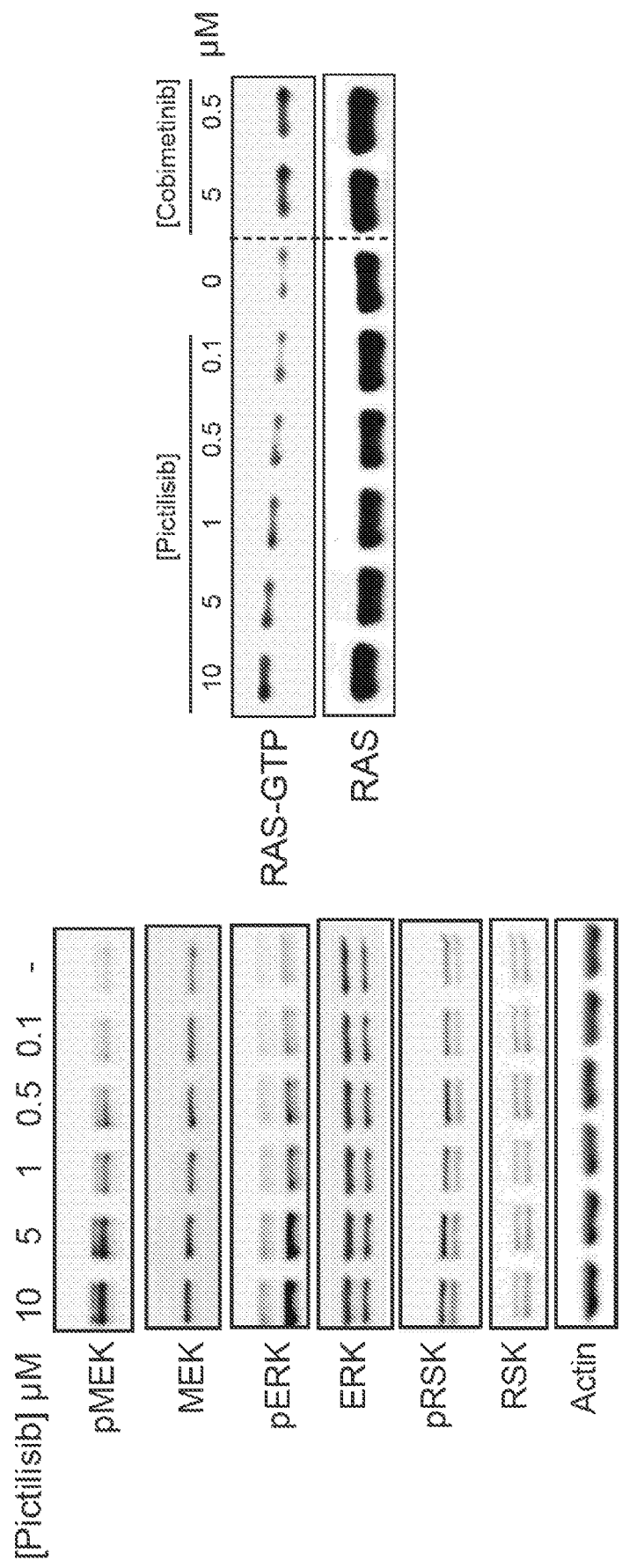

SEQUENCE LISTING

<160> NUMBER OF SEQ ID NOS: 6

<210> SEQ ID NO 1
<211> LENGTH: 65
<212> TYPE: DNA

```
<213> ORGANISM: Artificial Sequence
<220> FEATURE:
<223> OTHER INFORMATION: Synthetic Construct

<400> SEQUENCE: 1 gatcccccctt acgctgagta cttcgattca agagatcgaa gtactcagcg taagtttttt    60
ggaaa                                                                 65

<210> SEQ ID NO 2
<211> LENGTH: 65
<212> TYPE: DNA
<213> ORGANISM: Artificial Sequence
<220> FEATURE:
<223> OTHER INFORMATION: Synthetic Construct

<400> SEQUENCE: 2
agcttttcca aaaacttac gctgagtact tcgatctctt gaatcgaagt actcagcgta      60
agggg                                                                 65

<210> SEQ ID NO 3
<211> LENGTH: 65
<212> TYPE: DNA
<213> ORGANISM: Artificial Sequence
<220> FEATURE:
<223> OTHER INFORMATION: Synthetic Construct

<400> SEQUENCE: 3
gatccccgac atgaaatcca acaatattca agagatattg ttggatttca tgtcttttt     60 ggaaa                                                                 65

<210> SEQ ID NO 4
<211> LENGTH: 65
<212> TYPE: DNA
<213> ORGANISM: Artificial Sequence
<220> FEATURE:
<223> OTHER INFORMATION: Synthetic Construct

<400> SEQUENCE: 4
agcttttcca aaaagacat gaaatccaac aatatctctt gaatattgtt ggatttcatg     60
tcggg                                                                 65

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
tcctgcgtct agaggttccc a                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
taggagtaga catccgactg g                                               21
```

DIAGNOSTIC AND THERAPEUTIC METHODS FOR CANCER

SEQUENCE LISTING

The instant application contains a Sequence Listing which has been submitted electronically in ASCII format and is hereby incorporated by reference in its entirety. Said ASCII copy, created on Aug. 9, 2018 is named 50474-171-WO2_Sequence_Listing_8.09.18_ST25 and is 1,738 bytes in size.

FIELD OF THE INVENTION

The present invention is directed to diagnostic and therapeutic methods for the treatment of proliferative cell disorders (e.g., cancers) using a pan-RAF dimer inhibitor and a MEK or PI3K inhibitor. Also provided are related kits and compositions.

BACKGROUND

Cancer remains one of the most deadly threats to human health. Certain cancers can metastasize and grow rapidly in an uncontrolled manner, making timely detection and treatment extremely difficult. In the U.S., cancer affects nearly 1.3 million new patients each year and is the second leading cause of death after heart disease, accounting for approximately one in four deaths. The mitogen-activated protein kinase (MAPK) signaling pathway is activated in more than 30% of human cancers, most commonly in the MEK/ERK arm of the pathway via oncogenic mutations.

Thus, there remains a need to develop improved alternative methods for diagnosing and treating patient populations having MAPK-dysregulated tumors that might be best suited for treatment targeting the MAPK signaling pathway.

SUMMARY OF THE INVENTION

The present invention provides diagnostic and therapeutic methods, kits, and compositions for the treatment of proliferative cell disorders (e.g., cancers).

In a first aspect, the invention features a method of identifying an individual having a cancer who may benefit from a treatment including a pan-RAF dimer inhibitor and a MEK inhibitor, the method including screening a sample from the individual for a KRAS-G13D mutation, wherein the presence of a KRAS-G13D mutation in the sample identifies the individual as one who may benefit from treatment including a pan-RAF dimer inhibitor and a MEK inhibitor.

In a second aspect, the invention features a method for selecting a treatment for an individual having a cancer, the method including screening a sample from the individual for a KRAS-G13D mutation, wherein the presence of a KRAS-G13D mutation in the sample identifies the individual as one who may benefit from a treatment including a pan-RAF dimer inhibitor and a MEK inhibitor.

In some embodiments of the first aspect or the second aspect, the individual has a KRAS-G13D mutation and the method further includes administering to the individual a therapeutically effective amount of a pan-RAF dimer inhibitor and a MEK inhibitor.

In a third aspect, the invention features a method of treating an individual having a cancer, the method including: (a) screening a sample from the individual for a KRAS-G13D mutation, wherein the individual has been determined to have a KRAS-G13D mutation, and (b) administering a therapeutically effective amount of a pan-RAF dimer inhibitor and a MEK inhibitor to the individual based on the presence of a KRAS-G13D mutation determined in step (a).

In a fourth aspect, the invention features a method of treating an individual having a cancer, the method including administering to the individual a therapeutically effective amount of a pan-RAF dimer inhibitor and a MEK inhibitor, wherein prior to treatment a sample from the individual has been screened for a KRAS-G13D mutation and the presence of a KRAS-G13D mutation in the sample has been determined.

In some embodiments of any one of the preceding aspects, the screening includes amplifying and sequencing all or a portion of the KRAS gene. In some embodiments, the portion of the KRAS gene is exon 2 of the KRAS gene. In some embodiments, a KRAS c.38G>A nucleotide substitution mutation at codon 13 of exon 2 of the KRAS gene is indicative of a KRAS-G13D mutation.

In a fifth aspect, the invention features composition comprising a pan-RAF dimer inhibitor and a MEK inhibitor for use in the therapeutic treatment of a cancer characterized by a KRAS-G13D mutation.

In a sixth aspect, the invention features the use of a composition comprising a pan-RAF dimer inhibitor and a MEK inhibitor for the preparation of a medicament for the therapeutic treatment of a cancer characterized by a KRAS-G13D mutation.

In a seventh aspect, the invention features a method of identifying an individual having a cancer who may benefit from a treatment including a pan-RAF dimer inhibitor and a MEK inhibitor, the method including screening a sample from the individual for an NRAS activating mutation, wherein the presence of an NRAS activating mutation in the sample identifies the individual as one who may benefit from treatment including a pan-RAF dimer inhibitor and a MEK inhibitor.

In an eighth aspect, the invention features a method for selecting a treatment for an individual having a cancer, the method including screening a sample from the individual for an NRAS activating mutation, wherein the presence of an NRAS activating mutation in the sample identifies the individual as one who may benefit from a treatment including a pan-RAF dimer inhibitor and a MEK inhibitor.

In some embodiments of the seventh aspect or the eighth aspect, the individual has an NRAS activating mutation and the method further includes administering to the individual a therapeutically effective amount of a pan-RAF dimer inhibitor and a MEK inhibitor.

In a ninth aspect, the invention features a method of treating an individual having a cancer, the method including: (a) screening a sample from the individual for an NRAS activating mutation, wherein the individual has been determined to have an NRAS activating mutation, and (b) administering a therapeutically effective amount of a pan-RAF dimer inhibitor and a MEK inhibitor to the individual based on the presence of an NRAS activating mutation determined in step (a).

In a tenth aspect, the invention features a method of treating an individual having a cancer, the method including administering to the individual a therapeutically effective amount of a pan-RAF dimer inhibitor and a MEK inhibitor, wherein prior to treatment a sample from the individual has been screened for an NRAS activating mutation and the presence of an NRAS activating mutation in the sample has been determined.

In some embodiments of any one of the seventh, eighth, ninth, and tenth aspects, the screening includes amplifying and sequencing all or a portion of the NRAS gene.

In some embodiments of any one of the first, second, third, fourth, seventh, eighth, ninth, and tenth aspects, the MEK inhibitor is a small molecule inhibitor. In some embodiments, the small molecule inhibitor is selected from the group consisting of cobimetinib (GDC-0973), selumetinib (AZD6244), pimasertib (AS-703026), PD0325901, refametinib (BAY86-9766), binimetinib (MEK162), BI-847325, trametinib, GDC-0623, G-573, and CH5126766 (RO5126766), or a pharmaceutically acceptable salt thereof. In some embodiments, the small molecule inhibitor is cobimetinib (GDC-0973), selumetinib (AZD6244), pimasertib (AS-703026), PD0325901, refametinib (BAY86-9766), or binimetinib (MEK162), or a pharmaceutically acceptable salt thereof. In some embodiments, the small molecule inhibitor is cobimetinib (GDC-0973), or a pharmaceutically acceptable salt thereof.

In a eleventh aspect, the invention features a method of treating an individual having a cancer including a KRAS activating mutation, the method including administering to the individual a therapeutically effective amount of a pan-RAF dimer inhibitor and a PI3K inhibitor. In some embodiments, the PI3K inhibitor is a small molecule inhibitor. In some embodiments, the small molecule inhibitor is selected from the group consisting of pictilisib (GDC-0941), taselisib (GDC-0032), and alpelisib (BYL719), or a pharmaceutically acceptable salt thereof. In some embodiments, the PI3K inhibitor is a pan-PI3K inhibitor. In some embodiments, the pan-PI3K inhibitor is pictilisib (GDC-0941) or taselisib (GDC-0032), or a pharmaceutically acceptable salt thereof. In some embodiments, the individual does not have a BRAF activating mutation.

In some embodiments of any one of the first, second, third, fourth, seventh, eighth, ninth, tenth, and eleventh aspects, the method further includes administering to the individual an additional therapeutic agent. In some embodiments, the additional therapeutic agent is selected from the group consisting of an immunotherapy agent, a cytotoxic agent, a growth inhibitory agent, a radiation therapy agent, and an anti-angiogenic agent.

In a twelfth aspect, the invention features a composition comprising a pan-RAF dimer inhibitor and a PI3K inhibitor for use in the therapeutic treatment of a cancer characterized by a KRAS activating mutation.

In a thirteenth aspect, the invention features the use of a composition comprising a pan-RAF dimer inhibitor and a PI3K inhibitor for the preparation of a medicament for the therapeutic treatment of a cancer characterized by a KRAS activating mutation.

In a fourteenth aspect, the invention features a composition including a pan-RAF dimer inhibitor and a pan-PI3K inhibitor. In some embodiments, the pan-PI3K inhibitor is pictilisib (GDC-0941) or taselisib (GDC-0032), or a pharmaceutically acceptable salt thereof. In some embodiments, the pan-RAF dimer inhibitor is selected from the group consisting of HM95573, LY-3009120, AZ-628, LXH-254, MLN2480, BeiGene-283, RXDX-105, BAL3833, regorafenib, and sorafenib, or a pharmaceutically acceptable salt thereof. In some embodiments, the composition comprises a combination selected from the group consisting of HM95573 and pictilisib (GDC-0941), LY-3009120 and pictilisib (GDC-0941), AZ-628 and pictilisib (GDC-0941), LXH-254 and pictilisib (GDC-0941), MLN2480 and pictilisib (GDC-0941), BeiGene-283 and pictilisib (GDC-0941), RXDX-105 and pictilisib (GDC-0941), BAL3833 and pictilisib (GDC-0941), regorafenib and pictilisib (GDC-0941), sorafenib and pictilisib (GDC-0941), HM95573 and taselisib (GDC-0032), LY-3009120 and taselisib (GDC-0032), AZ-628 and taselisib (GDC-0032), LXH-254 and taselisib (GDC-0032), MLN2480 and taselisib (GDC-0032), BeiGene-283 and taselisib (GDC-0032), RXDX-105 and taselisib (GDC-0032), BAL3833 and taselisib (GDC-0032), regorafenib and taselisib (GDC-0032), and sorafenib and taselisib (GDC-0032), or a pharmaceutically acceptable salt thereof. In some embodiments, the composition is for use in the therapeutic treatment of a cancer. In some embodiments, the cancer is selected from the group consisting of a colorectal cancer, an ovarian cancer, a lung cancer, a pancreatic cancer, a skin cancer, a kidney cancer, a bladder cancer, a breast cancer, a gastric carcinoma, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, a mycosis fungoides, a Merkel cell cancer, and a hematologic malignancy.

In a fifteenth aspect, the invention features a pharmaceutical composition comprising a composition according to the sixteenth aspect.

In a sixteenth aspect, the invention features the use of a composition according to the sixteenth aspect for the preparation of a medicament for the therapeutic treatment of a cancer. In some embodiments, the cancer is selected from the group consisting of a colorectal cancer, an ovarian cancer, a lung cancer, a pancreatic cancer, a skin cancer, a kidney cancer, a bladder cancer, a breast cancer, a gastric carcinoma, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, a mycosis fungoides, a Merkel cell cancer, and a hematologic malignancy.

In a seventeenth aspect, the invention features a kit for identifying an individual having a cancer who may benefit from a treatment including a pan-RAF dimer inhibitor and a MEK inhibitor, the kit including: (a) reagents for determining the presence of a KRAS-G13D mutation in a sample from the individual, and, optionally, (b) instructions for using the reagents to identify an individual having a cancer who may benefit from a treatment including a pan-RAF dimer inhibitor and a MEK inhibitor. In some embodiments, the reagents include a first oligonucleotide and a second oligonucleotide for use in amplifying all or a portion of the KRAS gene.

In an eighteenth aspect, the invention features a kit for identifying an individual having a cancer who may benefit from a treatment including a pan-RAF dimer inhibitor and a MEK inhibitor, the kit including: (a) reagents for determining the presence of an NRAS activating mutation in a sample from the individual, and, optionally, (b) instructions for using the reagents to identify an individual having a cancer who may benefit from a treatment including a pan-RAF dimer inhibitor and a MEK inhibitor. In some embodiments, the reagents include a first oligonucleotide and a second oligonucleotide for use in amplifying all or a portion of the NRAS gene.

In some embodiments of the seventeenth aspect or the eighteenth aspect, the MEK inhibitor is a small molecule inhibitor. In some embodiments, the small molecule inhibitor is selected from the group consisting of cobimetinib (GDC-0973), selumetinib (AZD6244), pimasertib (AS-703026), PD0325901, refametinib (BAY86-9766), binimetinib (MEK162), BI-847325, trametinib, GDC-0623, G-573, and CH5126766 (RO5126766), or a pharmaceutically acceptable salt thereof. In some embodiments, the small molecule inhibitor is cobimetinib (GDC-0973), selumetinib (AZD6244), pimasertib (AS-703026), PD0325901, refametinib (BAY86-9766), or binimetinib (MEK162), or a pharmaceutically acceptable salt thereof. In some embodiments, the small molecule inhibitor is cobimetinib (GDC-0973), or a pharmaceutically acceptable salt thereof.

In a nineteenth aspect, the invention features a kit for identifying an individual having a cancer who may benefit from a treatment including a pan-RAF dimer inhibitor and a PI3K inhibitor, the kit including: (a) reagents for determining the presence of an KRAS activating mutation in a sample from the individual, and, optionally, (b) instructions for using the reagents to identify an individual having a cancer who may benefit from a treatment including a pan-RAF dimer inhibitor and a PI3K inhibitor. In some embodiments, the reagents include a first oligonucleotide and a second oligonucleotide for use in amplifying all or a portion of the KRAS gene. In some embodiments, the PI3K inhibitor is a small molecule inhibitor. In some embodiments, the small molecule inhibitor is selected from the group consisting of pictilisib (GDC-0941), taselisib (GDC-0032), and alpelisib (BYL719), or a pharmaceutically acceptable salt thereof. In some embodiments, the PI3K inhibitor is a pan-PI3K inhibitor. In some embodiments, the pan-PI3K inhibitor is pictilisib (GDC-0941) or taselisib (GDC-0032), or a pharmaceutically acceptable salt thereof. In some embodiments, the individual does not have a BRAF activating mutation.

In some embodiments of any one of the preceding aspects, the pan-RAF dimer inhibitor is selected from the group consisting of HM95573, LY-3009120, AZ-628, LXH-254, MLN2480, BeiGene-283, RXDX-105, BAL3833, regorafenib, and sorafenib, or a pharmaceutically acceptable salt thereof.

In some embodiments of any one of the preceding aspects, the sample is a tissue sample, a cell sample, a whole blood sample, a plasma sample, a serum sample, or a combination thereof. In some embodiments, the sample is a tissue sample. In some embodiments, the tissue sample is a tumor tissue sample. In some embodiments, the tumor tissue sample is a formalin-fixed and paraffin-embedded (FFPE) sample, an archival sample, a fresh sample, or a frozen sample.

In some embodiments of any one of the preceding aspects, the cancer is selected from the group consisting of a colorectal cancer, an ovarian cancer, a lung cancer, a pancreatic cancer, a skin cancer, a kidney cancer, a bladder cancer, a breast cancer, a gastric carcinoma, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, a mycosis fungoides, a Merkel cell cancer, or a hematologic malignancy. In some embodiments, the cancer is a colorectal cancer. In some embodiments, the cancer is an ovarian cancer. In some embodiments, the cancer is a lung cancer. In some embodiments, the cancer is a pancreatic cancer. In some embodiments, the cancer is a skin cancer.

In some embodiments of any one of the preceding aspects, the individual is a human.

BRIEF DESCRIPTION OF THE DRAWINGS

FIG. 4B is a series of immunoblots showing MEK inhibition by cobimetinib in synergistic and non-synergistic KRAS mutant and wild-type colon cancer cell lines. The indicated cancer cell lines were treated with either DMSO or 250 nM cobimetinib for 24 hours and protein lysates were analyzed by Western blotting for phospho- or total MEK, relative to control (actin).

FIG. 4C is a series of immunoblots showing MEK inhibition by cobimetinib in synergistic and non-synergistic KRAS mutant and wild-type lung cancer cell lines. The indicated cancer cell lines were treated with either DMSO or 250 nM cobimetinib for 24 hours and protein lysates were analyzed by Western blotting for phospho- or total MEK, relative to control (actin).

FIG. 7D is an immunoblot showing that PI3K inhibition results in a dose-dependent induction of pMEK. A549 cells were treated with the indicated concentrations of pictilisib for 24 hours were then processed for Western blot analysis for phospho- and total levels of MEK, ERK, and RSK, relative to control (actin).

FIG. 7E is an immunoblot showing that PI3K inhibition results in a dose-dependent induction of RAS-GTP levels. A549 cells were treated with the indicated concentrations of pictilisib and cobimetinib for 24 hours and active RAS was immunoprecipitated utilizing the RAF1-RBD.

DETAILED DESCRIPTION OF THE INVENTION

I. Introduction

Figure 1A:
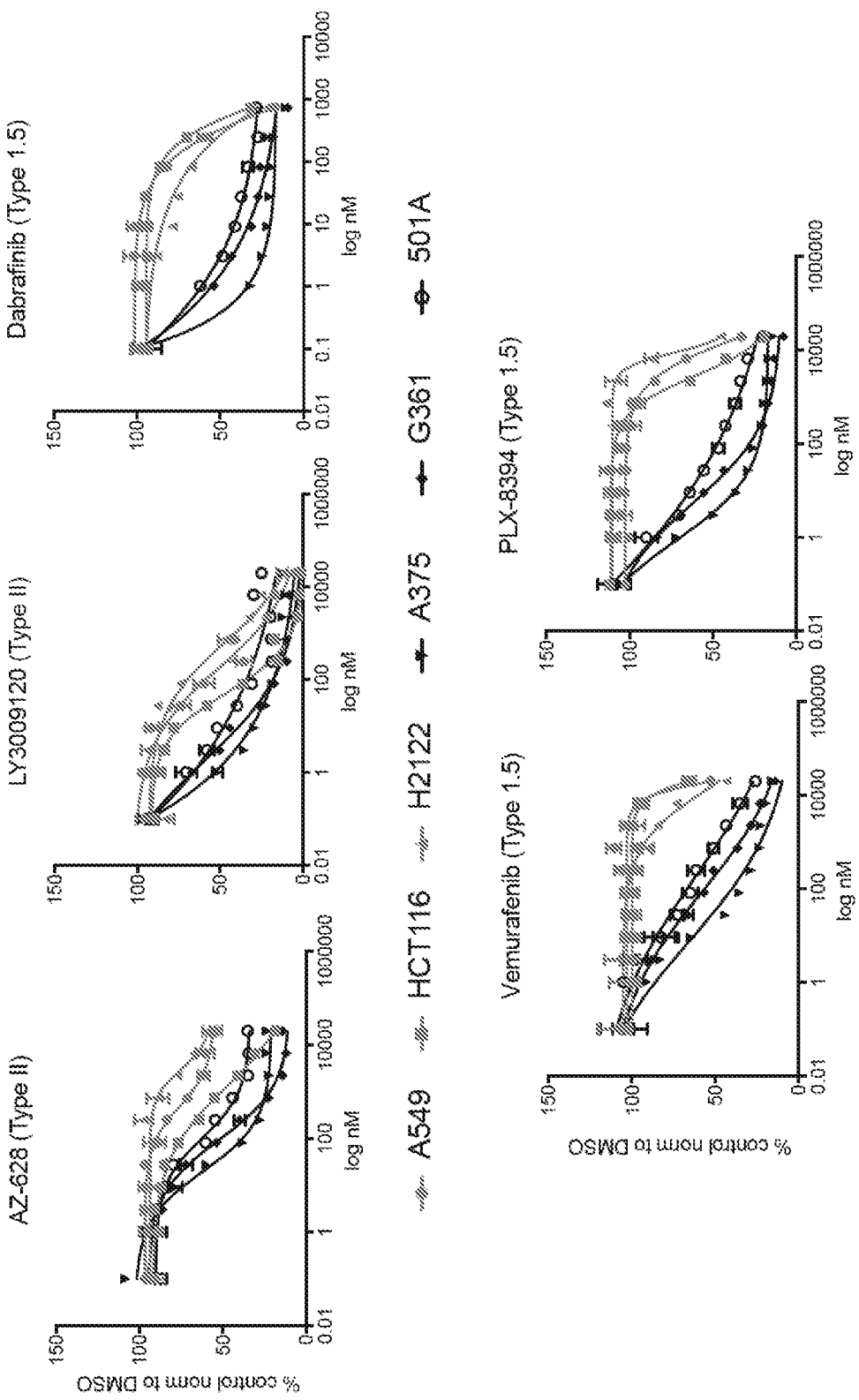
FIG. 1A is a series of graphs showing profiling of KRAS mutant cell lines (red) and BRAF$^{V600E}$ cell lines (black) against the indicated RAF inhibitors in a 3-day CELLTITER-GLO® viability assay. Curves were determined with a four-parameter sigmoidal curve fit.

The present invention provides diagnostic methods, therapeutic methods, and compositions for the treatment of proliferative cell disorders (e.g., cancer (e.g., colorectal cancer, ovarian cancer, lung cancer, pancreatic cancer, and skin cancer (e.g., melanoma))). The invention is based, at least in part, on the discovery that MEK and PI3K inhibitors exhibit synergistic activity with pan-RAF dimer inhibitors in cancers harboring an NRAS activating mutation or a KRAS activating mutation, particularly a KRAS-G13D mutation, through a RAS-GTP-dependent mechanism. Accordingly, the KRAS-G13D and NRAS activating mutations can be used as biomarkers (e.g., predictive biomarkers) in methods of identifying individuals having a cancer who may benefit from treatment including a pan-RAF dimer inhibitor and a MEK or PI3K inhibitor; selecting a treatment for an individual having cancer that includes a pan-RAF dimer inhibitor and a MEK or PI3K inhibitor, as well as treating an individual having a cancer with a therapy including a pan-RAF dimer inhibitor and a MEK or PI3K inhibitor.

II. Definitions

It is to be understood that aspects and embodiments of the invention described herein include "comprising," "consisting," and "consisting essentially of" aspects and embodiments. As used herein, the singular form "a," "an," and "the" includes plural references unless indicated otherwise. The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X."

The term "MAPK signaling pathway" refers to the mitogen-activated protein kinase signaling pathway (e.g., the RAS/RAF/MEK/ERK signaling pathway) and encompasses a family of conserved serine/threonine protein kinases (e.g., the mitogen-activated protein kinases (MAPKs)). Abnormal regulation of the MAPK pathway contributes to uncontrolled proliferation, invasion, metastases, angiogenesis, and diminished apoptosis. The RAS family of GTPases includes KRAS, HRAS, and NRAS. The RAF family of serine/threonine protein kinases includes ARAF, BRAF, and CRAF (RAF1). Exemplary MAPKs include the extracellular signal-regulated kinase 1 and 2 (i.e., ERK1 and ERK2), the c-Jun N-terminal kinases 1-3 (i.e., JNK1, JNK2, and JNK3), the p38 isoforms (i.e., p38α, p38β, p38γ, and p38δ), and Erk5. Additional MAPKs include Nemo-like kinase (NLK), Erk3/4 (i.e., ERK3 and ERK4), and Erk7/8 (i.e., ERK7 and ERK8).

The term "MAPK signaling inhibitor" or "MAPK pathway signaling inhibitor" refers to a molecule that decreases, blocks, inhibits, abrogates, or interferes with signal transduction through the MAPK pathway (e.g., the RAS/RAF/MEK/ERK pathway). In some embodiments, a MAPK signaling inhibitor may inhibit the activity of one or more proteins involved in the activation of MAPK signaling. In some embodiments, a MAPK signaling inhibitor may increase the activity of one or more proteins involved in the inhibition of MAPK signaling. MAPK signaling inhibitors include, but are not limited to, MEK inhibitors (e.g., MEK1 inhibitors, MEK2 inhibitors, and inhibitors of both MEK1 and MEK2), RAF inhibitors (e.g., ARAF inhibitors, BRAF inhibitors, CRAF inhibitors, and pan-RAF inhibitors (i.e., RAF inhibitors that are inhibiting more than one member of the RAF family (i.e., two or all three of ARAF, BRAF, and CRAF), e.g., pan-RAF dimer inhibitors (i.e., pan-RAF inhibitors that can bind and inhibit RAF dimers (e.g., RAF heterodimers))), and ERK inhibitors (e.g., ERK1 inhibitors and ERK2 inhibitors).

The term "BRAF inhibitor" or "BRAF antagonist" refers to a molecule that decreases, blocks, inhibits, abrogates, or interferes with BRAF activation or function. In a particular embodiment, a BRAF inhibitor has a binding affinity (dissociation constant) to BRAF of about 1,000 nM or less. In another embodiment, a BRAF inhibitor has a binding affinity to BRAF of about 100 nM or less. In another embodiment, a BRAF inhibitor has a binding affinity to BRAF of about 50 nM or less. In another embodiment, a BRAF inhibitor has a binding affinity to BRAF of about 10 nM or less. In another embodiment, a BRAF inhibitor has a binding affinity to BRAF of about 1 nM or less. In a particular embodiment, a BRAF inhibitor inhibits BRAF signaling with an 1050 of 1,000 nM or less. In another embodiment, a BRAF inhibitor inhibits BRAF signaling with an 1050 of 500 nM or less. In another embodiment, a BRAF inhibitor inhibits BRAF signaling with an 1050 of 50 nM or less. In another embodiment, a BRAF inhibitor inhibits BRAF signaling with an 1050 of 10 nM or less. In another embodiment, a BRAF inhibitor inhibits BRAF signaling with an 1050 of 1 nM or less. Examples of BRAF inhibitors that may be used in accordance with the invention include, without limitation, vemurafenib (ZELBORAF®), dabrafenib, encorafenib (LGX818), GDC-0879, XL281, ARQ736, PLX3603, RAF265, and sorafenib, or a pharmaceutically acceptable salt thereof. BRAF inhibitors may inhibit only BRAF or may inhibit BRAF and one or more additional targets. Preferred BRAF inhibitors are described in PCT Application Publication Nos. WO 2005/062795, WO 2007/002325, WO 2007/002433, WO 2008/079903, and WO 2008/079906, each of which is incorporated herein by reference in its entirety.

The term "ERK inhibitor" or "ERK antagonist" refers to molecule that decreases, blocks, inhibits, abrogates, or interferes with ERK (e.g., ERK1 and/or ERK2) activation or function. In a particular embodiment, an ERK inhibitor has a binding affinity (dissociation constant) to ERK of about 1,000 nM or less. In another embodiment, an ERK inhibitor has a binding affinity to ERK of about 100 nM or less. In another embodiment, an ERK inhibitor has a binding affinity to ERK of about 50 nM or less. In another embodiment, an ERK inhibitor has a binding affinity to ERK of about 10 nM or less. In another embodiment, an ERK inhibitor has a binding affinity to ERK of about 1 nM or less. In a particular embodiment, an ERK inhibitor inhibits ERK signaling with an 1050 of 1,000 nM or less. In another embodiment, an ERK inhibitor inhibits ERK signaling with an 1050 of 500 nM or less. In another embodiment, an ERK inhibitor inhibits ERK signaling with an 1050 of 50 nM or less. In another embodiment, an ERK inhibitor inhibits ERK signaling with an 1050 of 10 nM or less. In another embodiment, an ERK inhibitor inhibits ERK signaling with an 1050 of 1 nM or less. Examples of ERK inhibitors that may be used in accordance with the invention include, without limitation, ravoxertinib (GDC-0994) and ulixertinib (BVD-523), or a pharmaceutically acceptable salt (e.g., a besylate salt (e.g., a besylate salt of ravoxertinib)) thereof. ERK inhibitors may inhibit only ERK or may inhibit ERK and one or more additional targets. Preferred ERK inhibitors are described in PCT Application Publication Nos. WO 2013/130976, WO 2012/118850, WO 2013/020062, WO 2015/154674, WO 2015/085007, WO 2015/032840, WO 2014/036015, WO 2014/060395, WO 2015/103137, and WO 2015/103133, each of which is incorporated herein by reference in its entirety.

The term "MEK inhibitor" or "MEK antagonist" refers to molecule that decreases, blocks, inhibits, abrogates, or interferes with MEK (e.g., MEK1 and/or MEK2) activation or function. In a particular embodiment, a MEK inhibitor has a binding affinity (dissociation constant) to MEK of about 1,000 nM or less. In another embodiment, a MEK inhibitor has a binding affinity to MEK of about 100 nM or less. In another embodiment, a MEK inhibitor has a binding affinity to MEK of about 50 nM or less. In another embodiment, a MEK inhibitor has a binding affinity to MEK of about 10 nM or less. In another embodiment, a MEK inhibitor has a binding affinity to MEK of about 1 nM or less. In a particular embodiment, a MEK inhibitor inhibits MEK signaling with an 1050 of 1,000 nM or less. In another embodiment, a MEK inhibitor inhibits MEK signaling with an 1050 of 500 nM or less. In another embodiment, a MEK inhibitor inhibits MEK signaling with an 1050 of 50 nM or less. In another embodiment, a MEK inhibitor inhibits MEK signaling with an 1050 of 10 nM or less. In another embodiment, a MEK inhibitor inhibits MEK signaling with an 1050 of 1 nM or less. Examples of MEK inhibitors that may be used in accordance with the invention include, without limitation, cobimetinib (e.g., cobimetinib hemifumarate; COTELLIC®), trametinib, binimetinib, selumetinib, pimasertinib, refametinib, GDC-0623, PD-0325901, and BI-847325, or a pharmaceutically acceptable salt thereof. MEK inhibitors may inhibit only MEK or may inhibit MEK and one or more additional targets. Preferred MEK inhibitors are described in PCT Application Publication Nos. WO 2007/044515, WO 2008/024725, WO 2008/024724, WO 2008/067481, WO 2008/157179, WO 2009/085983, WO 2009/085980, WO 2009/082687, WO 2010/003025, and WO 2010/003022, each of which is incorporated herein by reference in its entirety.

The term "CRAF inhibitor" or "CRAF antagonist" refers to molecule that decreases, blocks, inhibits, abrogates, or interferes with CRAF activation or function. In a particular embodiment, a CRAF inhibitor has a binding affinity (dissociation constant) to CRAF of about 1,000 nM or less. In another embodiment, a CRAF inhibitor has a binding affinity to CRAF of about 100 nM or less. In another embodiment, a CRAF inhibitor has a binding affinity to CRAF of about 50 nM or less. In another embodiment, a CRAF inhibitor has a binding affinity to CRAF of about 10 nM or less. In another embodiment, a CRAF inhibitor has a binding affinity to CRAF of about 1 nM or less. In a particular embodiment, a CRAF inhibitor inhibits CRAF signaling with an 1050 of 1,000 nM or less. In another embodiment, a CRAF inhibitor inhibits CRAF signaling with an 1050 of 500 nM or less. In another embodiment, a CRAF inhibitor inhibits CRAF signaling with an 1050 of 50 nM or less. In another embodiment, a CRAF inhibitor inhibits CRAF signaling with an 1050 of 10 nM or less. In another embodiment, a CRAF inhibitor inhibits CRAF signaling with an 1050 of 1 nM or less. Examples of CRAF inhibitors that may be used in accordance with the invention include, without limitation, sorafenib, or a pharmaceutically acceptable salt thereof. CRAF inhibitors may inhibit only CRAF or may inhibit CRAF and one or more additional targets.

The term "pan-RAF inhibitor" or "pan-RAF antagonist" refers to a molecule that decreases, blocks, inhibits, abrogates, or interferes with the activation or function of two or more RAF family members (e.g., two or more of ARAF, BRAF, and CRAF). In one embodiment, the pan-RAF inhibitor inhibits all three RAF family members (i.e., ARAF, BRAF, and CRAF) to some extent. In a particular embodiment, a pan-RAF inhibitor has a binding affinity (dissociation constant) to one, two, or three of ARAF, BRAF, and/or CRAF of about 1,000 nM or less. In another embodiment, a pan-RAF inhibitor has a binding affinity to one, two, or three of ARAF, BRAF, and/or CRAF of about 100 nM or less. In another embodiment, a pan-RAF inhibitor has a binding affinity to one, two, or three of ARAF, BRAF, and/or CRAF of about 50 nM or less. In another embodiment, a pan-RAF inhibitor has a binding affinity to one, two, or three of ARAF, BRAF, and/or CRAF of about 10 nM or less. In another embodiment, a pan-RAF inhibitor has a binding affinity to one, two, or three of ARAF, BRAF, and/or CRAF of about 1 nM or less. In a particular embodiment, a pan-RAF inhibitor inhibits ARAF, BRAF, and/or CRAF signaling with an 1050 of 1,000 nM or less. In another embodiment, a pan-RAF inhibitor inhibits ARAF, BRAF, and/or CRAF signaling with an 1050 of 500 nM or less. In another embodiment, a pan-RAF inhibitor inhibits ARAF, BRAF, and/or CRAF signaling with an 1050 of 50 nM or less. In another embodiment, a pan-RAF inhibitor inhibits ARAF, BRAF, and/or CRAF signaling with an 1050 of 10 nM or less. In another embodiment, a pan-RAF inhibitor inhibits ARAF, BRAF, and/or CRAF signaling with an 1050 of 1 nM or less. Examples of pan-RAF inhibitors that may be used in accordance with the invention include, without limitation, LY-3009120, HM95573 (GDC-5573), LXH-254, MLN2480, BeiGene-283, RXDX-105, BAL3833, regorafenib, and sorafenib, or a pharmaceutically acceptable salt thereof. Pan-RAF inhibitors may inhibit ARAF, BRAF, and/or CRAF and one or more additional targets. Preferred pan-RAF inhibitors are described in PCT Application Publication Nos. WO2013/100632, WO2014/151616, and WO2015/075483, each of which is incorporated herein by reference in its entirety.

In some embodiments, the pan-RAF inhibitor is a "pan-RAF dimer inhibitor" that can bind and inhibit RAF dimers (e.g., RAF heterodimers, e.g., BRAF-CRAF heterodimers). Pan-RAF dimer inhibitors may also bind and inhibit RAF monomers, in addition to RAF dimers (e.g., RAF heterodimers, e.g., BRAF-CRAF heterodimers). Pan-RAF dimer inhibitors include, for example, Type II RAF inhibitors that are capable of decreasing, blocking, inhibiting, abrogating, or interfering with the activation or function of two or more RAF family members.

The term "PI3K inhibitor" refers to a molecule that decreases, blocks, inhibits, abrogates, or interferes with the activation or function of one or more classes of phosphatidyl inositol 3 kinases (PI3Ks), including class I, II, III, and IV PI3Ks. The four classes of PI3Ks are categorized based on structure and substrate specificity. Class I PI3Ks are most closely associated with human disease such as cancer. Class I PI3Ks can be further divided into four different isoforms, PI3Kα, PI3Kβ, PI3Kγ, and PI3Kδ.

In some embodiments, the PI3K inhibitor is a "pan-PI3K inhibitor," by which is meant any compound capable of preferentially inhibiting class I PI3Ks over any other kinase enzymes. For example, a pan-class I PI3K inhibitor is at least two times more potent, preferably at least 5 times more potent, and more preferably at least 10 times more potent, against class I PI3Ks than against other kinases, including the related phosphatidyl inositol 3 kinase-related kinase (PIKK), mammalian target of rapamycin (mTOR). In particular, the PI3K inhibitors may be small molecules or may be biological macromolecules. Typically, the PI3K inhibitors are small molecules, preferably synthetic compounds such as those described in U.S. Patent Application Pub. No. 2010/0249126.

In other embodiments, the PI3K inhibitor may be specific for a particular PI3K isoform. For example, a "PI3Kα-specific inhibitor" means any compound capable of preferentially inhibiting PI3Kα over at least one (e.g., one, two, or three) other PI3K class I isoform (PI3Kβ, PI3Kδ, and/or PI3Kγ). For example, a PI3Kα-specific inhibitor is at least two times more potent, preferably at least 5 times more potent, and more preferably at least 10 times more potent, against PI3Kα than against PI3Kβ, but may or may not be at least two times, at least 5 times, or at least 10 times more potent against PI3Kα and/or PI3Kγ or other non-class I PI3Ks such as class II PI3Ks (e.g., PI3K-C2α), class III PI3Ks (e.g., Vps34), or class IV PI3Ks (e.g., mTOR or DNA-PK). Likewise, a "PI3Kδ-specific inhibitor" means any compound capable of preferentially inhibiting PI3Kδ over at least one (e.g., one, two, or three) other PI3K class I isoform (PI3Kα, PI3Kβ, and/or PI3Kγ).

A "KRAS activating mutation" is any mutation of the KRAS gene (i.e., a nucleic acid mutation) or Kras protein (i.e., an amino acid mutation) that results in aberrant Kras protein function associated with increased and/or constitutive activity by favoring the active GTP-bound state of the Kras protein. The mutation may be at conserved sites that favor GTP binding and constitutively active Kras protein. In some instances, the mutation is at one or more of codons 12, 13, and 16 of the KRAS gene (e.g., a KRAS c.38G>A transition mutation that results in a KRAS protein having an aspartic acid (D) at amino acid position 13 instead of a glycine (G), i.e., a KRAS-G13D mutated protein). Other exemplary KRAS activating mutations include, for example, KRAS-G12D, KRAS-G12C, KRAS-G12V, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, and KRAS-Q61R, as well as corresponding nucleic acid mutations in the KRAS gene that encode for the denoted amino acid change of the Kras protein.

An "NRAS activating mutation" is any mutation of the NRAS gene (i.e., a nucleic acid mutation) or Nras protein (i.e., an amino acid mutation) that results in aberrant Nras protein function associated with increased and/or constitutive activity by favoring the active GTP-bound state of the Nras protein. The mutation may be at conserved sites that favor GTP binding and constitutively active Nras protein. In some instances, the mutation is at one or more of codons 12, 13, and 16 of the NRAS gene. Exemplary NRAS activating mutations include, for example, NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, and NRAS-Q61P, as well as corresponding nucleic acid mutations in the NRAS gene that encode for the denoted amino acid alteration of the Nras protein.

A "BRAF activating mutation" is any mutation of the BRAF gene (i.e., a nucleic acid mutation) or B-Raf protein (i.e., an amino acid mutation) that results in aberrant B-Raf protein function associated with increased and/or constitutive activity by favoring the active state of the B-Raf protein. The mutation may be at conserved sites that favor RAS-GTP binding and constitutively active B-Raf protein. In some instances, the mutation is at codon 600 of the BRAF gene. Exemplary BRAF activating mutations include, for example, BRAF-V600E, BRAF-V600K, BRAF-V600R, and BRAF-V600D, as well as corresponding nucleic acid mutations in the BRAF gene that encode for the denoted amino acid alteration of the B-Raf protein.

An "individual," "patient," or "subject" herein refers to an animal (including, e.g., a mammal, such as a dog, a cat, a horse, a rabbit, a zoo animal, a cow, a pig, a sheep, a non-human primate, and a human), eligible for treatment who is experiencing, has experienced, has risk of developing, or has a family history of one or more signs, symptoms, or other indicators of a cell proliferative disease or disorder, such as a cancer. Intended to be included as a patient is any patient involved in clinical research trials not showing any clinical sign of disease, involved in epidemiological studies, or once used as controls. The patient may have been previously treated with a MAPK signaling inhibitor, another drug (e.g., a PI3K inhibitor), or not previously treated. The patient may be naive to an additional drug(s) being used when the treatment is started, i.e., the patient may not have been previously treated with, for example, a therapy other than one including a MAPK signaling inhibitor (e.g., a MEK inhibitor, a BRAF inhibitor, an ERK inhibitor, a CRAF inhibitor, or a RAF inhibitor) or a PI3K inhibitor at "baseline" (i.e., at a set point in time before the administration of a first dose of one or more MAPK pathway and/or PI3K inhibitors (e.g., a pan-RAF dimer inhibitor and either a MEK inhibitor or a PI3K inhibitor) in the treatment method herein, such as the day of screening the subject before treatment is commenced). Such a "naive" patient or subject is generally considered a candidate for treatment with such additional drug(s).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

A "mutation" is a deletion, insertion, or substitution of one or more nucleotides or one or more amino acids relative to a reference nucleotide sequence or reference amino acid sequence, respectively, such as a wild-type sequence.

"Polynucleotide" or "nucleic acid," as used interchangeably herein, refers to polymers of nucleotides of any length and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, and the like) and with charged linkages (e.g., phosphorothioates, phosphorodithioates, and the like), those containing pendant moieties, such as, for example, proteins (e.g., nucleases, toxins, antibodies, signal peptides, poly-L-lysine, and the like), those with intercalators (e.g., acridine, psoralen, and the like), those containing chelators (e.g., metals, radioactive metals, boron, oxidative metals, and the like), those containing alkylators, those with modified linkages (e.g., alpha anomeric nucleic acids), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or aralkyl. Not all linkages in a polynucleotide need be identical. A polynucleotide can contain one or more different types of modifications as described herein and/or multiple modifications of the same type. The preceding description applies to all polynucleotides referred to herein, including RNA and DNA.

"Oligonucleotide," as used herein, generally refers to short, single stranded, polynucleotides that are typically, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single-stranded polynucleotide that is capable of hybridizing to a nucleic acid and allowing polymerization of a complementary nucleic acid, generally by providing a free 3'-OH group.

The term "small molecule" refers to any molecule with a molecular weight of about 2,000 daltons or less, preferably of about 500 daltons or less.

The term "detection" includes any means of detecting, including direct and indirect detection.

The term "biomarker" as used herein refers to an indicator molecule or set of molecules (e.g., predictive, diagnostic, and/or prognostic indicator), which can be detected in a sample and includes, for example, a KRAS-G13D mutation or an NRAS activating mutation of the protein and/or corresponding activating mutations at the nucleotide level (e.g., a nucleotide mutation of the KRAS or NRAS gene, e.g., a KRAS c.38G>A nucleotide substitution mutation).

The biomarker may be a predictive biomarker and serve as an indicator of the likelihood of sensitivity or benefit of a patient having a particular disease or disorder (e.g., a proliferative cell disorder (e.g., cancer)) to treatment with, for example, a pan-RAF dimer inhibitor and a MEK inhibitor or a PI3K inhibitor. Biomarkers include, but are not limited to, polynucleotides (e.g., DNA and/or RNA (e.g., mRNA)), polynucleotide copy number alterations (e.g., DNA copy numbers), polypeptides, polypeptide and polynucleotide modifications (e.g., post-translational modifications), carbohydrates, and/or glycolipid-based molecular markers. In some embodiments, as referenced above, a biomarker is a gene (e.g., the KRAS or NRAS gene).

The "presence" of a biomarker, as used herein, is a detectable amount in a biological sample. These can be measured by methods known to one skilled in the art and also disclosed herein.

"Amplifying" or "amplification" as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid obtained from a single source (e.g., an individual) using more than one primer set for the purpose of amplifying two or more DNA sequences in a single reaction.

The technique of "polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 51:263 (1987) and Erlich, ed., *PCR Technology*, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real-time polymerase chain reaction" or "qRT-PCR" refers to a form of PCR wherein the amount of PCR product is measured at each step in a PCR reaction. This technique has been described in various publications including, for example, Cronin et al., *Am. J. Pathol.* 164(1): 35-42 (2004) and Ma et al., *Cancer Cell* 5:607-616 (2004).

The term "microarray" refers to an ordered arrangement of hybridizable array elements, preferably polynucleotide probes, on a substrate.

The term "sample," as used herein, refers to a composition that is obtained or derived from a subject (e.g., individual of interest) that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples (e.g., tumor tissue samples), primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

By "tissue sample" is meant a collection of similar cells obtained from a tissue of a subject or individual. The source of the tissue sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; and cells from any time in gestation or development of the subject. The tissue sample may also be primary or cultured cells or cell lines. Optionally, the tissue sample is obtained from a disease tissue/organ. For instance, a "tumor tissue sample" is a tissue sample obtained from a tumor or other cancerous tissue. The tissue sample may contain a mixed population of cell types (e.g., tumor cells and non-tumor cells, cancerous cells and non-cancerous cells). The tissue sample may contain compounds that are not naturally intermixed with the tissue in nature, such as preservatives, anticoagulants, buffers, fixatives, nutrients, antibiotics, or the like.

A "reference sample," "reference cell," "reference tissue," "control sample," "control cell," or "control tissue," as used herein, refers to a sample, cell, tissue, standard, or level that is used for comparison purposes. In one embodiment, a reference level, reference sample, reference cell, reference tissue, control sample, control cell, or control tissue is obtained from a healthy and/or non-diseased part of the body (e.g., tissue or cells) of the same subject or individual. For example, the reference level, reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference level, reference sample, reference cell, reference tissue, control sample, control cell, or control tissue is obtained from a healthy and/or non-diseased part of the body (e.g., tissues or cells) of an individual who is not the subject or individual. In even another embodiment, a reference level, reference sample, reference cell, reference tissue, control sample, control cell, or control tissue is obtained from an untreated tissue and/or cell of the body of an individual who is not the subject or individual.

For the purposes herein a "section" of a tissue sample means a single part or piece of a tissue sample, for example, a thin slice of tissue or cells cut from a tissue sample (e.g., a tumor sample). It is to be understood that multiple sections of tissue samples may be taken and subjected to analysis, provided that it is understood that the same section of tissue sample may be analyzed at both morphological and molecular levels, or analyzed with respect to polypeptides (e.g., by immunohistochemistry) and/or polynucleotides (e.g., by in situ hybridization).

By "correlate" or "correlating" is meant comparing, in any way, the performance and/or results of a first analysis or protocol with the performance and/or results of a second analysis or protocol. For example, one may use the results of a first analysis or protocol in carrying out a second protocol and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down or complete arrest; (2) a reduction in tumor size; (3) inhibition (i.e., reduction, slowing down, or complete stopping) of cancer cell infiltration into adjacent peripheral organs and/or tissues; (4) inhibition (i.e. reduction, slowing down, or complete stopping) of metastasis; (5) relief, to some extent, of one or more symptoms associated with the disease or disorder (e.g., cancer); (6) increase or extension in the length of survival, including overall survival and progression free survival; and/or (7) decreased mortality at a given point of time following treatment.

An "effective response" of an individual or an individual's "responsiveness" to treatment refers to the clinical or therapeutic benefit imparted to a patient at risk for, or having, a disease or disorder, such as cancer. In one embodiment, such benefit includes any one or more of extending survival (including overall survival and/or progression-free survival); resulting in an objective response (including a complete response or a partial response); or improving signs or symptoms of cancer. In one embodiment, at least one biomarker (e.g., a KRAS-G13D mutation or an NRAS activating mutation) is used to identify a patient who is predicted to have an increased likelihood of being responsive to treatment including a pan-RAF inhibitor (e.g., a pan-RAF dimer inhibitor), alone or in combination with a MEK inhibitor, a PI3K inhibitor (e.g., a pan-PI3K inhibitor), and/or an additional therapeutic agent (e.g., an immunotherapy agent, a cytotoxic agent, a growth inhibitory agent, a radiation therapy agent, and an anti-angiogenic agent), relative to a patient who does not have or express the biomarker. In one embodiment, at least one biomarker (e.g., a KRAS-G13D mutation or an NRAS activating mutation) is used to identify the patient who is predicted to have an increase likelihood of being responsive to treatment including a pan-RAF inhibitor (e.g., a pan-RAF dimer inhibitor), alone or in combination with a MEK inhibitor, a PI3K inhibitor (e.g., a pan-PI3K inhibitor), and/or an additional therapeutic agent (e.g., an immunotherapy agent, a cytotoxic agent, a growth inhibitory agent, a radiation therapy agent, and an anti-angiogenic agent), relative to a patient who does not have or express the biomarker.

An "objective response" refers to a measurable response, including complete response (CR) or partial response (PR).

In some embodiments, the "objective response rate (ORR)" refers to the sum of complete response (CR) rate and partial response (PR) rate.

By "complete response" or "CR" is intended the disappearance of all signs of a proliferative cell disorder such as cancer (e.g., disappearance of all target lesions) in response to treatment. This does not always mean the disease (e.g., cancer) has been cured.

"Sustained response" refers to the sustained effect on reducing tumor growth after cessation of a treatment. For example, the tumor size may be the same size or smaller as compared to the size at the beginning of the medicament administration phase. In some embodiments, the sustained response has a duration at least the same as the treatment duration, at least 1.5×, 2.0×, 2.5×, or 3.0× length of the treatment duration, or longer.

As used herein, "reducing or inhibiting cancer relapse" means to reduce or inhibit tumor or cancer relapse or tumor or cancer progression. As disclosed herein, cancer relapse and/or cancer progression include, without limitation, cancer metastasis.

As used herein, "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

The term "survival" refers to the patient remaining alive, and includes overall survival as well as progression-free survival.

As used herein, "progression-free survival" or "PFS" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" or "OS" refers to the percentage of individuals in a group who are likely to be alive after a particular duration of time.

By "extending survival" is meant increasing overall or progression-free survival in a treated patient relative to an untreated patient (i.e. relative to a patient not treated with the medicament), or relative to a patient who does not express a biomarker at the designated level, and/or relative to a patient treated with an anti-tumor agent.

A "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), response rates (e.g., CR and PR), duration of response, and/or quality of life.

A "disorder" is any condition that would benefit from treatment including, but not limited to, chronic and acute disorders or diseases including those pathological conditions which predispose the mammal to the disorder in question.

The terms "cancer" and "cancerous" refer to or describe the physiological condition in mammals that is typically characterized by unregulated cell growth. Included in this definition are benign and malignant cancers. Examples of cancer include, but are not limited to, carcinoma; lymphoma; blastoma (including medulloblastoma and retinoblastoma); sarcoma (including liposarcoma and synovial cell sarcoma); neuroendocrine tumors (including carcinoid tumors, gastrinoma, and islet cell cancer); mesothelioma; schwannoma (including acoustic neuroma); meningioma; adenocarcinoma; melanoma; and leukemia or lymphoid malignancies. More particular examples of such cancers include bladder cancer (e.g., urothelial bladder cancer (e.g., transitional cell or urothelial carcinoma, non-muscle invasive bladder cancer, muscle-invasive bladder cancer, and metastatic bladder cancer) and non-urothelial bladder cancer); squamous cell cancer (e.g., epithelial squamous cell cancer); lung cancer, including small-cell lung cancer (SCLC), non-small cell lung cancer (NSCLC), adenocarcinoma of the lung, and squamous carcinoma of the lung; cancer of the peritoneum; hepatocellular cancer; gastric or stomach cancer, including gastrointestinal cancer; pancreatic cancer; glioblastoma; cervical cancer; ovarian cancer; liver cancer; hepatoma; breast cancer (including metastatic breast cancer); colon cancer; rectal cancer; colorectal cancer; endometrial or uterine carcinoma; salivary gland carcinoma; kidney or renal cancer; prostate cancer; vulval cancer; thyroid cancer; hepatic carcinoma; anal carcinoma; penile carcinoma; Merkel cell cancer; mycosis fungoides; testicular cancer; esophageal cancer; tumors of the biliary tract; head and neck cancer; and hematological malignancies. In some embodiments, the cancer is triple-negative metastatic breast cancer, including any histologically confirmed triple-negative (ER−, PR−, HER2−) adenocarcinoma of the breast with locally recurrent or metastatic disease (where the locally recurrent disease is not amenable to resection with curative intent). In some embodiments, the cancer is skin cancer, including a melanoma, e.g., a melanoma with locally recurrent or metastatic disease (where the locally recurrent disease is not amenable to resection with curative intent). Any cancer can be at early stage or at late stage. By "early stage cancer" or "early stage tumor" is meant a cancer that is not invasive or metastatic or is classified as a Stage 0, 1, or 2 cancer.

The term "tumor," as used herein, refers to all neoplastic cell growth and proliferation, whether malignant or benign, and all pre-cancerous and cancerous cells and tissues. The terms "cancer," "cancerous," and "tumor" are not mutually exclusive as referred to herein.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

The term "pharmaceutically acceptable salt" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids, such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids, such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines, including naturally occurring substituted amines, cyclic amines, and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, a pan-RAF dimer inhibitor is used to delay development of a disease or to slow the progression of a disease. In some embodiments, a pan-RAF dimer inhibitor is used in combination with a MEK inhibitor or a PI3K inhibitor (e.g., a pan-PI3K inhibitor) to delay development of a disease or to slow the progression of a disease.

The term "anti-cancer therapy" refers to a therapy useful in treating cancer. Examples of anti-cancer therapeutic agents include, but are limited to, cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC® (imatinib mesylate)), a COX-2 inhibitor (e.g., celecoxib), interferons, cytokines, antagonists (e.g., neutralizing antibodies) that bind to one or more of the following targets PDGFR-β, BlyS, APRIL, BCMA receptor(s), TRAIL/Apo2, other bioactive and organic chemical agents, and the like. Combinations thereof are also included in the invention.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® (cyclosphosphamide); alkyl sulfonates such as busulfan, improsulfan and piposulfan; aziridines such as benzodopa, carboquone, meturedopa, and uredopa; ethylenimines and methylmelamines including altretamine, triethylenemelamine, triethylenephosphoramide, triethylenethiophosphoramide and trimethylol melamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (see, e.g., Nicolaou et al., Angew. Chem Intl. Ed. Engl., 33: 183-186 (1994)), dynemicin, including dynemicin A, an esperamicin, as well as neocarzinostatin chromophore and related chromoprotein enediyne antibiotic chromophores), aclacinomycins, actinomycin, authramycin, azaserine, bleomycins, cactinomycin, carubicin, carminomycin, carzinophilin, chromomycin, dactinomycin, daunorubicin, detorubicin, 6-diazo-5-oxo-L-norleucine, ADRIAMYCIN® (doxorubicin) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidanmol; nitracrine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, for example taxanes including TAXOL® (paclitaxel) (Bristol-Myers Squibb Oncology, Princeton, N.J.), ABRAXANE™ (Cremophor-free, albumin-engineered nanoparticle formulation of paclitaxel) (American Pharmaceutical Partners, Schaumberg, Illinois), and TAXOTERE® (docetaxel) (Rhone-Poulenc Rorer, Antony, France); chlorambucil; gemcitabine (GEMZAR®); 6-thioguanine; mercaptopurine; methotrexate; platinum or platinum-based chemotherapy agents and platinum analogs, such as cisplatin, carboplatin, oxaliplatin (ELOXATIN™), satraplatin, picoplatin, nedaplatin, triplatin, and lipoplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts or acids of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin. Additional chemotherapeutic agents include the cytotoxic agents useful as antibody drug conjugates, such as maytansinoids (DM1, for example) and the auristatins MMAE and MMAF, for example.

"Chemotherapeutic agents" also include "anti-hormonal agents" or "endocrine therapeutics" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts or acids of any of the above.

Chemotherapeutic agents also include antibodies such as alemtuzumab (Campath®), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar®, Corixa), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories), which is a recombinant exclusively human-sequence, full-length IgG1 λ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3, and E7.6.3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP 659,439A2, Merck Patent GmbH). EGFR antagonists include small molecules such as compounds described in U.S. Pat. Nos. 5,616,582, 5,457, 105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO 98/14451, WO 98/50038, WO 99/09016, and WO 99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenylamino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitors such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035 and 4-(3-chloroanilino)quinazoline; pyridopyrimidines; pyrimidopyrimidines; pyrrolopyrimidines, such as CGP 59326, CGP 60261 and CGP 62706; pyrazolopyrimidines; 4-(phenylamino)-7H-pyrrolo[2,3-d]pyrimidines; curcumin (diferuloylmethane); 4,5-bis(4-fluoroanilino)phthalimide; tyrphostins containing nitrothiophene moieties; PD-0183805 (Warner-Lamber); antisense molecules (e.g., those that bind to HER-encoding nucleic acid); quinoxalines (U.S. Pat. No. 5,804, 396); tyrphostins (U.S. Pat. No. 5,804,396); ZD6474 (Astra Zeneca); PTK-787 (Novartis/Schering AG); pan-HER inhibitors such as CI-1033 (Pfizer); Affinitac™ (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacizumab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (ENBREL®), infliximab (REMICADE®), adalimumab (HUMIRA®), certolizumab pegol (CIMZIA®), golimumab (SIMPONI®), Interleukin 1 (IL-1) blockers such as anakinra (KINERET®), T-cell co-stimulation blockers such as abatacept (ORENCIA®), Interleukin 6 (IL-6) blockers such as tocilizumab (ACTEMERA®); Interleukin 13 (IL-13) blockers such as lebrikizumab; Interferon alpha (IFN) blockers such as rontalizumab; beta 7 integrin blockers such as rhuMAb Beta7; IgE pathway blockers such as Anti-M1 prime; secreted homotrimeric LTa3 and membrane bound heterotrimer LTa1/62 blockers such as anti-lymphotoxin alpha (LTa); miscellaneous investigational agents such as thioplatin, PS-341, phenylbutyrate, ET-18-OCH3, and farnesyl transferase inhibitors (L-739749, L-744832); polyphenols such as quercetin, resveratrol, piceatannol, epigallocatechine gallate, theaflavins, flavanols, procyanidins, betulinic acid; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); epidermal growth factor receptor (EGF-R); vaccines such as THERATOPE® vaccine; perifosine; COX-2 inhibitors (e.g., celecoxib or etoricoxib); proteosome inhibitors (e.g., PS341); CCI-779; tipifarnib (R11577); sorafenib; ABT510; Bcl-2 inhibitors such as oblimersen sodium (GENASENSE®); pixantrone; farnesyl-transferase inhibitors such as lonafarnib (SCH 6636, SARASAR™); and pharmaceutically acceptable salts or acids of any of the above; as well as combinations of two or more of the above.

The term "prodrug" as used herein refers to a precursor form of a pharmaceutically active substance that is less cytotoxic to tumor cells compared to the parent drug and is capable of being enzymatically activated or converted into the more active parent form. See, for example, Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth and/or proliferation of a cell (e.g., a cell whose growth is dependent on MAPK pathway signaling) either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl) oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in "*The Molecular Basis of Cancer*," Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, "administering" means a method of giving a dosage of a compound (e.g., an inhibitor or antagonist) or a pharmaceutical composition (e.g., a pharmaceutical composition including an inhibitor or antagonist) to a subject (e.g., a patient). Administering can be by any suitable means, including parenteral, intrapulmonary, and intranasal, and, if desired for local treatment, intralesional administration. Parenteral infusions include, for example, intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

The term "co-administered" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the level of activity and/or function of a protein in the MAPK signaling pathway/PI3K pathway (e.g., RAF, MEK, and/or PI3K). Additionally, reduce or inhibit can refer, for example, to the symptoms of the disorder (e.g., cancer) being treated, the presence or size of metastases, or the size of the primary tumor.

The term "package insert" is used to refer to instructions customarily included in commercial packages of therapeutic products, that contain information about the indications, usage, dosage, administration, combination therapy, contraindications, and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker (e.g., a KRAS-G13D mutation or an NRAS activating mutation) described herein. In certain embodiments, the manufacture or kit is promoted, distributed, or sold as a unit for performing the methods described herein.

The phrase "based on" when used herein means that the information about one or more biomarkers is used to inform a diagnostic decision, a treatment decision, information provided on a package insert, or marketing/promotional guidance, etc.

III. Methods

A. Diagnostic Methods

The present invention provides methods for identifying individuals having cancer (e.g., colorectal cancer, ovarian cancer, lung cancer, pancreatic cancer, and skin cancer (e.g., melanoma)) who may benefit from treatment including a pan-RAF inhibitor (e.g., a pan-RAF dimer inhibitor) and a MEK inhibitor or a PI3K inhibitor. The methods include screening a sample (e.g., a tissue sample (e.g., a tumor tissue sample)) from the individual for a KRAS activating mutation (e.g., a KRAS-G13D mutation), wherein the presence of a KRAS activating mutation (e.g., a KRAS-G13D mutation) in the sample identifies the individual as one who may benefit from treatment comprising a pan-RAF inhibitor (e.g., a pan-RAF dimer inhibitor) and a MEK or PI3K inhibitor. Also provided are methods for selecting a treatment for an individual having a cancer. These methods similarly include a step of screening a sample from the individual for a KRAS activating mutation (e.g., a KRAS-G13D mutation), wherein the presence of a KRAS activating mutation (e.g., a KRAS-G13D mutation) in the sample identifies the individual as one who may benefit from a treatment comprising a pan-RAF inhibitor (e.g., a pan-RAF dimer inhibitor) and a MEK or PI3K inhibitor. Also provided are methods for optimizing therapeutic efficacy for treatment of an individual having a cancer, wherein the treatment includes a pan-RAF inhibitor (e.g., a pan-RAF dimer inhibitor) and a MEK inhibitor or a PI3K inhibitor. Further provided herein are methods for predicting responsiveness of an individual having a cancer to treatment including a pan-RAF inhibitor (e.g., a pan-RAF dimer inhibitor) and a MEK inhibitor or PI3K inhibitor. Any of the methods may further include administering to the individual a therapeutically effective amount of a pan-RAF inhibitor (e.g., a pan-RAF dimer inhibitor) and a MEK or PI3K inhibitor, for example, based on the presence of a KRAS activating mutation (e.g., a KRAS-G13D mutation). In addition, any of the methods may further include administering a therapeutically effective amount of an additional therapeutic agent (e.g., an immunotherapy agent, a cytotoxic agent, a growth inhibitory agent, a radiation therapy agent, and an anti-angiogenic agent) to the individual.

In some instances, the invention provides methods for identifying an individual having a cancer (e.g., colorectal cancer, ovarian cancer, lung cancer, pancreatic cancer, and skin cancer (e.g., melanoma)) who may benefit from treatment including a pan-RAF inhibitor (e.g., a pan-RAF dimer inhibitor) and a MEK inhibitor based on screening a sample (e.g., a tissue sample (e.g., a tumor tissue sample)) from the individual for a KRAS-G13D mutation, wherein the presence of a KRAS-G13D mutation in the sample indicates that the individual has an increased likelihood of benefiting from treatment including a pan-RAF inhibitor (e.g., a pan-RAF dimer inhibitor) and a MEK inhibitor. The screening may include amplifying and sequencing all or a portion of the KRAS gene, for example, to determine the particular genotype of the individual. Accordingly, the screening may include specifically amplifying and sequencing all or a portion of exon 2 of the KRAS gene, wherein a KRAS c.38G>A nucleotide substitution mutation at codon 13 of exon 2 of the KRAS gene is indicative of a KRAS-G13D mutation. In other instances, the screening may include sequencing all or a portion of the KRAS protein, for example, to determine whether the individual has a KRAS-G13D amino acid mutation. In instances in which the individual has a KRAS-G13D mutation, the methods may further include a step of administering to the individual a therapeutically effective amount of a pan-RAF inhibitor (e.g., a pan-RAF dimer inhibitor) and a MEK inhibitor, optionally in combination with one or more additional therapeutic agents (e.g., immunotherapy agents, cytotoxic agents, growth inhibitory agents, radiation therapy agents, and anti-angiogenic agents).

In some instances, the invention also provides methods for selecting a treatment for an individual having a cancer (e.g., colorectal cancer, ovarian cancer, lung cancer, pancreatic cancer, and skin cancer (e.g., melanoma)), wherein the method includes screening a sample (e.g., a tissue sample (e.g., a tumor tissue sample)) from the individual for a KRAS-G13D mutation, wherein the presence of a KRAS-G13D mutation in the sample identifies the individual as one who may benefit from a treatment including a pan-RAF inhibitor (e.g., a pan-RAF dimer inhibitor) and a MEK inhibitor. The screening may include amplifying and sequencing all or a portion of the KRAS gene, for example, to determine the particular genotype of the individual. Accordingly, the screening may include specifically amplifying and sequencing all or a portion of exon 2 of the KRAS gene, wherein a KRAS c.38G>A nucleotide substitution mutation at codon 13 of exon 2 of the KRAS gene is indicative of a KRAS-G13D mutation. In other instances, the screening may include sequencing all or a portion of the KRAS protein, for example, to determine whether the individual has a KRAS-G13D amino acid mutation. In instances in which the individual has a KRAS-G13D mutation, the methods may further include a step of administering to the individual a therapeutically effective amount of a pan-RAF inhibitor (e.g., a pan-RAF dimer inhibitor) and a MEK inhibitor, optionally in combination with one or more additional therapeutic agents (e.g., immunotherapy agents, cytotoxic agents, growth inhibitory agents, radiation therapy agents, and anti-angiogenic agents).

In some instances, the invention provides methods for identifying an individual having a cancer (e.g., colorectal cancer, ovarian cancer, lung cancer, pancreatic cancer, and skin cancer (e.g., melanoma)) who may benefit from treatment including a pan-RAF inhibitor (e.g., a pan-RAF dimer inhibitor) and a PI3K inhibitor (e.g., a pan-PI3K inhibitor) based on screening a sample (e.g., a tissue sample (e.g., a tumor tissue sample)) from the individual for a KRAS activating mutation (e.g., KRAS-G12D, KRAS-G12C, KRAS-G12V, KRAS-G13D, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, or KRAS-Q61R), wherein the presence of a KRAS activating mutation in the sample indicates that the individual has an increased likelihood of benefiting from treatment including a pan-RAF inhibitor (e.g., a pan-RAF dimer inhibitor) and a PI3K inhibitor (e.g., a pan-PI3K inhibitor). The screening may include amplifying and sequencing all or a portion of the KRAS gene, for example, to determine the particular genotype of the individual. Accordingly, the screening may include specifically amplifying and sequencing codon 12, 13, and/or 61 of the KRAS gene. In other instances, the screening may include sequencing all or a portion of the KRAS protein, for example, to determine whether the individual has a KRAS activating amino acid mutation. In instances in which the individual has a KRAS activating mutation, the methods may further include a step of administering to the individual a therapeutically effective amount of a pan-RAF inhibitor (e.g., a pan-RAF dimer inhibitor) and a PI3K inhibitor (e.g., a pan-PI3K inhibitor), optionally in combination with one or more additional therapeutic agents (e.g., immunotherapy agents, cytotoxic agents, growth inhibitory agents, radiation therapy agents, and anti-angiogenic agents). In some instances, the individual does not have a BRAF activating mutation.

In some instances, the invention also provides methods for selecting a treatment for an individual having a cancer (e.g., colorectal cancer, ovarian cancer, lung cancer, pancreatic cancer, and skin cancer (e.g., melanoma)), wherein the method includes screening a sample (e.g., a tissue sample (e.g., a tumor tissue sample)) from the individual for a KRAS activating mutation (e.g., KRAS-G12D, KRAS-G12C, KRAS-G12V, KRAS-G13D, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, or KRAS-Q61R), wherein the presence of a KRAS activating mutation in the sample identifies the individual as one who may benefit from a treatment including a pan-RAF inhibitor (e.g., a pan-RAF dimer inhibitor) and a PI3K inhibitor (e.g., a pan-PI3K inhibitor). The screening may include amplifying and sequencing all or a portion of the KRAS gene, for example, to determine the particular genotype of the individual. Accordingly, the screening may include specifically amplifying and sequencing codons 12, 13, and/or 61 of the KRAS gene. In other instances, the screening may include sequencing all or a portion of the KRAS protein, for example, to determine whether the individual has a KRAS activating amino acid mutation. In instances in which the individual has a KRAS activating mutation, the methods may further include a step of administering to the individual a therapeutically effective amount of a pan-RAF inhibitor (e.g., a pan-RAF dimer inhibitor) and a PI3K inhibitor (e.g., a pan-PI3K inhibitor), optionally in combination with one or more additional therapeutic agents (e.g., immunotherapy agents, cytotoxic agents, growth inhibitory agents, radiation therapy agents, and anti-angiogenic agents). In some instances, the individual does not have a BRAF activating mutation.

The present invention also provides methods for identifying individuals having cancer (e.g., colorectal cancer, ovarian cancer, lung cancer, pancreatic cancer, and skin cancer (e.g., melanoma)) who may benefit from treatment including a pan-RAF inhibitor (e.g., a pan-RAF dimer inhibitor) and a MEK inhibitor, wherein the methods include screening a sample (e.g., a tissue sample (e.g., a tumor tissue sample)) from the individual for an NRAS activating mutation (e.g., NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, or NRAS-Q61P), wherein the presence of an NRAS activating mutation in the sample identifies the individual as one who may benefit from treatment comprising a pan-RAF inhibitor (e.g., a pan-RAF dimer inhibitor) and a MEK inhibitor. Also provided are methods for selecting a treatment for an individual having a cancer. These methods similarly include a step of screening a sample from the individual for an NRAS activating mutation, wherein the presence of an NRAS activating mutation in the sample identifies the individual as one who may benefit from a treatment comprising a pan-RAF inhibitor (e.g., a pan-RAF dimer inhibitor) and a MEK inhibitor. Also provided are methods for optimizing therapeutic efficacy for treatment of an individual having a cancer, wherein the treatment includes a pan-RAF inhibitor (e.g., a pan-RAF dimer inhibitor) and a MEK inhibitor. Further provided herein are methods for predicting responsiveness of an individual having a cancer to treatment including a pan-RAF inhibitor (e.g., a pan-RAF dimer inhibitor) and a MEK inhibitor. Any of the methods may further include administering to the individual a therapeutically effective amount of a pan-RAF inhibitor (e.g., a pan-RAF dimer inhibitor) and a MEK inhibitor, for example, based on the presence of an NRAS activating mutation. In addition, any of the methods may further include administering a therapeutically effective amount of an additional therapeutic agent (e.g., an immunotherapy agent, a cytotoxic agent, a growth inhibitory agent, a radiation therapy agent, and an anti-angiogenic agent) to the individual.

In some instances, the invention provides methods for identifying an individual having a cancer (e.g., colorectal cancer, ovarian cancer, lung cancer, pancreatic cancer, and skin cancer (e.g., melanoma)) who may benefit from treatment including a pan-RAF inhibitor (e.g., a pan-RAF dimer inhibitor) and a MEK inhibitor based on screening a sample (e.g., a tissue sample (e.g., a tumor tissue sample)) from the individual for an NRAS activating mutation (e.g., NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, or NRAS-Q61P), wherein the presence of an NRAS activating mutation in the sample indicates that the individual has an increased likelihood of benefiting from treatment including a pan-RAF inhibitor (e.g., a pan-RAF dimer inhibitor) and a MEK inhibitor. The screening may include amplifying and sequencing all or a portion of the NRAS gene, for example, to determine the particular genotype of the individual. Accordingly, the screening may include specifically amplifying and sequencing codons 12, 13, and/or 61 of the NRAS gene. In other instances, the screening may include sequencing all or a portion of the NRAS protein, for example, to determine whether the individual has an NRAS activating amino acid mutation. In instances in which the individual has an NRAS activating mutation, the methods may further include a step of administering to the individual a therapeutically effective amount of a pan-RAF inhibitor (e.g., a pan-RAF dimer inhibitor) and a MEK inhibitor, optionally in combination with one or more additional therapeutic agents (e.g., immunotherapy agents, cytotoxic agents, growth inhibitory agents, radiation therapy agents, and anti-angiogenic agents).

In some instances, the invention also provides methods for selecting a treatment for an individual having a cancer (e.g., colorectal cancer, ovarian cancer, lung cancer, pancreatic cancer, and skin cancer (e.g., melanoma)), wherein the method includes screening a sample (e.g., a tissue sample (e.g., a tumor tissue sample)) from the individual for an NRAS activating mutation (e.g., NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, or NRAS-Q61P), wherein the presence of an NRAS activating mutation in the sample identifies the individual as one who may benefit from a treatment including a pan-RAF inhibitor (e.g., a pan-RAF dimer inhibitor) and a MEK inhibitor. The screening may include amplifying and sequencing all or a portion of the NRAS gene, for example, to determine the particular genotype of the individual. Accordingly, the screening may include specifically amplifying and sequencing codons 12, 13, and/or 61 of the NRAS gene. In other instances, the screening may include sequencing all or a portion of the NRAS protein, for example, to determine whether the individual has an NRAS activating mutation. In instances in which the individual has an NRAS activating mutation, the methods may further include a step of administering to the individual a therapeutically effective amount of a pan-RAF inhibitor (e.g., a pan-RAF dimer inhibitor) and a MEK inhibitor, optionally in combination with one or more additional therapeutic agents (e.g., immunotherapy agents, cytotoxic agents, growth inhibitory agents, radiation therapy agents, and anti-angiogenic agents).

In any of the preceding methods in which a MEK inhibitor is a component of the treatment, the MEK inhibitor may be a small molecule inhibitor, which may be a prodrug or a biologically active form. For example, the MEK inhibitor may be a small molecule inhibitor selected from the group consisting of cobimetinib (GDC-0973), selumetinib (AZD6244), pimasertib (AS-703026), PD0325901, refametinib (BAY86-9766), binimetinib (MEK162), BI-847325, trametinib, GDC-0623, G-573, and CH5126766 (RO5126766), or a pharmaceutically acceptable salt thereof. In particular instances, the small molecule inhibitor is cobimetinib (GDC-0973), selumetinib (AZD6244), pimasertib (AS-703026), PD0325901, refametinib (BAY86-9766), or binimetinib (MEK162), or a pharmaceutically acceptable salt thereof.

In any of the preceding methods in which a PI3K inhibitor is a component of the treatment, the PI3K inhibitor may be a small molecule inhibitor, which may be a prodrug or a biologically active form. For example, the small molecule inhibitor is selected from the group consisting of pictilisib (GDC-0941), taselisib (GDC-0032), and alpelisib (BYL719), or a pharmaceutically acceptable salt thereof. The PI3K inhibitor may be a pan-PI3K inhibitor (e.g., pictilisib (GDC-0941) or taselisib (GDC-0032), or a pharmaceutically acceptable salt thereof), or a PI3Kα-specific inhibitor and/or PI3Kδ-specific inhibitor.

In any of the preceding methods, the pan-RAF inhibitor may be a pan-RAF dimer inhibitor. In certain instances, the pan-RAF inhibitor (e.g., pan-RAF dimer inhibitor) may be a small molecule inhibitor, which may be a prodrug or a biologically active form. In certain instances, the pan-RAF dimer inhibitor may be HM95573, LY-3009120, AZ-628, LXH-254, MLN2480, BeiGene-283, RXDX-105, BAL3833, regorafenib, or sorafenib, or a pharmaceutically acceptable salt thereof.

The disclosed methods and assays provide for convenient, efficient, and potentially cost-effective means to obtain data and information useful in assessing appropriate or effective therapies for treating patients. For example, a patient can provide a tissue sample (e.g., a tumor biopsy or a blood sample) before and/or after treatment with a pan-RAF inhibitor (e.g., a pan-RAF dimer inhibitor) and a MEK or PI3K inhibitor, and the sample can be examined by way of various in vitro assays to determine whether the patient's cells are sensitive to pan-RAF inhibitors (e.g., a pan-RAF dimer inhibitors) and MEK or PI3K inhibitors.

In any of the preceding methods, identification of the particular mutational status of the KRAS and/or NRAS gene, mRNA, or protein product in a sample obtained from the individual may be performed by any of a number of methods well known to one of skill in the art. For example, identification of the mutation can be accomplished by cloning of the KRAS and/or NRAS gene, or portion thereof, and sequencing it using techniques well known in the art. Alternatively, the gene sequences can be amplified from genomic DNA, e.g. using PCR, and the product sequenced. Several non-limiting methods for analyzing a patient's DNA for mutations at a given genetic locus are described below.

DNA microarray technology, e.g., DNA chip devices and high-density microarrays for high-throughput screening applications and lower-density microarrays, may be used. Methods for microarray fabrication are known in the art and include various inkjet and microjet deposition or spotting technologies and processes, in situ or on-chip photolithographic oligonucleotide synthesis processes, and electronic DNA probe addressing processes. The DNA microarray hybridization applications has been successfully applied in the areas of gene expression analysis and genotyping for point mutations, single nucleotide polymorphisms (SNPs), and short tandem repeats (STRs). Additional methods include interference RNA microarrays and combinations of microarrays and other methods such as laser capture microdissection (LCM), comparative genomic hybridization (CGH) and chromatin immunoprecipitation (ChiP). See, e.g., He et al. (2007) Adv. Exp. Med. Biol. 593:117-133 and Heller (2002) Annu. Rev. Biomed. Eng. 4:129-153. Other methods include PCR, xMAP, invader assay, mass spectrometry, and pyrosequencing (Wang et al. (2007) 593:105-106).

Another detection method is allele specific hybridization using probes overlapping the polymorphic site and having about 5, or alternatively 10, or alternatively 20, or alternatively 25, or alternatively 30 nucleotides around the polymorphic region. For example, several probes capable of hybridizing specifically to a particular mutational variant (e.g., KRAS-G13D, which corresponds to a KRAS c.38G>A nucleotide substitution mutation) are attached to a solid phase support, e.g., a "chip." Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene prior to identifying the mutational variant. Amplification can be performed, e.g., by PCR and/or LCR or other methods well known in the art.

In some cases, the presence of the specific mutation in DNA from a subject can be shown by restriction enzyme analysis. For example, the specific mutation can result in a nucleotide sequence comprising a restriction site which is absent from the nucleotide sequence of another mutational variant or the wild-type version of the gene.

In a further embodiment, protection from cleavage agents (such as a nuclease, hydroxylamine, or osmium tetroxide and with piperidine) can be used to detect mismatched bases in RNA/RNA, DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. Alternatively, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Meth. Enzymol. 217:286-295.

Alterations in electrophoretic mobility may also be used to identify the particular allelic variant. For example, single-strand conformation polymorphism (SSCP) may be used to detect differences in electrophoretic mobility between mutant and wild type nucleic acids (Orita et al. (1989) Proc Natl. Acad. Sci USA 86:2766; Cotton (1993) Mutat. Res. 285:125-144 and Hayashi (1992) Genet. Anal. Tech. Appl. 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another embodiment, the subject method utilizes heteroduplex analysis to separate double-stranded heteroduplex molecules on the basis of changes in electrophoretic mobility (Keen et al. (1991) Trends Genet. 7:5).

The identity of the mutational variant may also be obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys. Chem. 265:1275).

Examples of techniques for detecting differences of at least one nucleotide between two nucleic acid molecules (e.g., DNA or RNA molecules) include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotide hybridization techniques may be used for the detection of the nucleotide changes in the polymorphic region of the gene. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology, which depends on selective PCR amplification, may be useful in conjunction with the instant invention. Oligonucleotides used as primers for specific amplification may carry the allelic variant of interest in the center of the molecule (so that amplification depends on differential hybridization) (Gibbs et al. (1989) Nucl. Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition, it may be desirable to introduce a novel restriction site in the region of the mutation to create cleavage-based detection (Gasparini et al. (1992) *Mol. Cell. Probes* 6:1).

In another embodiment, identification of the mutational variant is carried out using an oligonucleotide ligation assay (OLA), as described, e.g., in U.S. Pat. No. 4,998,617 and in Laridegren, U. et al. *Science* 241:1077-1080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled, If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson et al. have described a nucleic acid detection assay that combines attributes of PCR and OLA (Nickerson, D. A. et al. (1990) *Proc. Natl. Acad. Sci. USA* 87:8923-8927). In this method, PCR is used to achieve the exponential amplification of target DNA, which is then detected using OLA.

Described are methods for detecting a single-nucleotide mutation in a given gene, for example, a RAS gene, such as the KRAS gene or the NRAS gene. Because single-nucleotide changes are flanked by regions of invariant sequence, their analysis requires no more than the determination of the identity of the single variant nucleotide, and it is unnecessary to determine a complete gene sequence for each patient. Several methods have been developed to facilitate the analysis of such mutations.

Single-base mutations can be detected by using a specialized exonuclease-resistant nucleotide, as disclosed, e.g., in U.S. Pat. No. 4,656,127. According to the method, a primer complementary to the mutated sequence immediately 3' to the mutated site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the mutated site of the target molecule was complementary to that of the nucleotide derivative used in the reaction. This method has the advantage that it does not require the determination of large amounts of extraneous sequence data.

A solution-based method may also be used for determining the identity of the nucleotide of the mutated site (WO 91/02087). As above, a primer is employed that is complementary to mutated sequence(s) immediately 3' to a mutated site. The method determines the identity of the nucleotide of that site using labeled dideoxynucleotide derivatives, which, if complementary to the nucleotide of the mutated site, will become incorporated onto the terminus of the primer.

An alternative method is described in WO 92/15712. This method uses mixtures of labeled terminators and a primer that is complementary to the sequence 3' to a mutated or polymorphic site. The labeled terminator that is incorporated is thus determined by, and complementary to, the nucleotide present in the mutated site of the target molecule being evaluated. The method is usually a heterogeneous phase assay, in which the primer or the target molecule is immobilized to a solid phase.

Many other primer-guided nucleotide incorporation procedures for assaying mutated sites in DNA have been described (Komher, J. S. et al. (1989) *Nucl. Acids. Res.* 17:7779-7784; Sokolov, B. P. (1990) *Nucl. Acids Res.* 18:3671; Syvanen, A.-C., et al. (1990) *Genomics* 8:684-692; Kuppuswamy, M. N. et al. (1991) *Proc. Natl. Acad. Sci. USA* 88:1143-1147; Prezant, T. R. et al. (1992) *Hum. Mutat.* 1: 159-164; Ugozzoli, L. et al. (1992) *GATA* 9:107-112; Nyren, P. et al. (1993) *Anal. Biochem.* 208:171-175). These methods all rely on the incorporation of labeled deoxynucleotides to discriminate between bases at a mutated site.

In general, the presence and/or amount of a biomarker gene described herein can be analyzed by a number of methodologies, including those described above, as well as many others known in the art and understood by the skilled artisan, such as Southern analysis, Northern analysis, whole genome sequencing, polymerase chain reaction (PCR) (including quantitative real time PCR (qRT-PCR) and other amplification type detection methods, such as, for example, branched DNA, SISBA, TMA and the like), RNA-Seq, microarray analysis, Nanostring, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, *Current Protocols In Molecular Biology*, Units 2 (Northern Blotting), 4 (Southern Blotting), 15 (Immunoblotting), and 18 (PCR Analysis). Multiplexed immunoassays such as those available from Rules Based Medicine or Meso Scale Discovery ("MSD") may also be used.

In addition, the presence and/or amount of a biomarker protein (i.e., gene product) described herein can be analyzed by a number of methodologies, including immunohistochemistry ("IHC"), Western blot analysis, immunoprecipitation, spectroscopy, molecular binding assays, HPLC, enzyme-linked immunosorbent assay (ELISA), enzyme-linked immunofiltration assay (ELIFA), fluorescence activated cell sorting ("FACS"), MassARRAY, proteomics, quantitative blood based assays (e.g., serum ELISA), biochemical enzymatic activity assays, in situ hybridization, fluorescence in situ hybridization (FISH), and protein sequencing. In certain instances, the method comprises contacting a biological sample from the individual with antibodies that specifically bind to a protein biomarker described herein under conditions permissive for binding of the biomarker, and detecting whether a complex is formed between the antibodies and biomarker. Such a method may be an in vitro or in vivo method. In some instances, the protein expression level of the biomarker (e.g., KRAS-G13D protein or an NRAS protein having an activating mutation, such as one described herein above) is determined in tumor cells (e.g., from a biopsy).

Moreover, it will be understood that any of the above methods for detecting mutations in a gene or gene product can also be used to monitor the course of treatment or therapy (e.g., treatment including a pan-RAF inhibitor (e.g., a pan-RAF dimer inhibitor) and a MEK or PI3K inhibitor).

The methods described herein may be performed, for example, by utilizing pre-packaged diagnostic kits, such as those described below, comprising at least one probe or primer nucleic acid, which may be conveniently used, e.g., to determine whether a subject is likely to benefit from a treatment including a pan-RAF inhibitor (e.g., a pan-RAF dimer inhibitor) and a MEK or PI3K inhibitor.

Sample nucleic acid for use in the above-described diagnostic methods can be obtained from any cell type or tissue of the individual, including tumor tissue or blood.

In all methods of screening described above or referenced herein, a mutation in one or more RAS genes (e.g., KRAS or NRAS), or a protein product thereof, can generally be identified by determining a nucleic acid sequence (e.g., DNA or RNA sequence) or protein sequence (i.e., amino acid sequence) in a sample obtained from an individual and comparing the sequence to a reference sequence (e.g., a wild-type sequence). In certain instances, a reference level, reference sample, reference cell, reference tissue, control sample, control cell, or control tissue is a single sample or a combination of multiple samples from the same subject or individual that are obtained at one or more different time points than when the test sample is obtained. For example, a reference level, reference sample, reference cell, reference tissue, control sample, control cell, or control tissue is obtained at an earlier time point from the same subject or individual than when the test sample is obtained. Such reference level, reference sample, reference cell, reference tissue, control sample, control cell, or control tissue may be useful if the reference sample is obtained during initial diagnosis of cancer and the test sample is later obtained when the cancer becomes metastatic.

B. Treatment Methods

The present invention provides methods for treating individuals having cancer (e.g., colorectal cancer, ovarian cancer, lung cancer, pancreatic cancer, and skin cancer (e.g., melanoma)) by administering a therapeutically effective amount of pan-RAF inhibitor (e.g., a pan-RAF dimer inhibitor) and a MEK inhibitor or a PI3K inhibitor to the individual based on the presence of a KRAS activating mutation (e.g., a KRAS-G13D mutation). In some instances, the method includes a step of screening a sample (e.g., a tissue sample (e.g., a tumor tissue sample)) from the individual for a KRAS activating mutation, wherein the individual has been determined to have a KRAS activating mutation. In other instances, prior to treatment a sample (e.g., a tissue sample (e.g., a tumor tissue sample)) from the individual has been screened for a KRAS activating mutation and the presence of a KRAS activating mutation has been determined.

In some instances, the invention provides methods for treating an individual having a cancer (e.g., colorectal cancer, ovarian cancer, lung cancer, pancreatic cancer, and skin cancer (e.g., melanoma)) that include (a) screening a sample (e.g., a tissue sample (e.g., a tumor tissue sample)) from the individual for a KRAS-G13D mutation, wherein the individual has been determined to have a KRAS-G13D mutation, and (b) administering a therapeutically effective amount of a pan-RAF inhibitor (e.g., a pan-RAF dimer inhibitor) and a MEK inhibitor to the individual based on the presence of the KRAS-G13D mutation determined by the screening step.

In some instances, the invention provides methods for treating an individual having a cancer (e.g., colorectal cancer, ovarian cancer, lung cancer, pancreatic cancer, and skin cancer (e.g., melanoma)) that include administering to the individual a therapeutically effective amount of a pan-RAF inhibitor (e.g., a pan-RAF dimer inhibitor) and a MEK inhibitor, wherein prior to treatment a sample (e.g., a tissue sample (e.g., a tumor tissue sample)) from the individual has been screened for a KRAS-G13D mutation and the presence of a KRAS-G13D mutation has been determined.

In some instances, the invention provides methods for treating an individual having a cancer (e.g., colorectal cancer, ovarian cancer, lung cancer, pancreatic cancer, and skin cancer (e.g., melanoma)) that include (a) screening a sample (e.g., a tissue sample (e.g., a tumor tissue sample)) from the individual for a KRAS activating mutation (e.g., KRAS-G12D, KRAS-G12C, KRAS-G12V, KRAS-G13D, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, or KRAS-Q61R), wherein the individual has been determined to have a KRAS activating mutation, and (b) administering a therapeutically effective amount of a pan-RAF inhibitor (e.g., a pan-RAF dimer inhibitor) and a PI3K inhibitor to the individual based on the presence of the KRAS activating mutation determined by the screening step. In some instances, the individual does not have a BRAF activating mutation.

In some instances, the invention provides methods for treating an individual having a cancer (e.g., colorectal cancer, ovarian cancer, lung cancer, pancreatic cancer, and skin cancer (e.g., melanoma)) that include administering to the individual a therapeutically effective amount of a pan-RAF inhibitor (e.g., a pan-RAF dimer inhibitor) and a PI3K inhibitor, wherein prior to treatment a sample (e.g., a tissue sample (e.g., a tumor tissue sample)) from the individual has been screened for a KRAS activating mutation (e.g., KRAS-G12D, KRAS-G12C, KRAS-G12V, KRAS-G13D, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, or KRAS-Q61R) and the presence of a KRAS activating mutation has been determined. In some instances, the individual does not have a BRAF activating mutation.

The present invention also provides methods for treating individuals having cancer (e.g., skin cancer (e.g., melanoma), colorectal cancer, ovarian cancer, lung cancer, and pancreatic cancer) by administering a therapeutically effective amount of pan-RAF inhibitor (e.g., a pan-RAF dimer inhibitor) and a MEK inhibitor to the individual based on the presence of an NRAS activating mutation. In some instances, the method includes a step of screening a sample (e.g., a tissue sample (e.g., a tumor tissue sample)) from the individual for an NRAS activating mutation, wherein the individual has been determined to have an NRAS activating mutation. In other instances, prior to treatment a sample (e.g., a tissue sample (e.g., a tumor tissue sample)) from the individual has been screened for an NRAS activating mutation and the presence of an NRAS activating mutation has been determined.

In some instances, the invention provides methods for treating an individual having a cancer (e.g., skin cancer (e.g., melanoma), colorectal cancer, ovarian cancer, lung cancer, and pancreatic cancer) that include (a) screening a sample (e.g., a tissue sample (e.g., a tumor tissue sample)) from the individual for an NRAS activating mutation (e.g., NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, or NRAS-Q61P), wherein the individual has been determined to have an NRAS activating mutation, and (b) administering a therapeutically effective amount of a pan-RAF inhibitor (e.g., a pan-RAF dimer inhibitor) and a MEK inhibitor to the individual based on the presence of the NRAS activating mutation determined by the screening step.

In some instances, the invention provides methods for treating an individual having a cancer (e.g., skin cancer (e.g., melanoma), colorectal cancer, ovarian cancer, lung cancer, and pancreatic cancer) that include administering to the individual a therapeutically effective amount of a pan-RAF inhibitor (e.g., a pan-RAF dimer inhibitor) and a MEK inhibitor, wherein prior to treatment a sample (e.g., a tissue sample (e.g., a tumor tissue sample)) from the individual has been screened for an NRAS activating mutation (e.g., NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, or NRAS-Q61P) and the presence of an NRAS activating mutation has been determined.

For any of the above therapeutic methods, the sample or samples from the individual may be, or have been, screened using any one or more of the methods described above in Section III, Part A.

As also described above, the administered MEK inhibitor may be a small molecule inhibitor, which may be a prodrug or a biologically active form. For example, the MEK inhibitor may be a small molecule inhibitor selected from the group consisting of cobimetinib (GDC-0973), selumetinib (AZD6244), pimasertib (AS-703026), PD0325901, refametinib (BAY86-9766), binimetinib (MEK162), BI-847325, trametinib, GDC-0623, G-573, and CH5126766 (RO5126766), or a pharmaceutically acceptable salt thereof. In particular instances, the small molecule inhibitor is cobimetinib (GDC-0973), selumetinib (AZD6244), pimasertib (AS-703026), PD0325901, refametinib (BAY86-9766), or binimetinib (MEK162), or a pharmaceutically acceptable salt thereof. The administered PI3K inhibitor may be a small molecule inhibitor, which may be a prodrug or a biologically active form. For example, the small molecule inhibitor is selected from the group consisting of pictilisib (GDC-0941), taselisib (GDC-0032), and alpelisib (BYL719), or a pharmaceutically acceptable salt thereof. The PI3K inhibitor may be a pan-PI3K inhibitor (e.g., pictilisib (GDC-0941) or taselisib (GDC-0032), or a pharmaceutically acceptable salt thereof), or a PI3Kα-specific inhibitor and/or PI3Kδ-specific inhibitor. And the administered pan-RAF inhibitor may be a pan-RAF dimer inhibitor. In certain instances, the pan-RAF inhibitor (e.g., pan-RAF dimer inhibitor) may be a small molecule inhibitor, which may be a prodrug or a biologically active form. In certain instances, the pan-RAF dimer inhibitor may be HM95573, LY-3009120, AZ-628, LXH-254, MLN2480, BeiGene-283, RXDX-105, BAL3833, regorafenib, or sorafenib, or a pharmaceutically acceptable salt thereof.

In certain embodiments, the therapeutic method also includes administering to the individual one or more additional therapeutic agents (e.g., immunotherapy agents, cytotoxic agents, growth inhibitory agents, radiation therapy agents, and anti-angiogenic agents).

In any of the above methods, administration of a pan-RAF inhibitor (e.g., a pan-RAF dimer inhibitor) and MEK or PI3K inhibitor can have the therapeutic effect (i.e., benefit) of a cellular or biological response, a complete response, a partial response, a stable disease (without progression or relapse), or a response with a later relapse of the patient as a result of the treatment with a pan-RAF inhibitor in combination with either a MEK inhibitor or a PI3K inhibitor. For example, an effective response can be reduced tumor size (volume), increased progression-free survival (PFS), and/or increased overall survival (OS) in an individual having a KRAS activating mutation (e.g., KRAS-G12D, KRAS-G12C, KRAS-G12V, KRAS-G13D, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, or KRAS-Q61R) or an NRAS activating mutation (e.g., NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, or NRAS-Q61P) compared to an individual without the KRAS activating mutation or NRAS activating mutation. In some instances, administration of a pan-RAF inhibitor (e.g., a pan-RAF dimer inhibitor) and MEK or PI3K inhibitor has a therapeutic effect of a reduction in tumor size (volume) by 1% or more (e.g., 2%, 3%, 4%, 5%, 6%, 7%, 8%, 9% 10%, 20%, 30%, 40%, 50%, 60%, 70%, 80%, or 90% or more). The presence of one or more KRAS activating mutations (e.g., KRAS-G13D) or NRAS activating mutations predicts such therapeutic efficacy. In some instances, administration of a pan-RAF inhibitor (e.g., a pan-RAF dimer inhibitor) and MEK or PI3K inhibitor has the therapeutic effect of increasing progression-free survival (PFS) by 1 day or more (e.g., by 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, or 1 year or more).

Dosage and Administration

Once a patient responsive or sensitive to treatment with a pan-RAF inhibitor in combination with either a MEK inhibitor or a PI3K inhibitor has been identified, treatment with the combination therapy, alone or in conjunction with other therapeutic agents, can be carried out. As noted above, such treatment may result in, for example, a reduction in tumor size or an increase in progression-free survival (PFS) and/or overall survival (OS). Moreover, treatment with the pan-RAF inhibitor in combination with either a MEK inhibitor or a PI3K inhibitor preferably results in a synergistic (or greater than additive) therapeutic benefit to the patient. Preferably, in this combination method the timing between at least one administration of the pan-RAF inhibitor in combination with either a MEK inhibitor or a PI3K inhibitor is about one month or less, and more preferably, about two weeks or less.

It will be appreciated by those of skill in the art that the exact manner of administering a therapeutically effective amount of a pan-RAF inhibitor in combination with either a MEK inhibitor or a PI3K inhibitor to a patient following diagnosis of their likely responsiveness to the combination therapy will be at the discretion of the attending physician. The mode of administration, including dosage, combination with other agents, timing and frequency of administration, and the like, may be affected by the diagnosis of a patient's likely responsiveness to such combination therapy, as well as the patient's condition and history. Thus, even patients having cancers who are predicted to be relatively insensitive to a pan-RAF inhibitor in combination with either a MEK inhibitor or a PI3K inhibitor may still benefit from treatment therewith, particularly in combination with other agents, including agents that may alter a patient's responsiveness to one or both inhibitors.

A composition comprising a pan-RAF inhibitor and either a MEK inhibitor or a PI3K inhibitor will be formulated, dosed, and administered in a fashion consistent with good medical practice. Factors for consideration in this context include the particular type of cancer being treated (e.g., lung cancer, breast cancer, skin cancer, colorectal cancer, stomach cancer, lymphoid cancer, pancreatic cancer, ovarian cancer, and cervical cancer), the particular mammal being treated (e.g., human), the clinical condition of the individual patient, the cause of the cancer, the site of delivery of the agent, possible side-effects, the type of inhibitor, the method of administration, the scheduling of administration, and other factors known to medical practitioners. The effective amount of the pan-RAF inhibitor and MEK or PI3K inhibitor to be administered will be governed by such considerations.

A physician having ordinary skill in the art can readily determine and prescribe the effective amount of the pharmaceutical composition required, depending on such factors as the particular antagonist type. For example, the physician could start with doses of such a pan-RAF inhibitor in combination with either a MEK inhibitor or a PI3K inhibitor, employed in the pharmaceutical composition at levels lower than that required in order to achieve the desired therapeutic effect and gradually increase the dosage until the desired effect is achieved. The effectiveness of a given dose or treatment regimen of the antagonist can be determined, for example, by assessing signs and symptoms in the patient using standard measures of efficacy.

In certain examples, the pan-RAF inhibitor (e.g., pan-RAF dimer inhibitor) may be the only agent administered to the subject (i.e., as a monotherapy), for example, in the instance that the subject has an NRAS activating mutation. In other instances, the pan-RAF inhibitor (e.g., pan-RAF dimer inhibitor) and MEK or PI3K inhibitor may be administered to the subject (i.e., as a combination therapy).

In certain examples, the patient is treated with the same therapy at least twice. Thus, the initial and second exposures are preferably with the same inhibitor or same combination of inhibitors, and more preferably all exposures are with the same inhibitor or same combination of inhibitors, i.e., treatment for the first two exposures, and preferably all exposures, is with the same inhibitor (e.g., the same pan-RAF dimer inhibitor) or same combination of inhibitors (e.g., the same pan-RAF dimer inhibitor and the same MEK or PI3K inhibitor).

Treatment with MAPK signaling inhibitors or PI3K inhibitors, or pharmaceutically acceptable salts thereof, can be carried out according to standard methods. For example, exemplary methods for administration of the MEK inhibitor, cobimetinib (e.g., cobimetinib fumarate (COTELLIC®)), are described in Prescribing Information for cobimetinib fumarate (COTELLIC®) in the United States, Genentech, Inc. (Nov. 10, 2015), which is incorporated herein by reference in its entirety. Exemplary methods for the administration of vemurafenib (ZELBORAF®) are described in Prescribing Information for vemurafenib (ZELBORAF®) in the United States, Hoffmann La Roche, Inc. (Aug. 11, 2015), which is incorporated herein by reference in its entirety.

If multiple exposures of the pan-RAF inhibitor (e.g., pan-RAF dimer inhibitor) and MEK or PI3K inhibitor are provided, each exposure may be provided using the same or a different administration means. In one embodiment, each exposure is given by oral administration. In one embodiment, each exposure is by intravenous administration. In another embodiment, each exposure is given by subcutaneous administration. In yet another embodiment, the exposures are given by both intravenous and subcutaneous administration.

The duration of therapy can be continued for as long as medically indicated or until a desired therapeutic effect (e.g., those described herein) is achieved. In certain embodiments, the therapy is continued for 1 month, 2 months, 4 months, 6 months, 8 months, 10 months, 1 year, 2 years, 3 years, 4 years, 5 years, or for a period of years up to the lifetime of the subject.

As noted above, however, these suggested amounts of the pan-RAF inhibitor (e.g., pan-RAF dimer inhibitor) and MEK or PI3K inhibitor are subject to a great deal of therapeutic discretion. The key factor in selecting an appropriate dose and scheduling is the result obtained, as indicated above. In some embodiments, the pan-RAF inhibitor (e.g., pan-RAF dimer inhibitor) and MEK or PI3K inhibitor is administered as close to the first sign, diagnosis, appearance, or occurrence of the proliferative cell disorder (e.g., cancer) as possible.

Routes of Administration

A pan-RAF inhibitor (e.g., pan-RAF dimer inhibitor) in combination with either a MEK inhibitor or a PI3K inhibitor and, optionally, any additional therapeutic agent(s) may be formulated, dosed, and administered in a fashion consistent with good medical practice. Factors for consideration in this context include the particular disorder being treated (e.g., cancer), the particular mammal being treated, the clinical condition of the individual patient, the cause of the disorder, the site of delivery of the agent, the method of administration, the scheduling of administration, and other factors known to medical practitioners. For example, a pan-RAF inhibitor (e.g., pan-RAF dimer inhibitor) need not be, but is optionally formulated with and/or administered concurrently with, either a MEK inhibitor or a PI3K inhibitor, optionally in further combination with one or more agents currently used to prevent or treat the disorder (e.g., cancer).

For the prevention or treatment of a cancer, the appropriate dosages of a pan-RAF inhibitor (e.g., pan-RAF dimer inhibitor) and MEK or PI3K inhibitor described herein (when used alone or in combination with one or more other additional therapeutic agents) will depend on the type of disease (e.g., cancer) to be treated, the severity and course of the disease, whether the inhibitors are administered for preventive or therapeutic purposes, previous therapy, the patient's clinical history and response to the inhibitors, and the discretion of the attending physician. The pan-RAF inhibitor (e.g., pan-RAF dimer inhibitor) and MEK or PI3K inhibitor are suitably administered to the patient at one time or over a series of treatments. For repeated administrations over several days or longer, depending on the condition, the treatment would generally be sustained until a desired suppression of disease symptoms occurs. Such doses may be administered intermittently, e.g., every week or every three weeks (e.g., such that the patient receives, for example, from about two to about twenty, or e.g., about six doses of the pan-RAF inhibitor (e.g., pan-RAF dimer inhibitor) and MEK or PI3K inhibitor). An initial higher loading dose, followed by one or more lower doses may be administered. However, other dosage regimens may be useful. The progress of this therapy is easily monitored by conventional techniques and assays.

The pan-RAF inhibitor (e.g., pan-RAF dimer inhibitor) and MEK or PI3K inhibitor can be administered by any suitable means, including orally, parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated. In addition, the pan-RAF inhibitor (e.g., pan-RAF dimer inhibitor) and MEK or PI3K inhibitor may suitably be administered by pulse infusion, e.g., with declining doses of one or both inhibitors. Optionally, the dosing is given by oral administration.

If multiple exposures of a pan-RAF inhibitor (e.g., pan-RAF dimer inhibitor) in combination with a MEK or PI3K inhibitor are provided, each exposure may be provided using the same or a different administration means. In another embodiment, each exposure is given intravenously (i.v.). In another embodiment, each exposure is given by subcutaneous (s.c.) administration. In yet another embodiment, the exposures are given by both i.v. and s.c. administration.

Combination Therapy

The therapeutic methods described herein generally include administration of more than one therapeutic agent (e.g., a pan-RAF inhibitor (e.g., pan-RAF dimer inhibitor) in combination with a MEK or PI3K inhibitor).

The combination therapy may provide "synergy" and prove "synergistic," i.e., the effect achieved when the active ingredients are used together is greater than the sum of the effects that results from using the compounds separately. A synergistic effect may be attained when the active ingredients (i.e., pan-RAF inhibitor (e.g., pan-RAF dimer inhibitor) and MEK or PI3K inhibitor) are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially. In general, during alternation therapy, an effective dosage of each active ingredient is administered sequentially (i.e., serially), whereas in combination therapy, effective dosages of two or more active ingredients are administered together.

In some instances, the method includes further administering an anti-cancer agent, such as a chemotherapeutic agent, a growth-inhibitory agent, a biotherapy, an immunotherapy, or a radiation therapy agent. In addition, cytotoxic agents, anti-angiogenic, and anti-proliferative agents can be used in combination with the pan-RAF inhibitor (e.g., pan-RAF dimer inhibitor) and MEK or PI3K inhibitor. In some instances, the pan-RAF inhibitor (e.g., pan-RAF dimer inhibitor) and MEK or PI3K inhibitor is used in combination with an anti-cancer therapy, such as surgery.

In other instances, the therapeutic methods may include administering a combination of two or more (e.g., three or more) MAPK signaling inhibitors (e.g., two or more RAF, MEK, or ERK inhibitors) and/or PI3K inhibitors.

The methods may also involve administering to the patient an effective amount of a pan-RAF inhibitor (e.g., pan-RAF dimer inhibitor) and MEK or PI3K inhibitor, in combination with a chemotherapeutic agent, such as docetaxel, doxorubicin, and cyclophosphamide.

In other instances, the method includes administering a pan-RAF inhibitor (e.g., pan-RAF dimer inhibitor) and MEK or PI3K inhibitor, in combination with an immunotherapeutic, such as a therapeutic antibody. In one embodiment, the therapeutic antibody is an antibody that binds a cancer cell surface marker or tumor associated-antigen (TAA). In one embodiment, the therapeutic antibody is an anti-HER2 antibody, trastuzumab (e.g., HERCEPTIN®). In one embodiment, the therapeutic antibody is an anti-HER2 antibody, pertuzumab (OMNITARG™). In another embodiment, the therapeutic antibody either a naked antibody or an antibody-drug conjugate (ADC).

Without wishing to be bound to theory, it is thought that enhancing T-cell stimulation, by promoting an activating co-stimulatory molecule or by inhibiting a negative co-stimulatory molecule, may promote tumor cell death thereby treating or delaying progression of cancer. Therefore, in some instances, a pan-RAF inhibitor (e.g., pan-RAF dimer inhibitor) and MEK or PI3K inhibitor may be administered in conjunction with an agonist directed against an activating co-stimulatory molecule. In some instances, an activating co-stimulatory molecule may include CD40, CD226, CD28, OX40, GITR, CD137, CD27, HVEM, or CD127. In some instances, the agonist directed against an activating co-stimulatory molecule is an agonist antibody that binds to CD40, CD226, CD28, OX40, GITR, CD137, CD27, HVEM, or CD127. In some instances, a pan-RAF inhibitor (e.g., pan-RAF dimer inhibitor) and MEK or PI3K inhibitor may be administered in conjunction with an antagonist directed against an inhibitory co-stimulatory molecule. In some instances, an inhibitory co-stimulatory molecule may include CTLA-4 (also known as CD152), TIM-3, BTLA, VISTA, LAG-3, B7-H3, B7-H4, IDO, TIGIT, MICA/B, or arginase. In some instances, the antagonist directed against an inhibitory co-stimulatory molecule is an antagonist antibody that binds to CTLA-4, TIM-3, BTLA, VISTA, LAG-3, B7-H3, B7-H4, IDO, TIGIT, MICA/B, or arginase.

In some instances, a pan-RAF inhibitor (e.g., pan-RAF dimer inhibitor) and MEK or PI3K inhibitor may be administered in conjunction with an antagonist directed against CTLA-4 (also known as CD152), e.g., a blocking antibody. In some instances, a pan-RAF inhibitor (e.g., pan-RAF dimer inhibitor) and MEK or PI3K inhibitor may be administered in conjunction with ipilimumab (also known as MDX-010, MDX-101, or YERVOY®). In some instances, a pan-RAF inhibitor (e.g., pan-RAF dimer inhibitor) and MEK or PI3K inhibitor may be administered in conjunction with tremelimumab (also known as ticilimumab or CP-675, 206). In some instances, a pan-RAF inhibitor (e.g., pan-RAF dimer inhibitor) and MEK or PI3K inhibitor may be administered in conjunction with an antagonist directed against B7-H3 (also known as CD276), e.g., a blocking antibody. In some instances, a pan-RAF inhibitor (e.g., pan-RAF dimer inhibitor) and MEK or PI3K inhibitor may be administered in conjunction with MGA271. In some instances, a pan-RAF inhibitor (e.g., pan-RAF dimer inhibitor) and MEK or PI3K inhibitor may be administered in conjunction with an antagonist directed against a TGF-β, e.g., metelimumab (also known as CAT-192), fresolimumab (also known as GC1008), or LY2157299.

In some instances, a pan-RAF inhibitor (e.g., pan-RAF dimer inhibitor) and MEK or PI3K inhibitor may be administered in conjunction with a treatment including adoptive transfer of a T cell (e.g., a cytotoxic T cell or cytotoxic lymphocyte (CTL)) expressing a chimeric antigen receptor (CAR). In some instances, a pan-RAF inhibitor (e.g., pan-RAF dimer inhibitor) and MEK or PI3K inhibitor may be administered in conjunction with a treatment including adoptive transfer of a T cell including a dominant-negative TGF-β receptor, e.g., a dominant-negative TGF-β type II receptor. In some instances, a pan-RAF inhibitor (e.g., pan-RAF dimer inhibitor) and MEK or PI3K inhibitor may be administered in conjunction with a treatment including a HERCREEM protocol (see, e.g., ClinicalTrials.gov Identifier NCT00889954).

In some instances, a pan-RAF inhibitor (e.g., pan-RAF dimer inhibitor) and MEK or PI3K inhibitor may be administered in conjunction with an agonist directed against CD137 (also known as TNFRSF9, 4-1BB, or ILA), e.g., an activating antibody. In some instances, a pan-RAF inhibitor (e.g., pan-RAF dimer inhibitor) and MEK or PI3K inhibitor may be administered in conjunction with urelumab (also known as BMS-663513). In some instances, a pan-RAF inhibitor (e.g., pan-RAF dimer inhibitor) and MEK or PI3K inhibitor may be administered in conjunction with an agonist directed against CD40, e.g., an activating antibody. In some instances, a pan-RAF inhibitor (e.g., pan-RAF dimer inhibitor) and MEK or PI3K inhibitor may be administered in conjunction with CP-870893. In some instances, a pan-RAF inhibitor (e.g., pan-RAF dimer inhibitor) and MEK or PI3K inhibitor may be administered in conjunction with an agonist directed against OX40 (also known as CD134), e.g., an activating antibody. In some instances, a pan-RAF inhibitor (e.g., pan-RAF dimer inhibitor) and MEK or PI3K inhibitor may be administered in conjunction with an anti-OX40 antibody (e.g., AgonOX). In some instances, a pan-RAF inhibitor (e.g., pan-RAF dimer inhibitor) and MEK or PI3K inhibitor may be administered in conjunction with an agonist directed against CD27, e.g., an activating antibody. In some instances, a pan-RAF inhibitor (e.g., pan-RAF dimer inhibitor) and MEK or PI3K inhibitor may be administered in conjunction with CDX-1127. In some instances, a pan-RAF inhibitor (e.g., pan-RAF dimer inhibitor) and MEK or PI3K inhibitor may be administered in conjunction with an antagonist directed against indoleamine-2,3-dioxygenase (IDO). In some instances, with the IDO antagonist is 1-methyl-D-tryptophan (also known as 1-D-MT). In some instances, a pan-RAF inhibitor (e.g., pan-RAF dimer inhibitor) and MEK or PI3K inhibitor may be administered in conjugation with a PD-1 axis binding antagonist. In some instances, the PD-1 axis binding antagonist is a PD-L1 antibody.

In some instances, a pan-RAF inhibitor (e.g., pan-RAF dimer inhibitor) and MEK or PI3K inhibitor may be administered in conjunction with an antibody-drug conjugate. In some instances, the antibody-drug conjugate comprises mertansine or monomethyl auristatin E (MMAE). In some instances, a pan-RAF inhibitor (e.g., pan-RAF dimer inhibitor) and MEK or PI3K inhibitor may be administered in conjunction with an anti-NaPi2b antibody-MMAE conjugate (also known as DNIB0600A or RG7599). In some instances, a pan-RAF inhibitor (e.g., pan-RAF dimer inhibitor) and MEK or PI3K inhibitor may be administered in conjunction with trastuzumab emtansine (also known as T-DM1, ado-trastuzumab emtansine, or KADCYLA®, Genentech). In some instances, a pan-RAF inhibitor (e.g., pan-RAF dimer inhibitor) and MEK or PI3K inhibitor may be administered in conjunction with DMUC5754A. In some instances, a pan-RAF inhibitor (e.g., pan-RAF dimer inhibitor) and MEK or PI3K inhibitor may be administered in conjunction with an antibody-drug conjugate targeting the endothelin B receptor (EDNBR), e.g., an antibody directed against EDNBR conjugated with MMAE.

In some instances, a pan-RAF inhibitor (e.g., pan-RAF dimer inhibitor) and MEK or PI3K inhibitor may be administered in conjunction with an anti-angiogenesis agent. In some instances, a pan-RAF inhibitor (e.g., pan-RAF dimer inhibitor) and MEK or PI3K inhibitor may be administered in conjunction with an antibody directed against a VEGF, e.g., VEGF-A. In some instances, a pan-RAF inhibitor (e.g., pan-RAF dimer inhibitor) and MEK or PI3K inhibitor may be administered in conjunction with bevacizumab (also known as AVASTIN®, Genentech). In some instances, a pan-RAF inhibitor (e.g., pan-RAF dimer inhibitor) and MEK or PI3K inhibitor may be administered in conjunction with an antibody directed against angiopoietin 2 (also known as Ang2). In some instances, a pan-RAF inhibitor (e.g., pan-RAF dimer inhibitor) and MEK or PI3K inhibitor may be administered in conjunction with MEDI3617. In some instances, a pan-RAF inhibitor (e.g., pan-RAF dimer inhibitor) and MEK or PI3K inhibitor may be administered in conjunction with an antineoplastic agent. In some instances, a pan-RAF inhibitor (e.g., pan-RAF dimer inhibitor) and MEK or PI3K inhibitor may be administered in conjunction with an agent targeting CSF-1R (also known as M-CSFR or CD115). In some instances, a pan-RAF inhibitor (e.g., pan-RAF dimer inhibitor) and MEK or PI3K inhibitor may be administered in conjunction with anti-CSF-1R (also known as IMC-CS4). In some instances, a pan-RAF inhibitor (e.g., pan-RAF dimer inhibitor) and MEK or PI3K inhibitor may be administered in conjunction with an interferon, for example interferon alpha or interferon gamma. In some instances, a pan-RAF inhibitor (e.g., pan-RAF dimer inhibitor) and MEK or PI3K inhibitor may be administered in conjunction with Roferon-A (also known as recombinant Interferon alpha-2a). In some instances, a pan-RAF inhibitor (e.g., pan-RAF dimer inhibitor) and MEK or PI3K inhibitor may be administered in conjunction with GM-CSF (also known as recombinant human granulocyte macrophage colony stimulating factor, rhu GM-CSF, sargramostim, or LEUKINE®). In some instances, a pan-RAF inhibitor (e.g., pan-RAF dimer inhibitor) and MEK or PI3K inhibitor may be administered in conjunction with IL-2 (also known as aldesleukin or PROLEUKIN®). In some instances, a pan-RAF inhibitor (e.g., pan-RAF dimer inhibitor) and MEK or PI3K inhibitor may be administered in conjunction with IL-12. In some instances, a pan-RAF inhibitor (e.g., pan-RAF dimer inhibitor) and MEK or PI3K inhibitor may be administered in conjunction with an antibody targeting CD20. In some instances, the antibody targeting CD20 is obinutuzumab (also known as GA101 or GAZYVA®) or rituximab. In some instances, a pan-RAF inhibitor (e.g., pan-RAF dimer inhibitor) and MEK or PI3K inhibitor may be administered in conjunction with an antibody targeting GITR. In some instances, the antibody targeting GITR is TRX518.

In some instances, a pan-RAF inhibitor (e.g., pan-RAF dimer inhibitor) and MEK or PI3K inhibitor may be administered in conjunction with a cancer vaccine. In some instances, the cancer vaccine is a peptide cancer vaccine, which in some instances is a personalized peptide vaccine. In some instances the peptide cancer vaccine is a multivalent long peptide, a multi-peptide, a peptide cocktail, a hybrid peptide, or a peptide-pulsed dendritic cell vaccine (see, e.g., Yamada et al., *Cancer Sci.* 104:14-21, 2013). In some instances, a pan-RAF inhibitor (e.g., pan-RAF dimer inhibitor) and MEK or PI3K inhibitor may be administered in conjunction with an adjuvant. In some instances, a pan-RAF inhibitor (e.g., pan-RAF dimer inhibitor) and MEK or PI3K inhibitor may be administered in conjunction with a treatment including a TLR agonist, e.g., Poly-ICLC (also known as HILTONOL®), LPS, MPL, or CpG ODN. In some instances, a pan-RAF inhibitor (e.g., pan-RAF dimer inhibitor) and MEK or PI3K inhibitor may be administered in conjunction with tumor necrosis factor (TNF) alpha. In some instances, a pan-RAF inhibitor (e.g., pan-RAF dimer inhibitor) and MEK or PI3K inhibitor may be administered in conjunction with IL-1, e.g., IL-1β. In some instances, a pan-RAF inhibitor (e.g., pan-RAF dimer inhibitor) and MEK or PI3K inhibitor may be administered in conjunction with HMGB1. In some instances, a pan-RAF inhibitor (e.g., pan-RAF dimer inhibitor) and MEK or PI3K inhibitor may be administered in conjunction with an IL-10 antagonist. In some instances, a pan-RAF inhibitor (e.g., pan-RAF dimer inhibitor) and MEK or PI3K inhibitor may be administered in conjunction with an IL-4 antagonist. In some instances, a pan-RAF inhibitor (e.g., pan-RAF dimer inhibitor) and MEK or PI3K inhibitor may be administered in conjunction with an IL-13 antagonist. In some instances, a pan-RAF inhibitor (e.g., pan-RAF dimer inhibitor) and MEK or PI3K inhibitor may be administered in conjunction with an HVEM antagonist. In some instances, a pan-RAF inhibitor (e.g., pan-RAF dimer inhibitor) and MEK or PI3K inhibitor may be administered in conjunction with an ICOS agonist, e.g., by administration of ICOS-L, or an agonistic antibody directed against ICOS. In some instances, a pan-RAF inhibitor (e.g., pan-RAF dimer inhibitor) and MEK or PI3K inhibitor may be administered in conjunction with a treatment targeting CX3CL1. In some instances, a pan-RAF inhibitor (e.g., pan-RAF dimer inhibitor) and MEK or PI3K inhibitor may be administered in conjunction with a treatment targeting CXCL9. In some instances, a pan-RAF inhibitor (e.g., pan-RAF dimer inhibitor) and MEK or PI3K inhibitor may be administered in conjunction with a treatment targeting CXCL10. In some instances, a pan-RAF inhibitor (e.g., pan-RAF dimer inhibitor) and MEK or PI3K inhibitor may be administered in conjunction with a treatment targeting CCL5. In some instances, a pan-RAF inhibitor (e.g., pan-RAF dimer inhibitor) and MEK or PI3K inhibitor may be administered in conjunction with an LFA-1 or ICAM1 agonist. In some instances, a pan-RAF inhibitor (e.g., pan-RAF dimer inhibitor) and MEK or PI3K inhibitor may be administered in conjunction with a selectin agonist.

In general, for the prevention or treatment of disease, the pan-RAF inhibitor (e.g., pan-RAF dimer inhibitor) and MEK or PI3K inhibitor are suitably administered to the patient at one time or over a series of treatments. The pan-RAF inhibitor (e.g., pan-RAF dimer inhibitor) and MEK or PI3K inhibitor are typically administered as set forth above. Depending on the type and severity of the disease, about 20 mg/m$^2$ to 600 mg/m$^2$ of an additional therapeutic agent is an initial candidate dosage for administration to the patient, whether, for example, by one or more separate administrations, or by continuous infusion. One typical daily dosage for any therapeutic agent in the treatment regimen might range from about or about 20 mg/m$^2$, 85 mg/m$^2$, 90 mg/m$^2$, 125 mg/m$^2$, 200 mg/m$^2$, 400 mg/m$^2$, 500 mg/m$^2$ or more, depending on the factors mentioned above. For repeated administrations over several days or longer, depending on the condition, the treatment is sustained until a desired suppression of disease symptoms occurs. Thus, one or more doses of about 20 mg/m$^2$, 85 mg/m$^2$, 90 mg/m$^2$, 125 mg/m$^2$, 200 mg/m$^2$, 400 mg/m$^2$, 500 mg/m$^2$, 600 mg/m$^2$ (or any combination thereof) may be administered to the patient. Such doses may be administered intermittently, e.g., every week or every two, three, four, five, or six weeks (e.g., such that the patient receives from about two to about twenty, e.g., about six doses of the additional agent). An initial higher loading dose, followed by one or more lower doses may be administered. However, other dosage regimens may be useful. The progress of this therapy is easily monitored by conventional techniques and assays.

In one embodiment, the subject has never been previously administered any drug(s) to treat cancer. In another embodiment, the subject or patient have been previously administered one or more medicaments(s) to treat cancer. In a further embodiment, the subject or patient was not responsive to one or more of the medicaments that had been previously administered. Such drugs to which the subject may be non-responsive include, for example, anti-neoplastic agents, chemotherapeutic agents, cytotoxic agents, and/or growth inhibitory agents.

IV. Compositions and Uses Thereof

The invention is based, in part, on the discovery that combinations including a pan-RAF inhibitor (e.g., pan-RAF dimer inhibitor) and a MEK inhibitor or a PI3K inhibitor are useful for treating individuals suffering from cancer who have a KRAS activating mutation (e.g., a KRAS-G12D, KRAS-G12C, KRAS-G12V, KRAS-G13D, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, or KRAS-Q61R mutation) or an NRAS activating mutation (e.g., NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, or NRAS-Q61P).

In some instances, the invention therefore provides a composition including a pan-RAF inhibitor (e.g., pan-RAF dimer inhibitor) and a MEK inhibitor for use in a method of treating an individual having a cancer (e.g., colorectal cancer, ovarian cancer, lung cancer, pancreatic cancer, and skin cancer (e.g., melanoma)), wherein a sample from the individual has been screened for a KRAS-G13D and the presence of a KRAS-G13D mutation in the sample has been determined. In some instances, the invention provides a composition including a pan-RAF inhibitor (e.g., pan-RAF dimer inhibitor) and a MEK inhibitor for use in the therapeutic treatment of a cancer (e.g., colorectal cancer, ovarian cancer, lung cancer, pancreatic cancer, and skin cancer (e.g., melanoma)) characterized by a KRAS-G13D mutation. In some instances, the invention provides the use of a composition including a pan-RAF dimer inhibitor and a MEK inhibitor for the preparation of a medicament for the therapeutic treatment of a cancer (e.g., colorectal cancer, ovarian cancer, lung cancer, pancreatic cancer, and skin cancer (e.g., melanoma)) characterized by a KRAS-G13D mutation.

In some instances, the invention provides a composition including a pan-RAF inhibitor (e.g., pan-RAF dimer inhibitor) and a MEK inhibitor for use in a method of treating an individual having a cancer (e.g., colorectal cancer, ovarian cancer, lung cancer, pancreatic cancer, and skin cancer (e.g., melanoma)), wherein a sample from the individual has been screened for an NRAS activating mutation and the presence of an NRAS activating mutation in the sample has been determined. In some instances, the invention provides a composition including a pan-RAF dimer inhibitor and a MEK inhibitor for use in the therapeutic treatment of a cancer (e.g., colorectal cancer, ovarian cancer, lung cancer, pancreatic cancer, and skin cancer (e.g., melanoma)) characterized by an NRAS activating mutation. In some instances, the invention provides the use of a composition including a pan-RAF dimer inhibitor and a MEK inhibitor for the preparation of a medicament for the therapeutic treatment of a cancer (e.g., colorectal cancer, ovarian cancer, lung cancer, pancreatic cancer, and skin cancer (e.g., melanoma)) characterized by an NRAS activating mutation.

In other instances, the invention provides a composition including a pan-RAF inhibitor (e.g., pan-RAF dimer inhibitor) and a PI3K inhibitor (e.g., a pan-PI3K inhibitor (e.g., pictilisib (GDC-0941) or taselisib (GDC-0032), or a pharmaceutically acceptable salt thereof), or a PI3Kα-specific inhibitor and/or PI3Kδ-specific inhibitor) for use in a method of treating an individual having a cancer (e.g., colorectal cancer, ovarian cancer, lung cancer, pancreatic cancer, and skin cancer (e.g., melanoma)), wherein a sample from the individual has been screened for a KRAS activating mutation (e.g., a KRAS-G12D, KRAS-G12C, KRAS-G12V, KRAS-G13D, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, or KRAS-Q61R mutation) and the presence of a KRAS activating mutation in the sample has been determined. In some instances, the invention provides a composition including a pan-RAF dimer inhibitor and a PI3K inhibitor for use in the therapeutic treatment of a cancer characterized by a KRAS activating mutation. In some instances, the invention provides the use of a composition including a pan-RAF dimer inhibitor and a PI3K inhibitor for the preparation of a medicament for the therapeutic treatment of a cancer characterized by a KRAS activating mutation.

Also provided are compositions including a RAF inhibitor (e.g., pan-RAF dimer inhibitor) and PI3K inhibitor (e.g., a pan-PI3K inhibitor (e.g., pictilisib (GDC-0941) or taselisib (GDC-0032), or a pharmaceutically acceptable salt thereof), or a PI3Kα-specific inhibitor and/or PI3Kδ-specific inhibitor). In some instances, the invention provides a composition wherein the pan-PI3K inhibitor is pictilisib (GDC-0941) or taselisib (GDC-0032), or a pharmaceutically acceptable salt thereof. In some instances, the invention provides a composition wherein the pan-RAF dimer inhibitor is selected from the group consisting of HM95573, LY-3009120, AZ-628, LXH-254, MLN2480, BeiGene-283, RXDX-105, BAL3833, regorafenib, and sorafenib, or a pharmaceutically acceptable salt thereof. In some instances, the composition comprises a combination selected from the group consisting of HM95573 and pictilisib (GDC-0941), LY-3009120 and pictilisib (GDC-0941), AZ-628 and pictilisib (GDC-0941), LXH-254 and pictilisib (GDC-0941), MLN2480 and pictilisib (GDC-0941), BeiGene-283 and pictilisib (GDC-0941), RXDX-105 and pictilisib (GDC-0941), BAL3833 and pictilisib (GDC-0941), regorafenib and pictilisib (GDC-0941), sorafenib and pictilisib (GDC-0941), HM95573 and taselisib (GDC-0032), LY-3009120 and taselisib (GDC-0032), AZ-628 and taselisib (GDC-0032), LXH-254 and taselisib (GDC-0032), MLN2480 and taselisib (GDC-0032), BeiGene-283 and taselisib (GDC-0032), RXDX-105 and taselisib (GDC-0032), BAL3833 and taselisib (GDC-0032), regorafenib and taselisib (GDC-0032), and sorafenib and taselisib (GDC-0032), or a pharmaceutically acceptable salt thereof.

In some instances, the invention provides pharmaceutical composition comprising a composition described hereinabove.

In some instances, the invention provides a composition, such as a composition described herein hereinabove, for use in the therapeutic treatment of a cancer.

In some instances, the invention provides the use of a composition described herein hereinabove for the preparation of a medicament for the therapeutic treatment of a cancer.

In any of the above instances, the cancer may be selected from the group consisting of a colorectal cancer, an ovarian cancer, a lung cancer, a pancreatic cancer, a skin cancer, a kidney cancer, a bladder cancer, a breast cancer, a gastric carcinoma, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, a mycosis fungoides, a Merkel cell cancer, and a hematologic malignancy.

V. Diagnostic Kits

Provided herein are diagnostic kits including one or more reagents (e.g., polypeptides or polynucleotides) for determining the presence of a biomarker (e.g., a KRAS activating mutation (e.g., a KRAS-G12D, KRAS-G12C, KRAS-G12V, KRAS-G13D, KRAS-G12A, KRAS-G12R, KRAS-G12S, KRAS-G13C, KRAS-G13A, KRAS-G13R, KRAS-G13S, KRAS-G13V, KRAS-Q61H, KRAS-Q61K, KRAS-Q61E, KRAS-Q61L, KRAS-Q61P, or KRAS-Q61R mutation) or an NRAS activating mutation (e.g., NRAS-Q61R, NRAS-Q61K, NRAS-G12D, NRAS-G13D, NRAS-G12S, NRAS-G12C, NRAS-G12V, NRAS-G12A, NRAS-G12R, NRAS-G13C, NRAS-G13A, NRAS-G13R, NRAS-G13S, NRAS-G13V, NRAS-Q61H, NRAS-Q61E, NRAS-Q61L, or NRAS-Q61P)) in a sample from an individual or patient with a disease or disorder (e.g., a proliferative cell disorder (e.g., cancer (e.g., colorectal cancer, ovarian cancer, lung cancer, pancreatic cancer, and skin cancer (e.g., melanoma))).

In some instances, the presence of a biomarker in the sample indicates a higher likelihood of efficacy when the individual is treated with a pan-RAF inhibitor (e.g., pan-RAF dimer inhibitor) in combination with a MEK inhibitor or a PI3K inhibitor. Optionally, the kit may further include instructions for using the reagents to identify an individual having a cancer who may benefit from a treatment comprising a pan-RAF dimer inhibitor and a MEK or PI3K inhibitor.

In some instances, for example, the invention features a kit for identifying an individual having a cancer who may benefit from a treatment comprising a pan-RAF dimer inhibitor and a MEK inhibitor, the kit including reagents for determining the presence of a KRAS-G13D mutation in a sample from the individual, and, optionally, instructions for using the reagents to identify an individual having a cancer who may benefit from a treatment comprising a pan-RAF dimer inhibitor and a MEK inhibitor. In some instances, the reagents include a first oligonucleotide and a second oligonucleotide for use in amplifying all or a portion of the KRAS gene.

In some instances, for example, the invention features a kit for identifying an individual having a cancer who may benefit from a treatment comprising a pan-RAF dimer inhibitor and a MEK inhibitor, the kit including reagents for determining the presence of an NRAS activating mutation in a sample from the individual, and, optionally, instructions for using the reagents to identify an individual having a cancer who may benefit from a treatment comprising a pan-RAF dimer inhibitor and a MEK inhibitor. In some instances, the reagents include a first oligonucleotide and a second oligonucleotide for use in amplifying all or a portion of the NRAS gene.

In some instances, for example, the invention features a kit for identifying an individual having a cancer who may benefit from a treatment comprising a pan-RAF dimer inhibitor and a PI3K inhibitor, the kit including reagents for determining the presence of a KRAS activating mutation in a sample from the individual, and, optionally, instructions for using the reagents to identify an individual having a cancer who may benefit from a treatment comprising a pan-RAF dimer inhibitor and a PI3K inhibitor. In some instances, the reagents include a first oligonucleotide and a second oligonucleotide for use in amplifying all or a portion of the KRAS gene.

EXAMPLES

The following examples are provided to illustrate, but not to limit the presently claimed invention.

Example 1

Materials and Methods

In Vitro Methods
Cell Lines and Reagents

Anti-BRAF (sc-5284) and anti-CRAF (sc-133) antibodies were purchased from Santa Cruz Biotechnology. Anti-MEK1 (610122) and anti-CRAF (610152) antibodies were purchased from BD Biosciences. Anti-pMEK (S217/S221) (9121), anti-ERK (9107), anti-pERK (T202/Y204) (9101), anti-pCRAF (S338) (9427), anti-pEGFR (Y1068) (3777), AKT (9272), pAKT (T308) (13038), cleaved PARP (9521), and anti-β-Actin (4970) were purchased from Cell Signaling Technology. IR-conjugated secondary antibodies goat anti-Mouse 680LT (926-68020), goat anti-Human 680LT (926-68032), and goat anti-Rabbit 800CW (926-32211) were purchased from Li-Cor. All Western blots were scanned on a Li-Cor CLX using duplexed IR-conjugated secondary antibodies. All cells lines were obtained from the American Type Culture Collection (ATCC) and maintained in the recommended media and supplemented with 10% heat-inactivated FBS (HyClone, SH3007003HI), 1×GlutaMAX (Gibco, 35050-061), and 1×Pen Strep (Gibco, 15140-122). A549 shCRAF and HCT116 shCRAF cell lines were generated at Genentech.

Stable Cell Line Generation

HCT116 colon cancer cell line was purchased from ATCC (American Type Culture Collection, Manassas, VA). HCT116 cells were cultured in RPMI 1640 containing 10% fetal bovine serum. HCT116 cells stably expressing luciferase and CRAF shRNA were made with hairpin oligonucleotides (Luciferase shRNA: Sense: 5'-GAT CCC CCT TAC GCT GAG TAC TTC GAT TCA AGA GAT CGA AGT ACT CAG CGT AAG TTT TTT GGA AA-3' (SEQ ID NO: 1), Antisense: 5'-AGC TTT TCC AAA AAA CTT ACG CTG AGT ACT TCG ATC TCT TGA ATC GAA GTA CTC AGC GTA AGG GG-3' (SEQ ID NO: 2) and CRAF shRNA: Sense: 5'-GAT CCC CGA CAT GAA ATC CAA CAA TAT TCA AGA GAT ATT GTT GGA TTT CAT GTC TTT TTT GGA AA-3' (SEQ ID NO: 3), Antisense: 5'-AGC TTT TCC AAA AAA GAC ATG AAA TCC AAC AAT ATC TCT TGA ATA TTG TTG GAT TTC ATG TCG GG-3' (SEQ ID NO: 4)). Inducible-shRNA bearing lentivirus constructs were made based on previously described methods (Gray et al. *BMC Biotechnol.* 7:61, 2007; Jaiswal et al. *PLoS One.* 4: e5717, 2009) by co-transfecting pHUSH-Lenti-puro constructs containing either Luciferase or CRAF shRNA with plasmids expressing the vesicular stomatitis virus (VSV-G) envelope glycoprotein and HIV-1 packaging proteins (GAG-POL) in HEK293T cells using Lipofectamine (Invitrogen, Carlsbad, CA). Target cells were transduced with these viruses and then selected in puromycin. Cells were characterized for knockdown by western blot analysis following induction of shRNAs using media containing 500 ng/ml doxycycline (Clontech, CA) as previously described (Jaiswal et al. *PLoS One.* 4: e5717, 2009).

A549 lung cancer cell line was obtained from ATCC. Cells were cultured in RPMI 1640+10% Fetal Bovine Serum. A549 cells stably expressing non-targeting control (NTC) or CRAF shRNA were made using hairpin oligonucleotides: NTC shRNA targeting sequence: 5' TCC TGC GTC TAG AGG TTC CCA 3' (SEQ ID NO: 5) and CRAF shRNA targeting sequence: 5' TAG GAG TAG ACA TCC GAC TGG 3' (SEQ ID NO: 6). The vector used was pINDUCER 10, which was modified to express optimized miR-30 based hairpins (Meerbrey et al. *PNAS.* 108(9): 3665-3670, 2011; Fellmann et al. *Cell Rep.* 5: 1704-1713, 2013). Inducible-shRNA bearing lentivirus constructs were made by co-transfecting pINDUCER10-miRE constructs containing either NTC or CRAF shRNA with plasmids expressing the vesicular stomatitis virus (VSV-G) envelope glycoprotein and HIV-1 packaging proteins (GAG-POL) in 293T cells with lipofectamine 2000 (Invitrogen). Viral supernatants were concentrated using Lenti-X concentrator (Clontech). Target cells were transduced with these viral supernatants and selected with puromycin (2 μg/ml). Cells were evaluated for knockdown by Western blot analysis after induction of shRNA using media containing 2 μg/ml doxycycline (Sigma).

Cell Viability Assays
RAS Mutant, BRAF Mutant Cell Screens

Seeding densities were optimized for each cell line to obtain 70-80% confluence after 4 days. The cells were plated into 384-well plates (Griener, 781091) and then treated with compound the following day in a final DMSO concentration of 0.1%. The relative numbers of viable cells were measured by luminescence using CellTiter-Glo (Promega, G7573). Viability curves were generated using a four-parameter fit in GraphPad Prism 6.

Tool Compound Combination Screen

A compound library comprising 480 compounds arrayed in 9-point dose response was screened in the absence or presence of a fixed dose of either AZ-628 or DMSO in A549 cells. A549 cells were seeded into 384 well plates, and compound was added 24 h later. Cell viability was determined 120 h post-compound addition (CellTiter Glo). Curves were fitted, and both IC50 and mean viability metrics were calculated. The IC50 is the dose at which inhibition is 50% relative to untreated wells. The mean viability is the average of the fitted viabilities at each tested dose. Mean viability is equivalent to the area under the log-dose/viability curve divided by the total number of tested doses. All data were fitted using Genedata Screener (GDS) software. The combination metric was the difference in mean viability between the AZ-628 treated arm and the DMSO treated arm for each compound.

High-Throughput Cell Viability Assay

Compounds were screened in nine-point dose response using a three-fold dilution. Cells were seeded into 384-well plates 24 hours prior to compound addition. Cells were then incubated with compound for 72 hours or 120 hours before assaying viability (CellTiter-Glo, Promega). Assays were performed in biological triplicate. Cells were incubated (37° C., 5% CO2) in RPMI-1640, 2.5% FBS (72 hour assay) or 5% FBS (120 hour assay), and 2 mM glutamine throughout the assay. The reported IC50 and mean viability metrics are as follows: IC50 is the dose at which the estimated inhibition is 50% relative to untreated wells (i.e., absolute IC50). Mean viability is equivalent to the area under the log-dose/viability curve divided by the total number of tested doses.

Phospho (Ser 217/221)/Total MEK1/2 Assay

Cells were plated at a density of 20,000 cells per 96-well and treated with compound the following day for two hours in a final concentration of 0.2% DMSO. After two hours, the cells were lysed according to manufacturer's protocol (Meso Scale Discovery, K15129D), and the lysates were added to BSA-blocked plates for overnight capture at 4° C. The following day the assay plates were washed three times with TBST and the detection antibody was added for one hour at RT. The plates were then washed three times with TBST. 1× read buffer was added to the plate and immediately read on the Meso Scale Discovery SECTOR Imager 6000. Curves were generated using Graph Pad Prism 6.

Drug Combination Assays

For combination synergy studies, cells were plated in 384-well plates (Corning) and treated with varying concentrations of compound, either alone or in combination for 72 hours. Cell viability was determined using CellTiter-Glo Luminescent Cell Viability Assay (Promega, G7573). Synergistic effects were determined using the Bliss independence analysis methods (Greco et al. *Pharmacol. Rev.* 47: 331-385, 1995; Chou and Talalay. *Adv. Enzyme Regul.* 22:27-55, 1984; Chou. *Cancer Res.* 70: 440-446, 2010; Bliss. *Ann. Appl. Biol.* 25: 31, 1939).

RNA Sequencing Experiment

Cells were seeded overnight and treated with AZ-628 and cobimetinib either singly (0.1 µM) or in combination (0.1 µM each) for 6 hours. Control cells were treated with DMSO (0.2% final concentration). Total RNA was extracted as per manufacturer's protocol using RNEasy mini kits with on-column DNAse digestion (Qiagen #74106 and #79254). Quality control of samples was done to determine RNA quantity and quality prior to their processing by RNA-seq. The concentration of RNA samples was determined using NanoDrop 8000 (Thermo Scientific) and the integrity of RNA was determined by Fragment Analyzer (Advanced Analytical Technologies). 0.5 µg of total RNA was used as an input material for library preparation using TruSeq RNA Sample Preparation Kit v2 (Illumina). Size of the libraries was confirmed using 2200 TapeStation and High Sensitivity D1000 screen tape (Agilent Technologies) and their concentration was determined by qPCR based method using Library quantification kit (KAPA). The libraries were multiplexed and then sequenced on Illumina HiSeq2500 (Illumina) to generate 30M of single-end 50 base pair reads.

Reads were mapped to the hg19 genome using RefSeq gene models with the aligner GSNAP. Per-gene counts were used to assess differential gene expression with the limma and edgeR software as implemented in the R programming language according to the limma user manual. A linear model was fitted on gene expression with terms for cell line identity, AZ-628 and cobimetinib treatment, as well as an interaction term for the treatments. Significance for linear model terms was determined by moderated t-tests as implemented in the limma software.

Clonogenic Assay

Cells were plated in duplicate in 6-well plates at 10,000 cells/well, allowed to attach overnight and treated for 8 days with the indicated compounds. Media with appropriate compounds was replenished every 72 hours. At 8 days cells were rinsed once with PBS, fixed and stained with crystal violet solution (Sigma Aldrich, HT90132) for 20 minutes and washed with water.

Immunoblotting

Cells lysed in lysis buffer (0.5% NP40, 20 mM Tris, pH 7.5, 137 mM NaCl, 10% glycerol, 1 mM EDTA) plus protease inhibitor mixture-complete mini (Roche Applied Science, 11836170001) and phosphatase inhibitor mix (Thermo, 78426). Lysates were centrifuged at 15,000 rpm for 10 minutes and the protein concentration determined using BCA (Thermo, 23227). Equal amounts of protein were subjected to SDS-PAGE NuPAGE 4-12% Bis-Tris Gel (Novex, WG-1403) and transferred to nitrocellulose membrane (BioRad, 170-4159). After blocking in blocking buffer (Li-Cor, 927-40000), membranes were incubated with the indicated primary antibodies and analyzed either by the addition of secondary antibodies IRDye 680LT Goat anti-Mouse IgG (H+L) (Li-Cor, 926-68050) or IRDye 800CW goat anti-Rabbit IgG (H+L) (Li-Cor, 926-32211). The membranes were visualized on the LiCor Odyssey CLx Scanner.

In Vitro Kinase Assays

Cells were plated and lysed as described in immunoblotting method. Cell lysates were incubated with anti-CRAF (Millipore 07-396) or anti-BRAF antibody (Millipore 07-453) and 50 µl of Protein A agarose beads (Millipore 16-125) for 2 h at 4° C. After washing with lysis buffer plus protease and phosphatase inhibitor mixtures, protein A beads were incubated with 0.4 µg of unactive MEK1 (Millipore 14-420) in 40 µl of kinase buffer (20 mM MOPS, pH 7.2, 25 mM β-glycerol phosphate, 5 mM EGTA, 1 mM sodium orthovanadate, 1 mM DTT, 120 µM ATP, 18 mM $MgCl_2$) for 30 min at 30° C. Samples were then analyzed by Western blot.

Ras Activity Assay

Levels of active GTP-loaded Ras were determined by GST-Raf-RBD pull-down assay (Thermo Scientific, 16117). In brief, GST-Raf-RBD fusion proteins were incubated with glutathione beads, and cells were collected in lysis buffer as recommended by the manufacturer. The cell lysates were incubated with the GST-Raf-RBD immobilized beads for 1.5 hours at 4° C. Bound proteins were eluted with SDS sample buffer and analyzed by Western blot.

siRNA Transfections

Cells were reverse transfected with 20 nM siKRAS (L-005069-00-0020) or siNTC (D-001810-10-20) (Dharmacon On-TARGETplus® pool) in the presence of lipofectamine RNAiMAX reagent (Life Technologies), according to the manufacturer's instructions. The medium was changed the day after transfection, and knockdown efficiency was assessed on day 4.

In Vivo Methods

Tumor Protein and RNA Isolation

GEM model tumor samples were collected and stored in RNALater (Qiagen, Valencia, CA). Total RNA was extracted with RNeasy Plus Mini kit (Qiagen) following manufacturer's instructions. RNA quantity was determined using Nanodrop (Thermo Scientific, Waltham, MA).

RT-PCR Analysis

Transcriptional readouts were assessed using either a Fluidigm instrument or standard RT-PCR assays according to manufacturer's recommendations. RNA (100 ng) was subjected to cDNA synthesis/pre-amplification reactions using the Applied Biosystems High Capacity cDNA RT Kit and TaqMan PreAmp Master Mix as per the manufacturer's protocol (Life Technologies, Carlsbad, CA). Following amplification, samples were diluted one to four with TE and qPCR was conducted on Fluidigm 96.96 Dynamic Arrays using the BIOMARK™ HD system according to the manufacturer's protocol. Cycle threshold (Ct) values were converted to fold change in relative expression values ($2^{-(ddCt)}$) by subtracting the mean of the three reference genes from the mean of each target gene followed by subtracting the mean vehicle dCt from the mean sample dCt.

Immunoblotting

To prepare protein lysates, cells were washed once with ice-cold PBS and lysed in 1× Cell Extraction Buffer (Invitrogen) supplemented with protease inhibitor tablet (Roche) and phosphatase inhibitors (Sigma). Protein concentration was determined using BCA Protein Assay (Pierce). Equal amounts of proteins were resolved by 10% Bis-Tris gels in 1×MOPS running buffer (Invitrogen) and transferred to nitrocellulose membranes (Invitrogen). Antibodies directed against the following proteins were used: CRAF, p-ERK, ERK1/2, p-MEK-1/2, MEK-1/2, cleaved PARP (Cell Signaling), p-p90RSK, GAPDH (EMD Millipore), p90RSK (Invitrogen). Antigen-antibody interaction was detected with HRP-conjugated goat anti-rabbit and goat anti-mouse antibodies (Jackson ImmunoResearch) using enhanced chemiluminescence detection reagents (Pierce) or with IRDye 800 conjugated, affinity purified anti rabbit IgG (LI-COR Biosciences) and Alexa Fluor 680 goat anti mouse IgG (Life Technologies) secondary antibodies using the Odyssey Infrared Imaging System (LI-COR Biosciences).

In Vivo Models

The establishment and monitoring of all tumor xenografts models were performed as previously shown and is described in Hoeflich et al. *Cancer Res.* 72(1): 210-219, 2012.

Test Material

Cobimetinib (GDC-0973) was prepared at Genentech as a suspension at various concentrations in methyl-cellulose tween (MCT). AZ-628 and LY3009120 were synthesized at Genentech and were prepared as MCT nanosuspensions. Cobimetinib, AZ-628, LY3009120, and vehicle control dosing solutions were prepared once a week for three weeks. The formulations were mixed well by vortexing before dosing. Test articles were stored in a refrigerator set to maintain a temperature range of 4° C.-7° C.

Subcutaneous Tumor Models

Xenograft studies were done as previously described in Hoeflich et al. (*Cancer Res.* 72(1): 210-219, 2012). Briefly, either $5 \times 10^6$ HCT116 or $10^7$ NCI-H2122 cells were implanted subcutaneously into the right flank of female NCR nude mice (6-8 weeks old) obtained from Taconic (Cambridge City, IN) weighing an average of 24-26 g. The mice were housed at Genentech in standard rodent microisolator cages and were acclimated to study conditions at least 3 days before tumor cell implantation. Only animals that appeared to be healthy and that were free of obvious abnormalities were used for each study. Tumor volumes were determined using digital calipers (Fred V. Fowler Company, Inc.) using the formula (L×W×W)/2. Tumor growth inhibition (% TGI) was calculated as the percentage of the area under the fitted curve (AUC) for the respective dose group per day in relation to the vehicle, such that % TGI=100×[1−(AUC$_{treatment}$/day)/(AUC$_{vehicle}$/day)]. Curve fitting was applied to Log$_2$ transformed individual tumor volume data using a linear mixed-effects model using the R package nlme, version 3.1-97 in R v2.12.0 (Pinheiro et al. *R Package Version* 3. 1-89, 2008). Mice were weighed twice a week using a standard scale.

Example 2

Figure 1B:
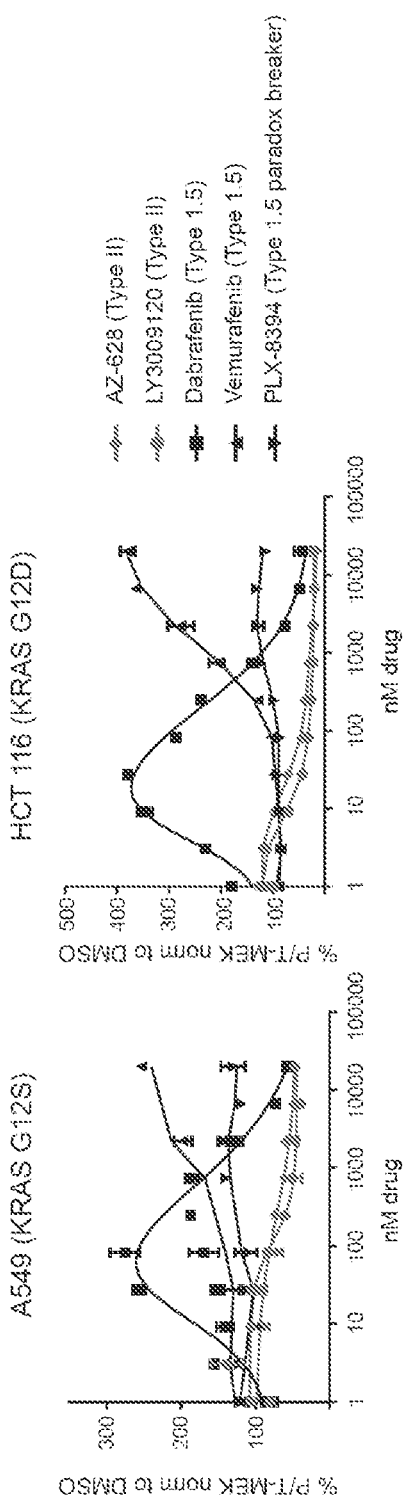
FIG. 1B is a series of graphs showing the ratio of P-MEK and total MEK plotted for various concentrations of different Type 1.5 and Type 2 RAF inhibitors.
Figure 1C:
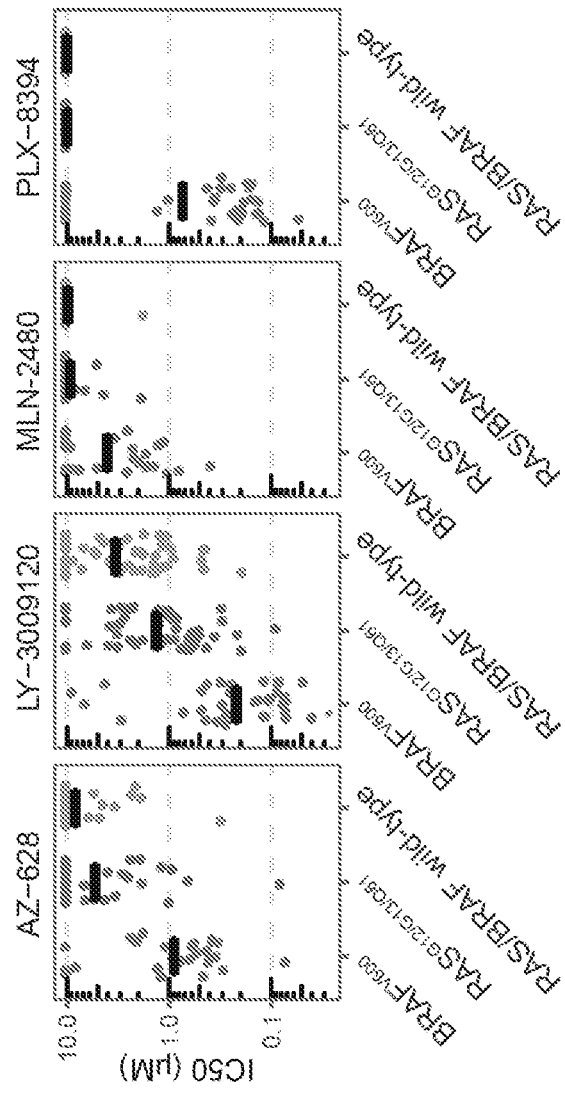
FIG. 1C is a series of graphs showing profiling of colon, lung, and skin cancer cell lines for sensitivity to three Type II pan-RAF inhibitors (AZ-628, LY-3009120, and MLN-2480) and the Type 1.5 "paradox-breaker" RAF inhibitor, PLX-8394, in 3-day cell viability studies. IC$_{50}$ values (µM) were determined using a four-parameter fit using nonlinear regression analysis.

RAF Kinase Inhibitors Lack Potent Single Agent Efficacy in KRAS Mutant Cell Lines In order to determine whether RAF kinase inhibitors could be used therapeutically in KRAS mutant cell lines, cell viability was assessed in a panel of RAF inhibitors in KRAS mutant versus BRAF-V600E cell lines with the Type 1.5 RAF inhibitors, dabrafenib, vemurafenib, and the "paradox breaker" PLX-8394, as well as the Type II RAF inhibitors, AZ-628 and LY3009120. The clinically approved Type 1.5 BRAF inhibitors, vemurafenib and dabrafenib, as well as PLX-8394 showed activity in BRAF-V600E mutant cell lines (as indicated in black), but not in KRAS mutant cell lines (as indicated in red) (FIG. 1A). As expected, the Type 1.5 inhibitors vemurafenib and dabrafenib, but not PLX-8394, led to paradoxical activation of downstream pMEK in KRAS mutant tumors (FIG. 1B). In contrast to the Type 1.5 inhibitors, Type II pan-RAF inhibitors showed better inhibition of KRAS mutant cell lines, however their potency in KRAS mutant cell lines was weaker than the activity observed in the BRAF-V600E mutant background (FIG. 1A). Consistent with this activity, Type II RAF inhibitors, as well as the recently reported paradox breaker PLX-8394, do not induce paradoxical activation (FIG. 1B). To expand upon these results, three Type II RAF inhibitors (LY-3009120, MNL-2480 and AZ-628) and PLX-8394 were next screened in a panel of 161 lung, skin, and colorectal cell lines (FIG. 1C). While there was a modest increase in activity of these inhibitors in RAS mutant lines compared to BRAF/RAS wild-type lines, BRAF-V600 cell lines were the most sensitive (FIG. 1C). These data suggest that a lack of paradoxical activation is insufficient to portend sensitivity in the RAS mutant background and that RAF kinase activity may not be essential for mutant KRAS-mediated growth.

Figure 1D:
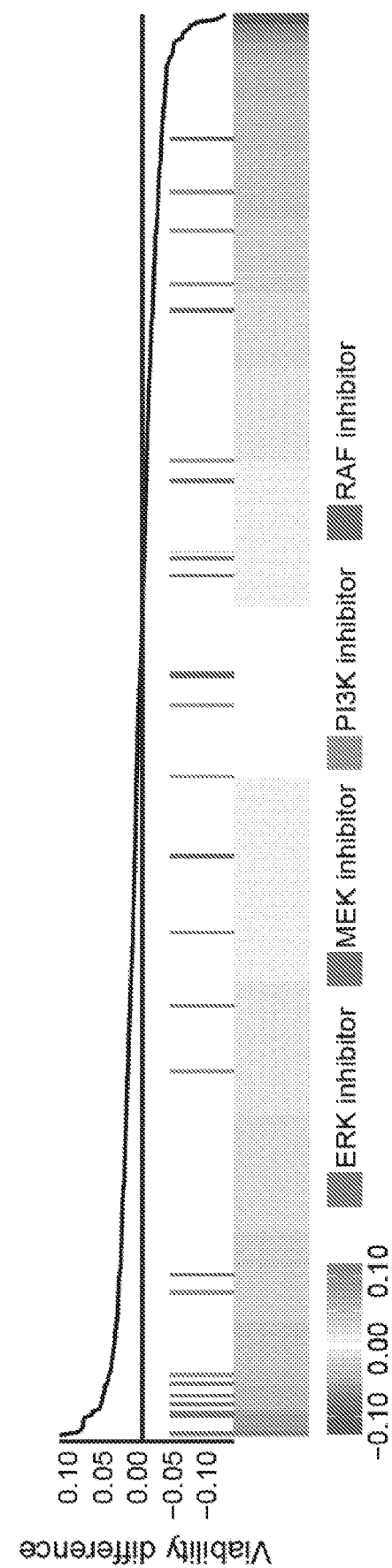
FIG. 1D is a graph showing mean viability differences for the A549 KRAS-G12S mutant line after treatment with 1 µM AZ-628+/−a tool compound from a small molecule library of 430 tool compounds. Cell viability in the A549 KRAS-G12S mutant line was measured after 3 days of treatment with 1 µM AZ-628+/−tool compound. The mean viability was calculated for each treatment, and the mean viability differences are plotted normalized to DMSO treated cells. Colored vertical bars indicate the inhibitor classes.

In order to determine whether a second pharmacological agent could sensitize KRAS mutant cell lines to RAF kinase inhibition, a library consisting of 480 small molecule tool compounds in combination with either DMSO or 1 μM of the Type II RAF inhibitor AZ-628 was screened in the A549 KRAS-mutant lung cancer cell line. The top hit from this screen was the MEK inhibitor cobimetinib (GDC-0973). AZ-628 combined well with other MAPK pathway inhibitors, including four distinct MEK inhibitors and two ERK inhibitors in the top 20 hits (FIG. 1D and Supplemental Table 1). Other notable hits included several microtubule inhibitors, as well as PI3K inhibitors pictilisib (GDC-0941) and taselisib (GDC-0032). To validate the hits from the primary screen, the top hits in HCT-116 (KRAS-G13D/PIK3CA mutant) cell lines were rescreened, which confirmed MEK inhibitors as the strongest agents that combine with Type II RAF inhibitor AZ-628.

Example 3

Figure 1E:
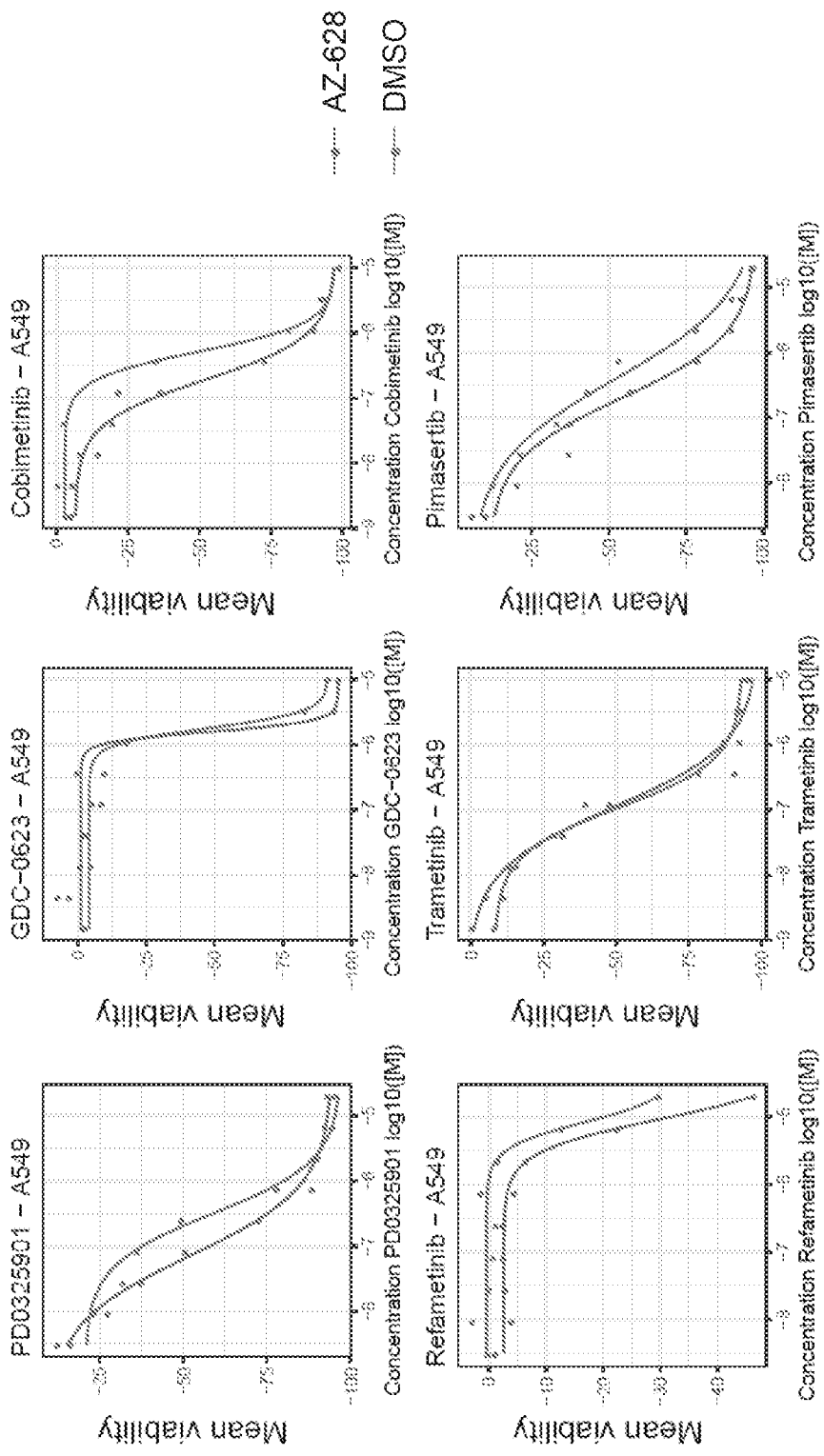
FIG. 1E is a series of representative dose-response curves of the indicated MEK inhibitors from the compound screen in A549 cells, with or without 1 µM AZ-628.
Figure 1F:
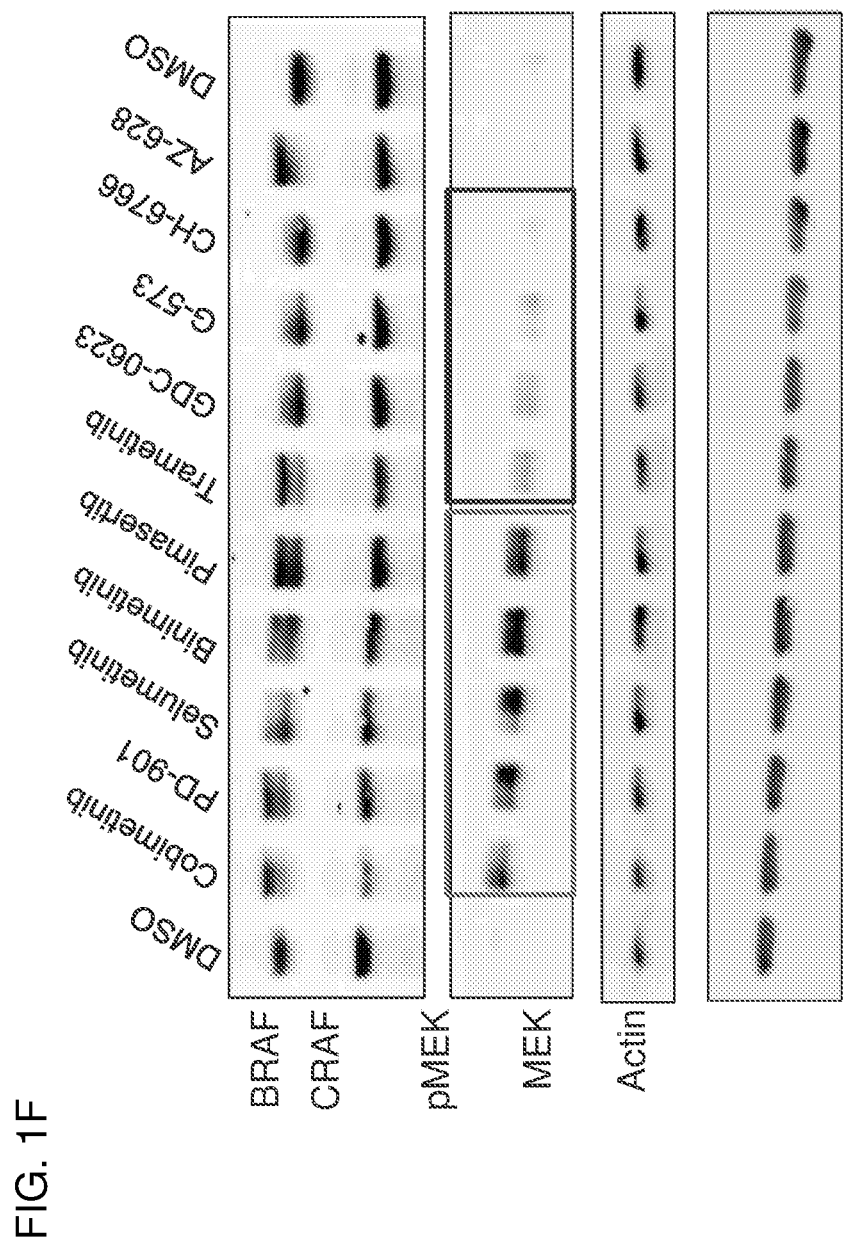
FIG. 1F is an immunoblot showing total BRAF and CRAF, and phospho- and total MEK relative to control (actin) following treatment of A549 cells with the indicated molecules for 24 hours at 1 µM.
Figure 1G:
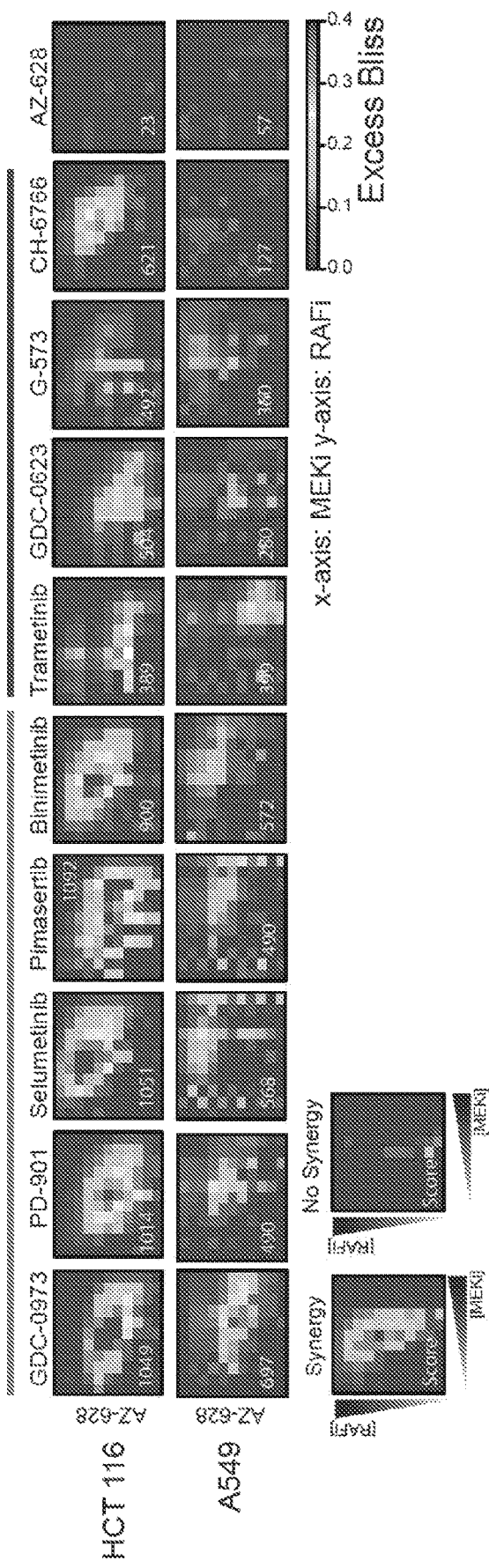
FIG. 1G is a set of images showing calculated Bliss excess scores for 12×12 matrix titrations of AZ-628 and the indicated MEK inhibitors. A549 cells were treated with a 12×12 matrix titration of AZ-628 and various MEK inhibitors for 3 days. Cell viability was assessed by CELLTITER-GLO®, and Bliss excess scores were calculated.

Conformation-Specific RAF and MEK Inhibitors Exhibit Synergy in RAS Mutant Cell Lines Although the top hit from the screen was a MEK inhibitor, not all MEK inhibitors were equally synergistic. While cobimetinib, pimasertib, refametinib, and PD901 scored highest among the compounds tested, trametinib and GDC-0623 did not show a difference in mean viability even though they are both potent MEK inhibitors (FIG. 1E). MEK inhibitors were previously reported to have differential mechanisms of action depending on their ability to trap an inactive RAF-MEK complex (Hatzivassiliou et al., *Nature* 501:232-236 (2013)). This drug-stabilized complex prevents RAF from phosphorylating MEK. To determine whether the mechanism of action of the MEK inhibitor impacts synergy with AZ-628, several MEK inhibitors having different molecular mechanisms were tested and it was found that MEK inhibitors that trap the inactive RAF-MEK complex and do not induce pMEK (e.g., trametinib, GDC-0623, G-573, and CH-6766) (FIG. 1F) are also less synergistic with AZ-628 in a full-dose Bliss matrix analysis (FIG. 1G).

Figure 2A:
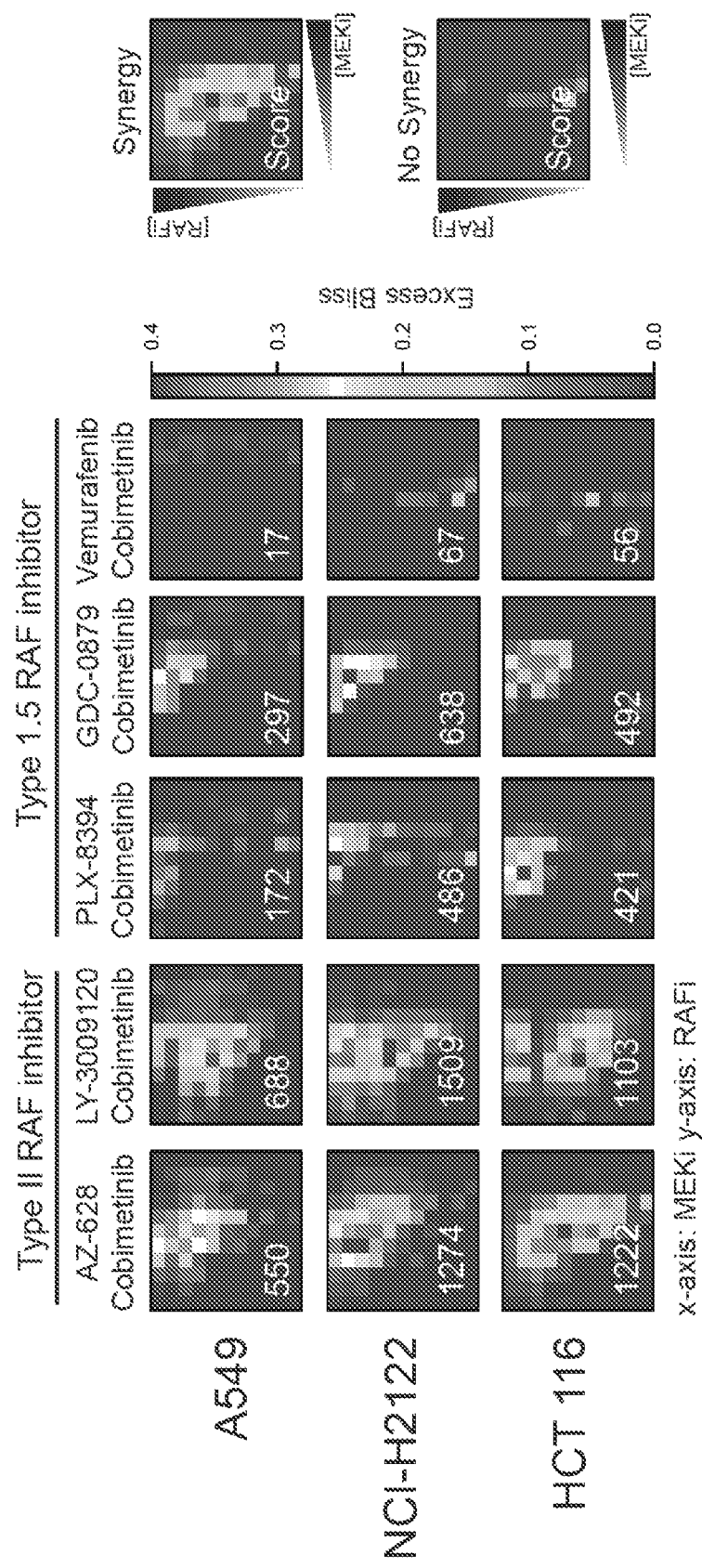
FIG. 2A is a set of images showing calculated Bliss excess scores for 12×12 matrix titrations of cobimetinib and the indicated RAF inhibitors. Cell viability was assessed by CELLTITER-GLO® in A549 cells treated with cobimetinib and the indicated RAF inhibitors for 3 days.

Based on the above observations, it was hypothesized that just as MEK inhibitors are not all equivalently synergistic with RAF inhibitors, there would be discrepancy in synergy between different RAF inhibitors in combination with MEK inhibitors. While Type II RAF inhibitors were found to readily combine with cobimetinib, Type 1.5 RAF inhibitors (including the paradox breaker PLX-8394) did not synergize with MEK inhibitors in KRAS mutant cell lines (FIG. 2A). This suggests that paradoxical activation is not the primary reason Type 1.5 BRAF inhibitors do not synergize with MEK inhibitors in this mutational setting.

Figure 2B:
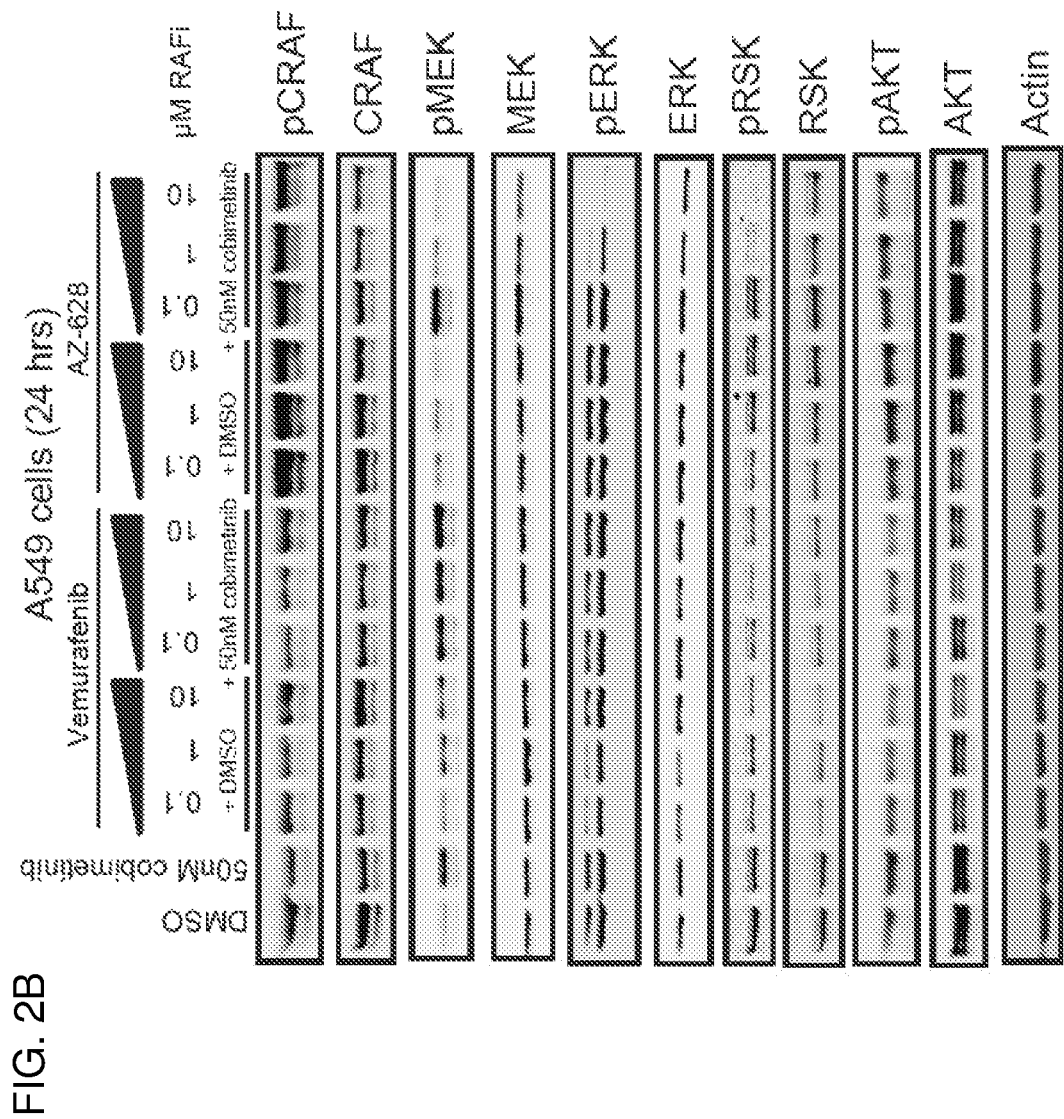
FIG. 2B is an immunoblot showing phospho- and total CRAF, MEK, ERK, RSK and AKT, relative to control (actin), following treatment of A549 cells with 50 nM cobimetinib and/or RAF inhibitor as indicated for 24 hours.
Figure 2C:
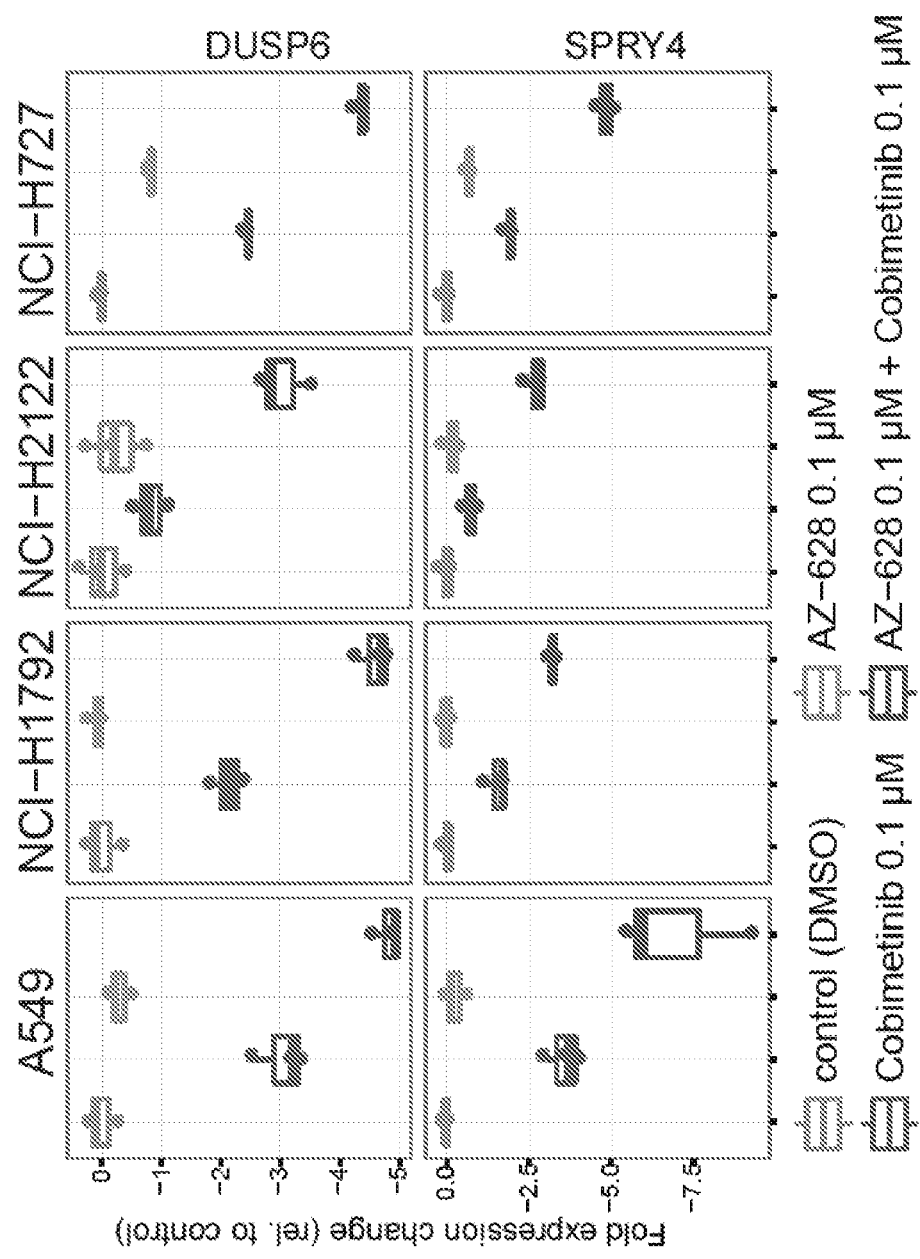
FIG. 2C is a set of graphs showing RNA-seq fold-change expression data for DUSP6 and SPRY4 in four KRAS mutant lung cancer cell lines treated with 0.1 µM cobimetinib, 0.1 µM AZ-628, or both for 6 hours, relative to DMSO control treated cells.
Figure 2D:
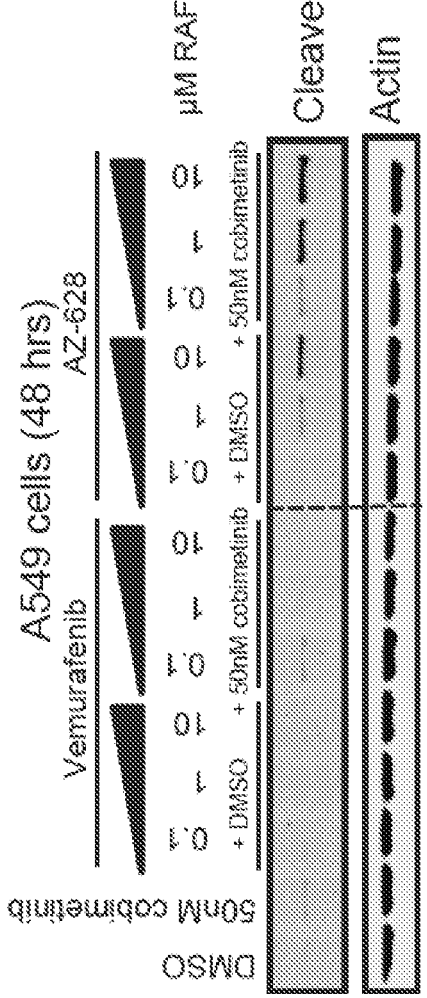
FIG. 2D is an immunoblot showing increased cleaved PARP, relative to control (actin), in A549 cells treated with AZ-628 combined with cobimetinib versus vemurafenib with or without cobimetinib at the indicated concentrations for 48 hours.
Figure 2E:
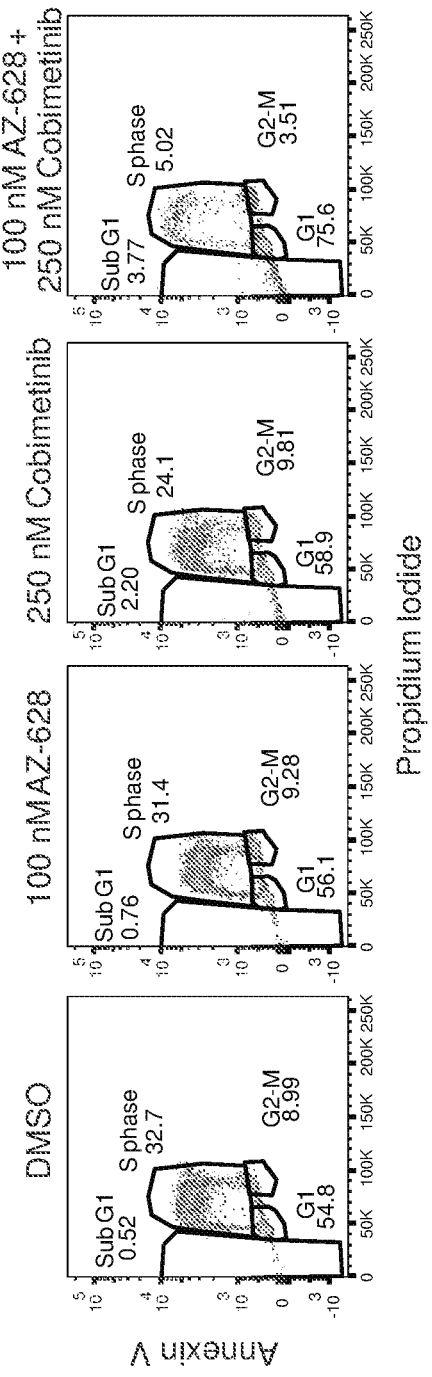
FIG. 2E is a set of graphs showing flow cytometry cell cycle/apoptosis analysis (propidium iodide and Annexin V) for A549 cells treated with the indicated concentrations of AZ-628, cobimetinib, or both.
Figure 2F:
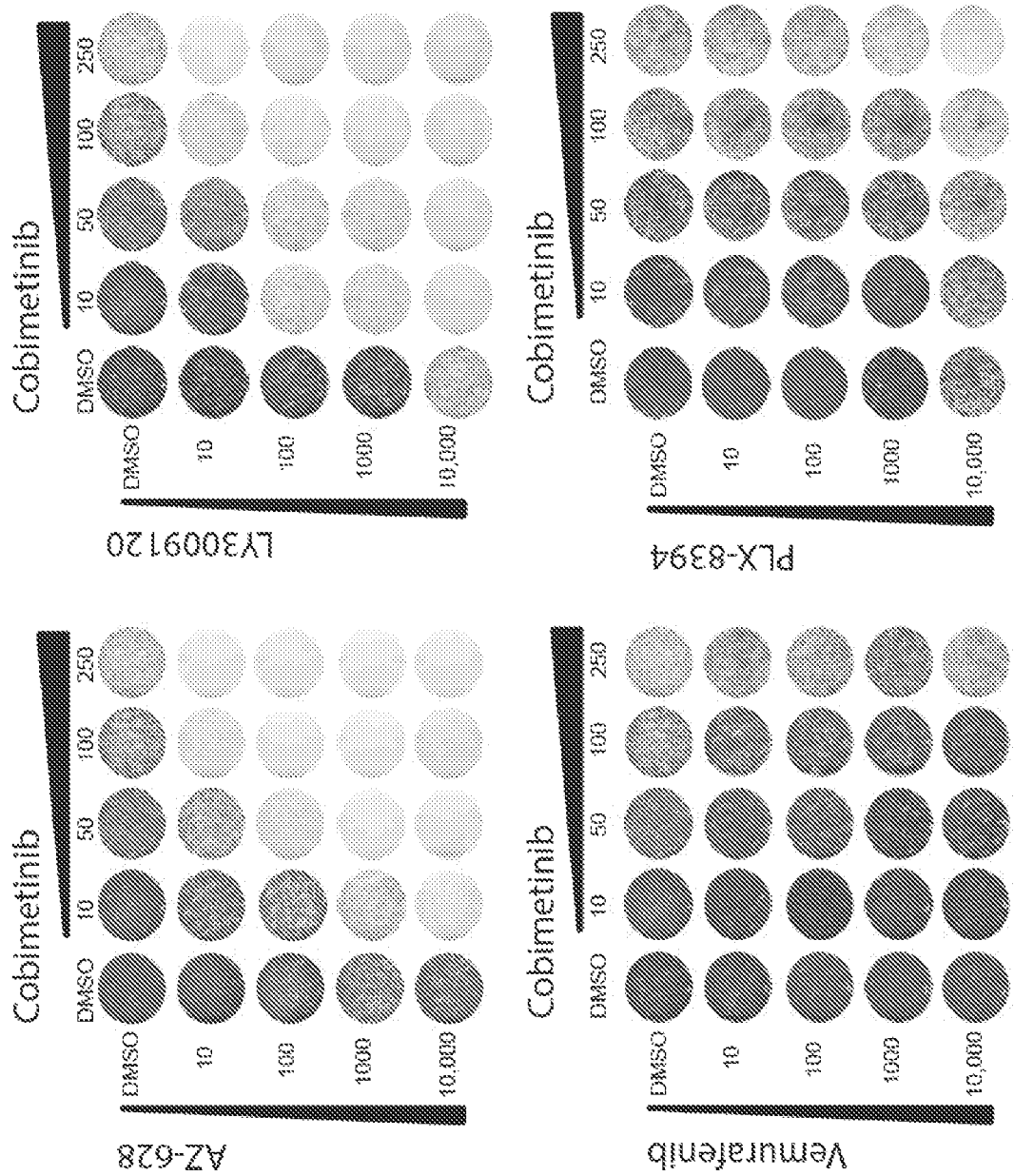
FIG. 2F is a set of images of colony growth assays, showing that type II RAF inhibitors exhibit synergistic activity with cobimetinib and enhance cell death even at sub-efficacious single agent concentrations. A549 cells were treated with the indicated concentrations of RAF inhibitor or cobimetinib, and NCI-H2122 cells were treated with the indicated concentrations of RAF inhibitor LY-3009120 or cobimetinib. Media with appropriate compounds was replenished every 72 hours. Cells were cultured for 8 days and then stained with crystal violet.

To test if these changes in sensitivity associate with the anticipated changes in pathway signaling, A549 and HCT 116 cells were treated with increasing concentrations of the RAF inhibitors vemurafenib and AZ-628 (0.1-10 µM), and a fixed dose of cobimetinib. While vemurafinib was unable to decrease pathway signaling in the presence or absence of cobimetinib in the A549 KRAS mutant line, AZ-628 only in combination with cobimetinib effectively inhibited MAPK pathway output at the level of pMEK, pERK and pRSK (FIG. 2B). Pathway inhibition was restricted to the MAPK pathway as there was little observed impact on pAKT levels. Using RNA-Seq canonical downstream transcriptional targets of MAPK signaling, DUSP6 and SPRY4, were examined six hours after treatment with 0.1 µM AZ-628, 0.1 cobimetinib, or the combination in four KRAS mutant lung cancer cell lines (FIG. 2C). A significant interaction was observed between the treatments (P<0.01, moderated T-test) where the downregulation of these genes was more profound than expected if the effect of combining the two single agents was merely additive. These data indicate that the compounds also cause a synergistic transcriptional repression of the MAPK pathway. The combination also resulted in a significant induction of cell apoptosis after 48 hours of treatment, as evidenced by increased staining of cleaved-PARP by western blot (FIG. 2D) and a notable increase in the sub-G1 and G1 population as assessed by flow cytometry for Annexin V and propidium iodide (FIG. 2E). To test whether these combination effects resulted in durable suppression of cell growth, the long-term growth effects of the MEK/RAF inhibitor combination in colony formation assays were also tested. A marked synergy was observed between cobmetinib in combination with the Type II inhibitors AZ-628 or LY3009120, but not with Type 1.5 inhibitors vemurafinib and PLX-8394 (FIG. 2F).

Example 4

Combined Treatment of RAF and MEK Inhibitors Exhibit Efficacy In Vivo

Figure 3A:
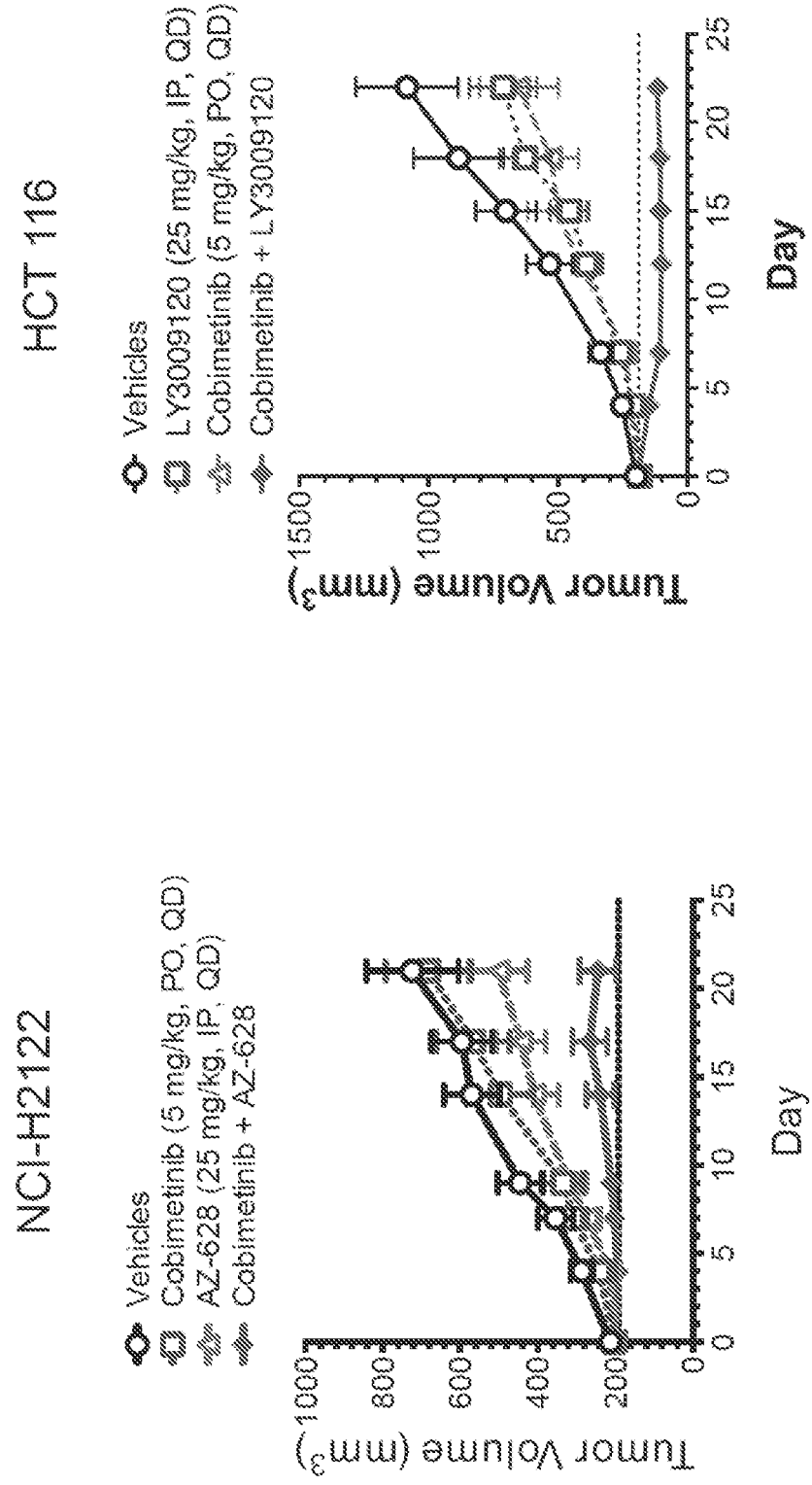
FIG. 3A is a set of graphs showing tumor volume over time for MEK inhibitor cobimetinib (5 mg/kg, orally (PO), daily (QD)) with the pan-RAF inhibitor AZ-628 (25 mg/kg, intraperitoneally (IP), QD) or LY-3009120 (25 mg/kg, IP, QD) in the NCI-H2122 and HCT 116 xenograft tumor models, respectively (n=10/group, mean tumor volume±SEM).
Figure 3B:
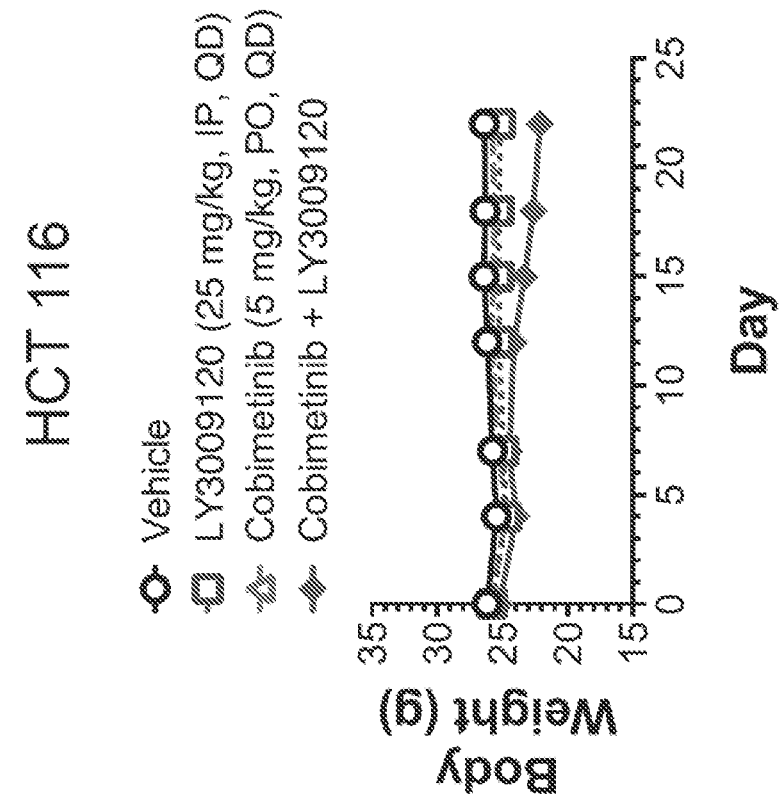
FIG. 3B is a set of graphs showing mouse body weight data for single agent MEK inhibitor cobimetinib (GDC-0973), pan-RAF inhibitor AZ-628 or LY-3009120, or the indicated combination, in NCI-H2122 and HCT-116 xenograft mice (n=10/group, mean tumor volume±SEM).
Figure 3B:
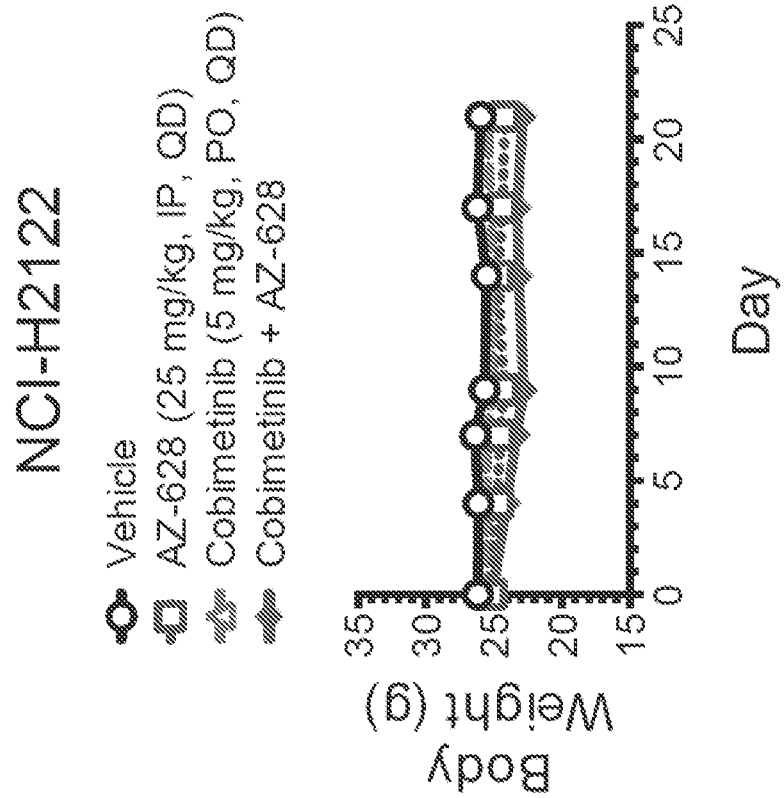
Figure 3C:
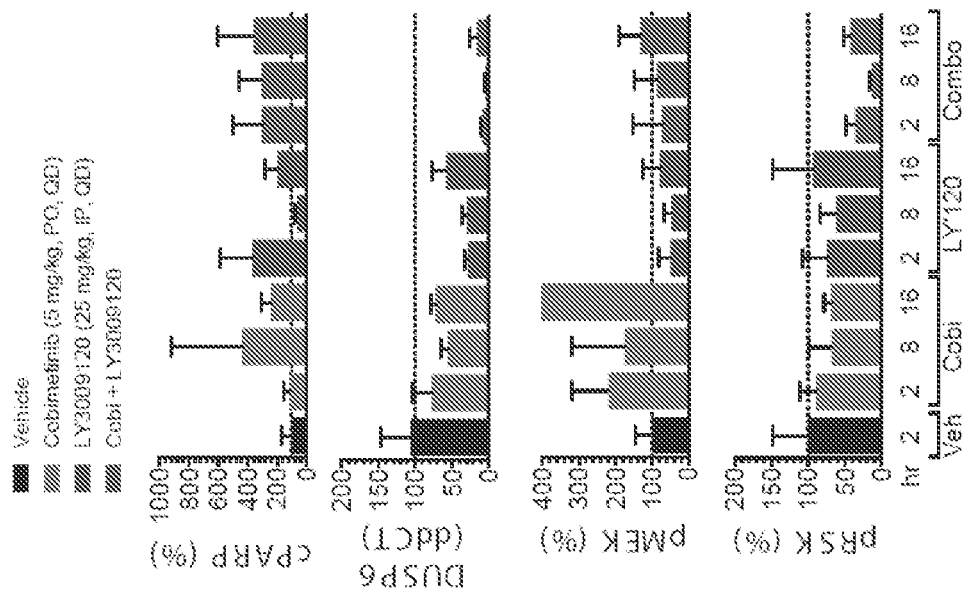
FIG. 3C is a set of bar graphs showing tumor pharmacodynamics studies in NCI-H2122 and HCT 116 tumor-bearing mice after 4 days of treatment at the indicated time points following last dose (2, 8, 16, and 24 hr). Bar graphs indicate quantified values of the indicated proteins (cleaved PARP (Western blot), pMEK/total MEK (ECLA), pRSK/total RSK (Western blot), or for the downstream RNA transcript DUSP6 (RT-PCR) normalized to vehicle control (n=4/group, mean±SD).
Figure 3C:
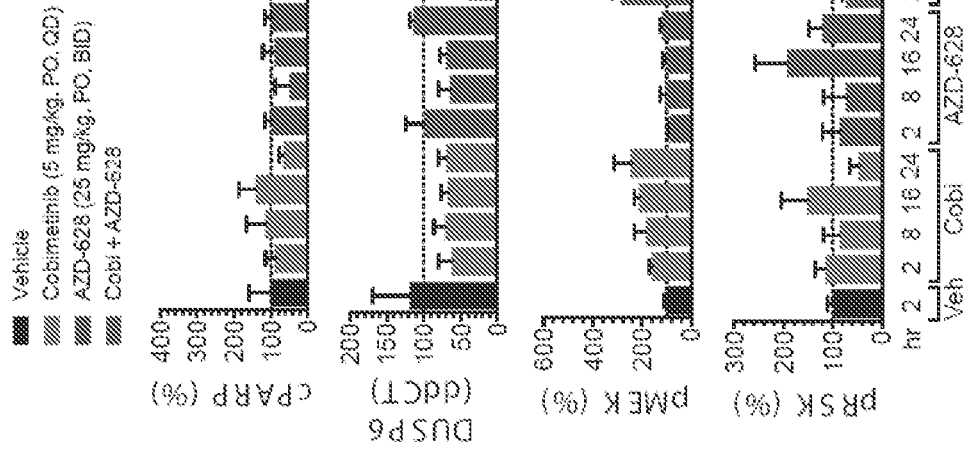
Figure 3D:
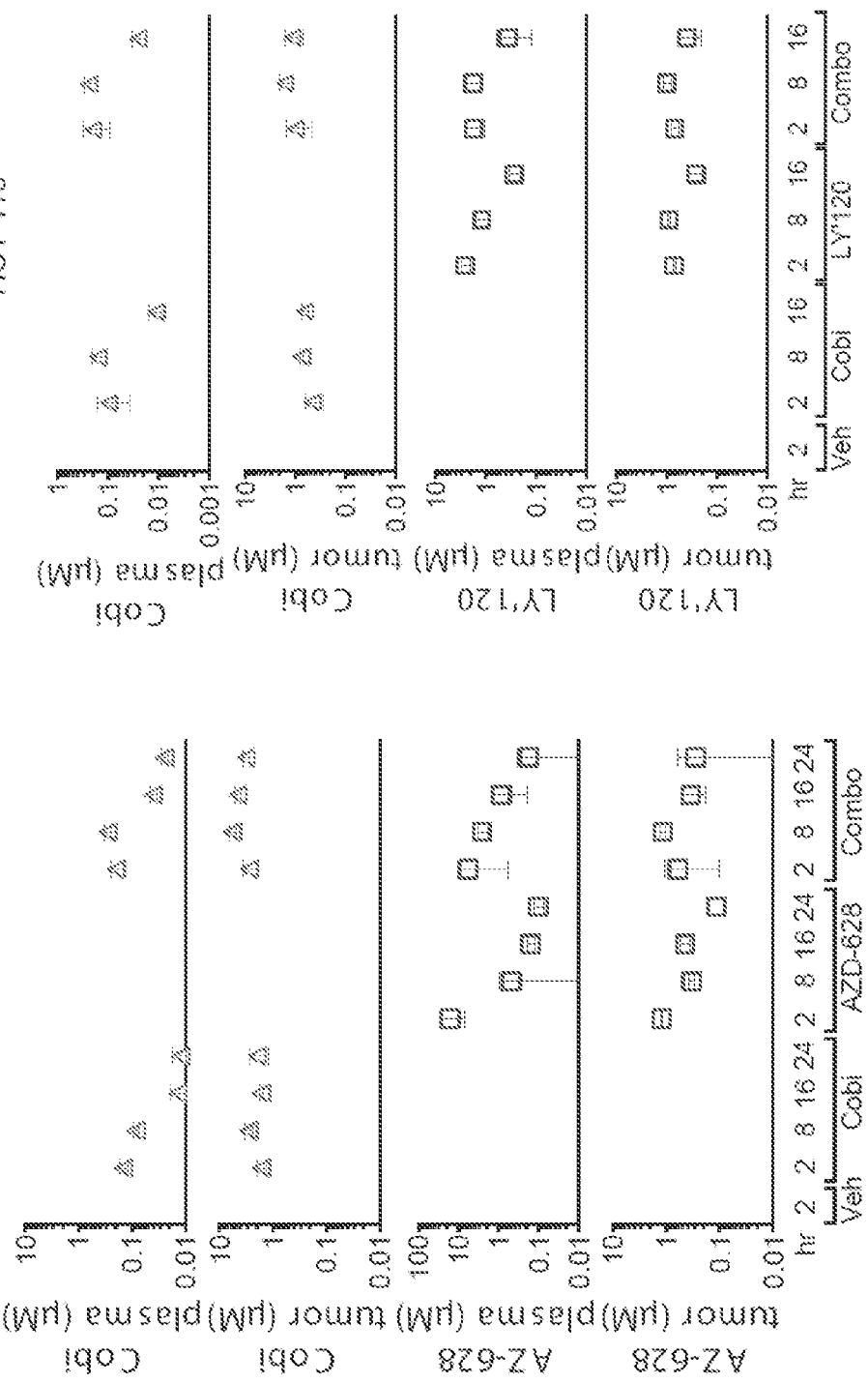
FIG. 3D is a set of bar graphs showing compound plasma concentrations after the times indicated on the x-axis.

To determine if the combination effects observed in vitro translated to in vivo efficacy, the Type II pan-RAF inhibitors LY3009120 and AZ-628 were tested in combination with cobimetinib in NCI-H2122 lung (AZ-628+GDC-0973) and HCT116 colon (LY3009120+GDC-0973) xenograft tumor models. Consistent with the in vitro data, the in vivo data indicate a robust combination effect of either Type II RAF inhibitor plus MEK inhibitors when compared to the efficacy of either molecule alone (FIG. 3A). While LY3009120 or cobimetinib as single agents modestly inhibited tumor growth, the combination was capable of effectively regressing the tumors. Importantly, the combination was well tolerated in the mice, resulting in little or minimal changes in body weight post-treatment (FIG. 3B). To assess how well the combination impacted MAPK signaling, tumor samples were collected 4 days post-treatment at various time points. Quantification of MAPK pathway signaling demonstrated better suppression of pERK and pRSK, resulting in deeper suppression of downstream MAPK target genes, DUSP6 and SPRY4, by the combination of LY3009120 and GDC-0973, than compared to either of the inhibitors alone at all time points tested (FIG. 3C). Plasma and tumor drug concentrations confirmed that the improved inhibitory activity was not due to increased drug exposure but to a drug-drug interaction (FIG. 3D). Taken together, the combination of RAF and MEK inhibition exhibited significant combination efficacy in vivo.

Example 5

MEK Inhibitor Treatment Induces RAF Kinase Activity in a RAS-Dependent Manner

Figure 4A:
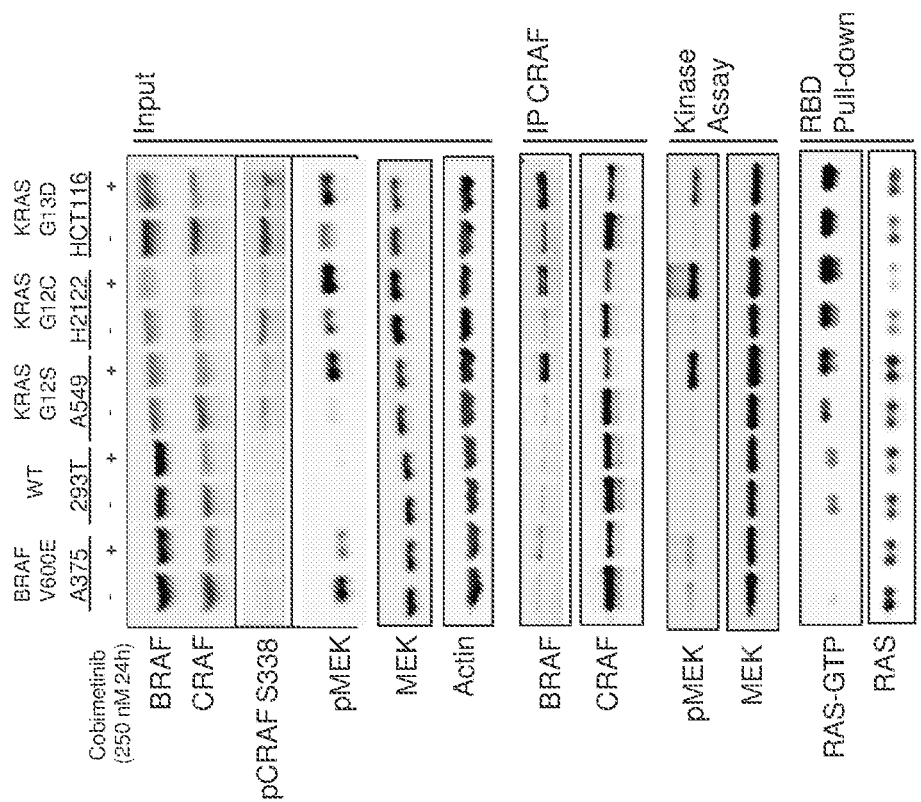
FIG. 4A is an immunoblot showing that MEK inhibition induces pathway feedback reactivation to a greater extent in KRAS mutant cell lines, resulting in increased RAS-GTP levels. The indicated cancer cell lines were treated with either DMSO or 250 nM cobimetinib for 24 hours and protein lysates were analyzed by Western blotting for phospho- or total BRAF, CRAF, or MEK, relative to control (actin). CRAF, RBD-RAF1, and BRAF were immunoprecipitated (IP) from the same lysates and were analyzed by Western blot. The CRAF immunoprecipitates were analyzed for kinase activity utilizing inactive MEK as the substrate.
Figure 4E:
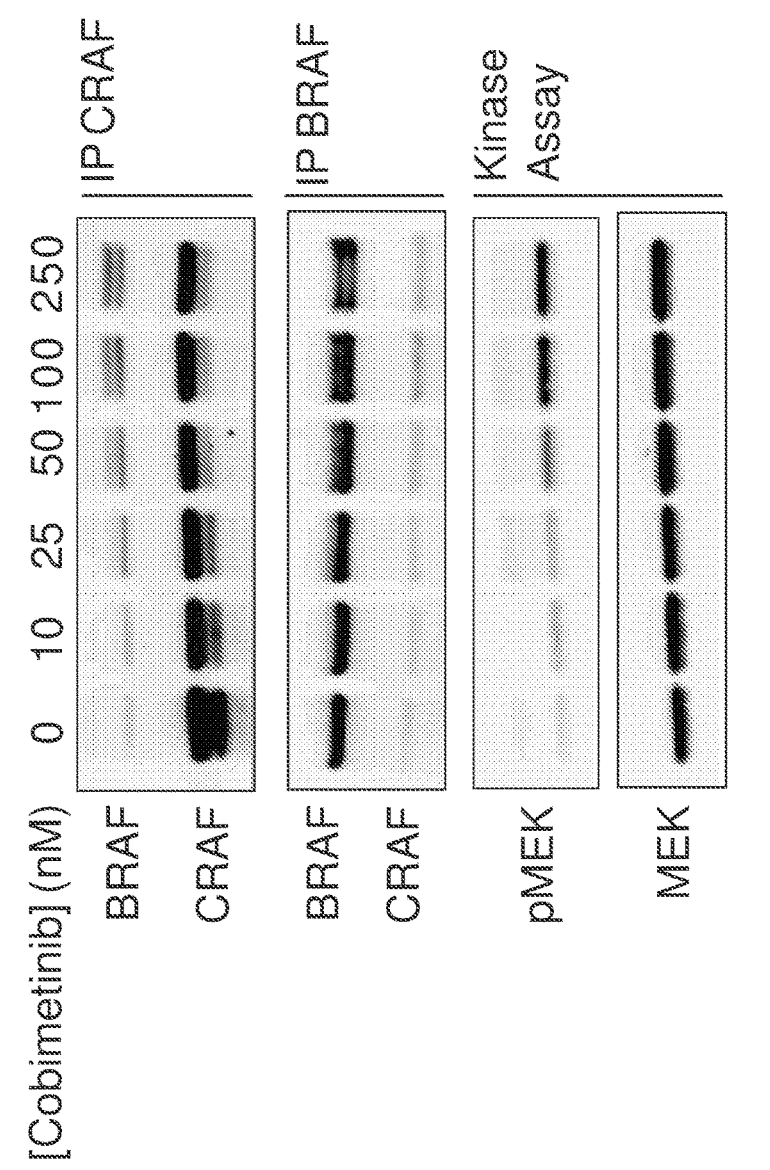
FIG. 4E is an immunoblot showing the results of CRAF and BRAF IP experiments and subsequent kinase activity assays. A549 cells were treated with increasing concentrations of the MEK inhibitor GDC-0973, and CRAF and BRAF were immunoprecipitated in the same lysates and analyzed by Western blotting. The CRAF immunoprecipitates were analyzed for kinase activity utilizing inactive MEK as the substrate.
Figure 4D:
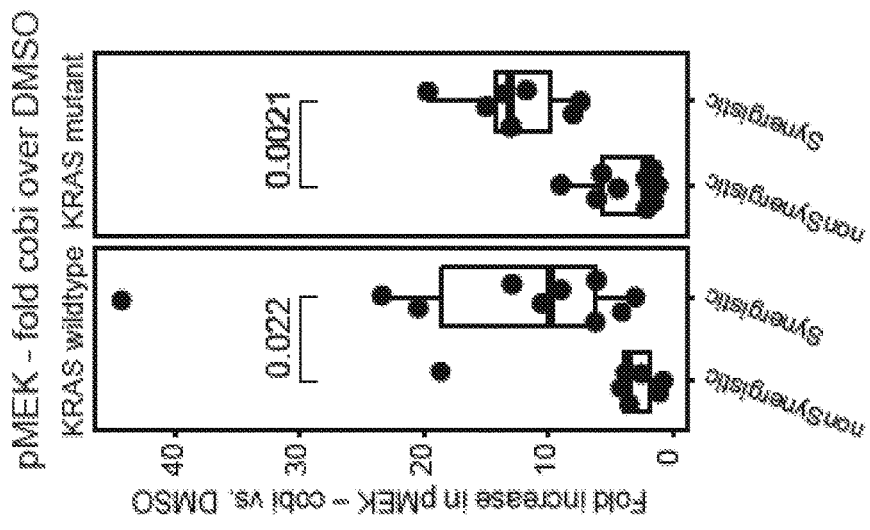
FIG. 4D is a graph showing the relative fold increase in cobimetinib-induced pMEK levels of the synergistic and non-synergistic KRAS mutant and wild-type lung cancer cell lines in FIGS. 4B and 4C normalized to DMSO treated control cell lines. P-values were determined by Wilcoxon rank sum test.

To study the mechanism of synergy observed between cobimetinib and the Type II RAF inhibitor AZ-628, a panel of KRAS mutant and wild-type cell lines was treated with cobimetinib for 24 hours and effects on MAPK pathway signaling were examined. Following treatment with cobimetinib, an increase in the pMEK levels in the KRAS mutant cells but not the KRAS wild-type cells was observed, indicating increased flux through the MAPK pathway (FIG. 4A). In a set of separate experiments in which a panel of KRAS mutant and wild-type colon and lung cancer cell lines were examined for induction of pMEK following treatment with cobimetinib for 24 hours, an increase in the pMEK levels in the KRAS mutant and wild-type synergistic cells but not the KRAS mutant and wild-type non-synergistic cells was observed (FIGS. 4B-4D). To further understand how cobimetinib treatment alters the pathway, RAF dimerization was assessed through immunoprecipitation of CRAF. In KRAS mutant cell lines (A549, H2122, and HCT116) treated with cobimetinib, BRAF strongly co-immunoprecipitated with CRAF (FIG. 4A). This was not observed in the KRAS wild-type (293T) or BRAFV600E (A375) cell lines tested. The RAF dimers were subsequently assayed for in vitro kinase activity through the exogenous addition of MEK and ATP. These results indicate that the RAF dimers present in KRAS mutant cells lines upon addition of cobimetinib are highly active (FIG. 4A) and able to phosphorylate MEK at levels significantly higher than those treated with DMSO control. In order to investigate the mechanism further, RAS-GTP levels upon treatment with GDC-0973 in KRAS mutant and wild-type cell lines were evaluated. The KRAS mutant lines showed elevated RAS-GTP levels at baseline and upon cobimetinib treatment, likely explaining the induction of RAF dimers and RAF kinase activation (FIG. 4A). Both the formation of the BRAF-CRAF heterodimer, as well as the increase in kinase activity of the heterodimer, were dose-dependent upon addition of cobimetinib occurring at 50-100 nM (FIG. 4E). This result explains the synergistic effect observed in the 8-day clonogenic assays, where at concentrations of 50-100 nM cobimetinib and 100 nM AZ-628 concentrations had little effect on cell growth on their own (FIG. 2F).

The ability of RAF inhibitors to inhibit cobimetinib-induced RAF dimers was next examined. Cobimetinib-induced RAF dimers were immunoprecipitated from A549 cells, and then treated with AZ-628, LY3009120, or vemurafinib. Only the Type II RAF inhibitors, which can bind to RAF dimers, were able to inhibit kinase activity as demonstrated by the decreased levels of pMEK in the IP kinase assay (FIG. 4F), and consistent with the observed synergy observed in this line (FIG. 2A).

Figures 4F, 4G:
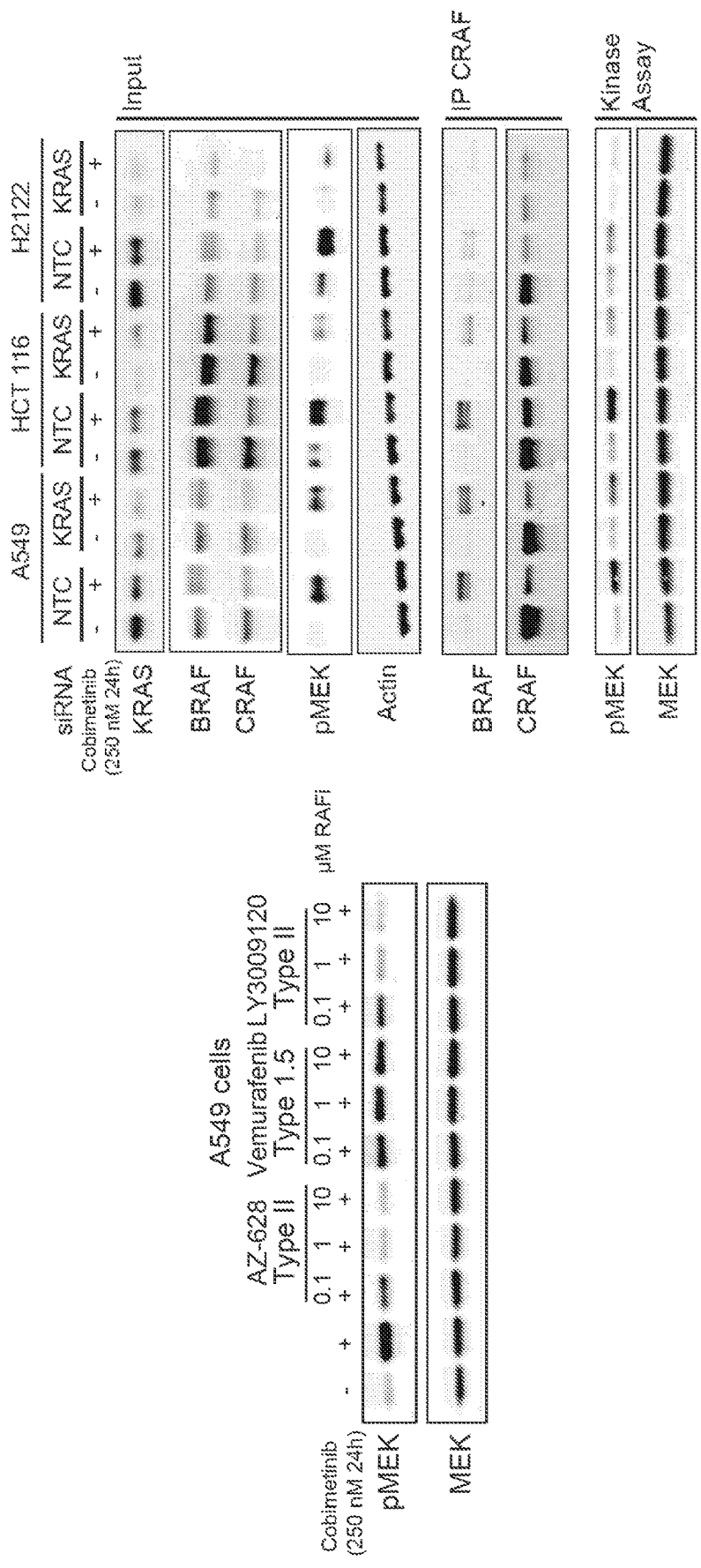
FIG. 4F is an immunoblot showing that Type II pan-RAF inhibitors, but not legacy Type 1.5 RAF inhibitors, can reverse MEK inhibitor-induced hyper-phosphorylation of MEK in KRAS mutant cells. MEK phosphorylation was assessed by Western blot in A549 cells treated with 250 nM cobimetinib for 24 hours followed by addition of the indicated RAF inhibitors at increasing concentrations for 24 hours.
FIG. 4G is an immunoblot showing that KRAS knockdown dampens MAPK reactivation following MEK inhibition. The indicated cell lines were reverse-transfected with 20 nM si-KRAS (L-005069-00-0020) or si-NTC (D-001810-10-20) (Dharmacon On-TARGETplus® pool) in the presence of lipofectamine RNAiMAX® reagent (Life Technologies), according to the manufacturer's instructions. The medium was changed the day after transfection, and knockdown efficiency was assessed by Western blot on day 4. 250 nM cobimetinib was added to the cells for 24 hours.

Cobimetinib treatment results in disabled feedback and robust pathway "reactivation," as evidenced by increases in RAS-GTP levels, RAF dimers, and pMEK, an effect that is more pronounced in KRAS mutant cell lines. To test if mutant KRAS is required for this activity, siRNA targeting KRAS was utilized, and its effects on MAPK signaling were observed in the presence or absence of cobimetinib. In each KRAS mutant cell line tested, KRAS knockdown dampened the cobimetinib-induced levels of pMEK, as well as formation of RAF dimers and in vitro kinase activity (FIG. 4G). Collectively, these data indicate that mutant KRAS plays an essential role in mediating reactivation of the MAPK pathway due to increased RAS-GTP levels following single agent MEK inhibition.

Example 6

Figure 5A:
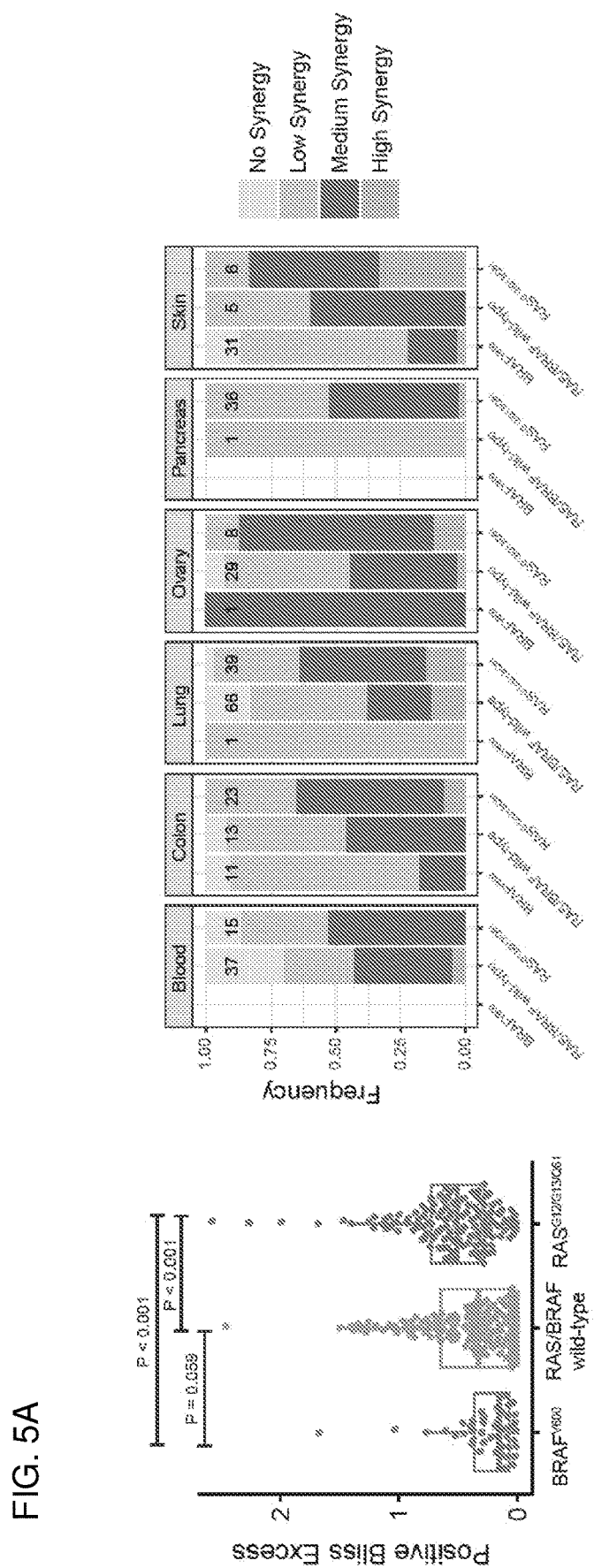
FIG. 5A is a graph showing that the combination of pan-RAF and MEK inhibitors resulted in greater synergy in RAS mutant (G12/G13/Q61) cell lines, and a subset of RAS/RAF wild-type cell lines relative to BRAF-V600 cell lines. Cell viability was assessed using CELLTITER-GLO® in a panel of 322 colon, lung, and pancreatic cancer cell lines treated with a 9 step 3-fold serial dilution of 10 μM AZ-628, 1 μM cobimetinib, or codilution of these for 3 days. Synergy scores are the sum of the positive Bliss excess over the concentration combinations measured. Bar graphs show four states of synergy: No synergy (Light grey), Low Synergy (dark grey), Medium Synergy (blue), and High Synergy (orange). Level of synergy was determined by mixture modeling on the positive Bliss excess and the distribution of these states over the various tissues.

Type II RAF Inhibitors Synergize with MEK Inhibitors in Subsets of KRAS Mutant and Wild-Type Cell Lines To determine whether particular genotypes are more sensitive to the combination of Type II pan-RAF inhibitors with MEK inhibitors, 322 cell lines, including cell lines where RAS mutations are significant and frequently found (pancreas, lung, colorectal, skin, ovary and blood), were screened with both single agents, AZ-628 (starting at 20 µM) and cobimetinib (starting at 1 µM), as well as a co-dilution of both compounds. From these data the positive Bliss excess over the co-dilution series as a measure of synergy was calculated. Significantly higher synergy scores were observed in KRAS and NRAS mutant cell lines compared to either BRAF-V600 mutants or wild-type (non-RAS/BRAF-V600 mutants) cell lines (FIG. 5A) ($p<0.001$, two-sided t-test). A mixture modeling approach was then used to group the cell lines from each tissue type into the following categories: no synergy, low synergy, medium synergy, or high synergy. When the distribution of these categories over all indications was examined, a strong association between medium and high synergy responders in the RAS mutants group compared to the wild-type or BRAF-V600 cell lines was observed (FIG. 5A).

Figure 5B:
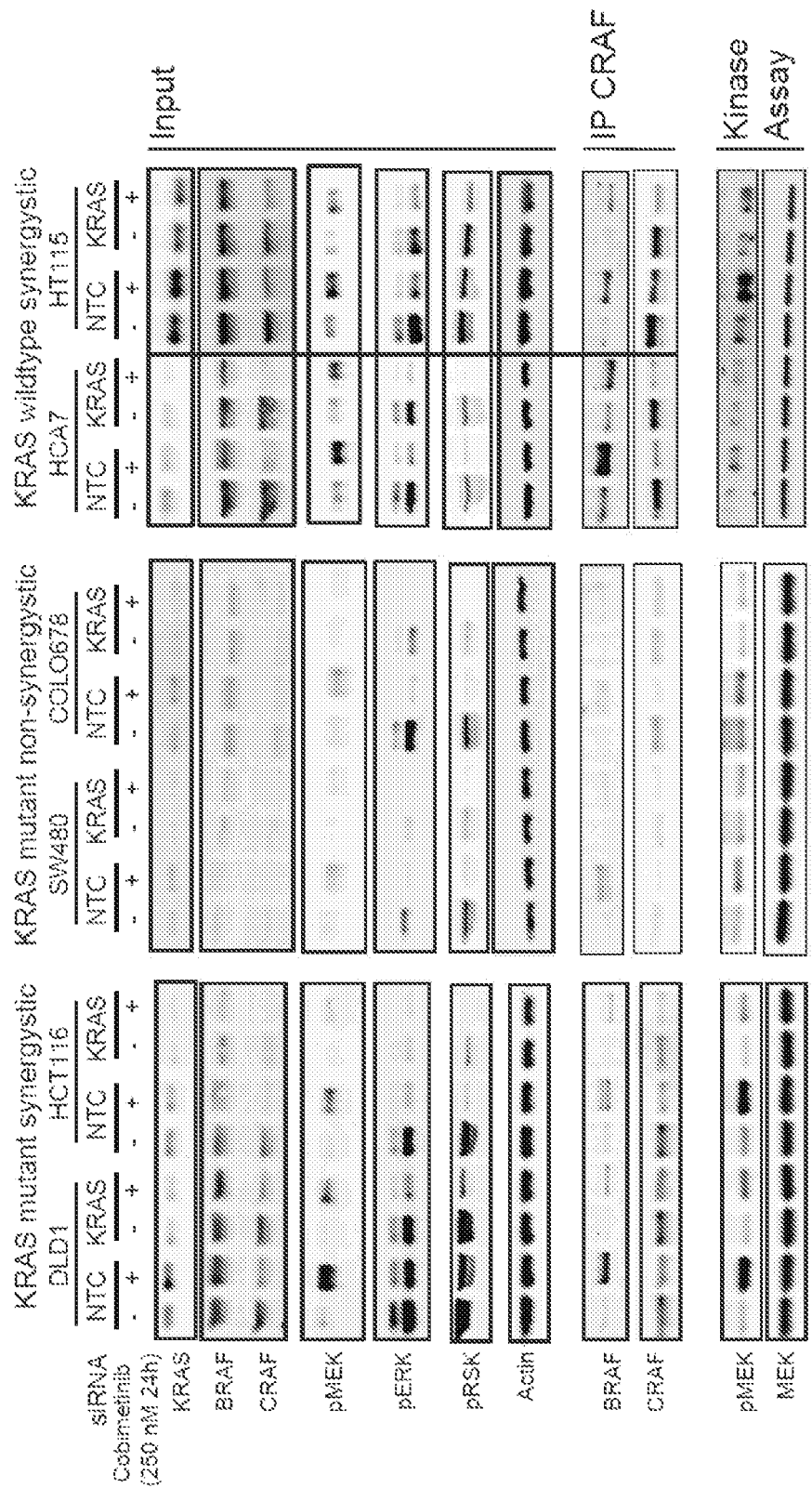
FIG. 5B is a set of immunoblots showing KRAS mutant and wild-type cancer cell lines representative of the indicated states of synergy and demonstrating that response correlates with basal levels of MAPK signaling and feedback reactivation via KRAS, RAF dimers, and kinase activity. Cells were reverse-transfected with 20 nM si-KRAS (L-005069-00-0020) or si-NTC (D-001810-10-20) (Dharmacon On-TARGETplus® pool) in the presence of Lipofectamine RNAiMAX® reagent (Life Technologies), according to the manufacturer's instructions. The medium was changed the day after transfection, and knockdown efficiency was assessed on day 4. 250 nM cobimetinib was added to the cells for 24 hours. Protein lysates were analyzed by Western blotting for phospho- and/or total KRAS, BRAF, CRAF, MEK, ERK, and RSK, relative to control (actin). CRAF and RAF1-RBD were immunoprecipitated from the same lysates and analyzed by Western blotting. The CRAF immunoprecipitates were analyzed for kinase activity utilizing inactive MEK as the substrate.

While strong synergy in the RAS mutant cell lines was observed, RAS mutant cell lines that were not synergistically inhibited were found. Conversely, several RAS/BRAFV600 wild-type cell lines showed strong synergy. Colorectal cancer lines representing RAS mutation status and presence or absence of synergy were chosen and MAPK signaling upon KRAS knockdown with or without cobimetinib treatment was assessed (FIG. 5B). Interestingly, overall lower levels of MAPK signaling in KRAS mutant lines in which the combination was non-synergistic were observed, as evidenced by lower total protein levels and phosphorylation at multiple nodes in the MAPK pathway. Conversely, in either KRAS mutant or wild-type lines in which the combination showed synergy, significantly higher MAPK signaling was observed. MAPK signaling in lines synergistically inhibited by the combination was abrogated by KRAS knockdown combined with cobimetinib as indicated by lower levels of pMEK, pERK, and pRSK (FIG. 5B). Cell lines synergistically inhibited by the combination showed increased BRAF/CRAF heterodimer formation, as evidenced by CRAF immunoprecipitation and subsequent staining for CRAF and BRAF independent of RAS mutational status (FIG. 5B). Using the in vitro RAF kinase assay, strong increases in pMEK levels after cobimetinib treatment were observed, primarily in the lines showing synergy (FIG. 5B), but not in KRAS wild-type lines that were not synergistically inhibited (FIG. 5C).

Figures 5C, 5D:
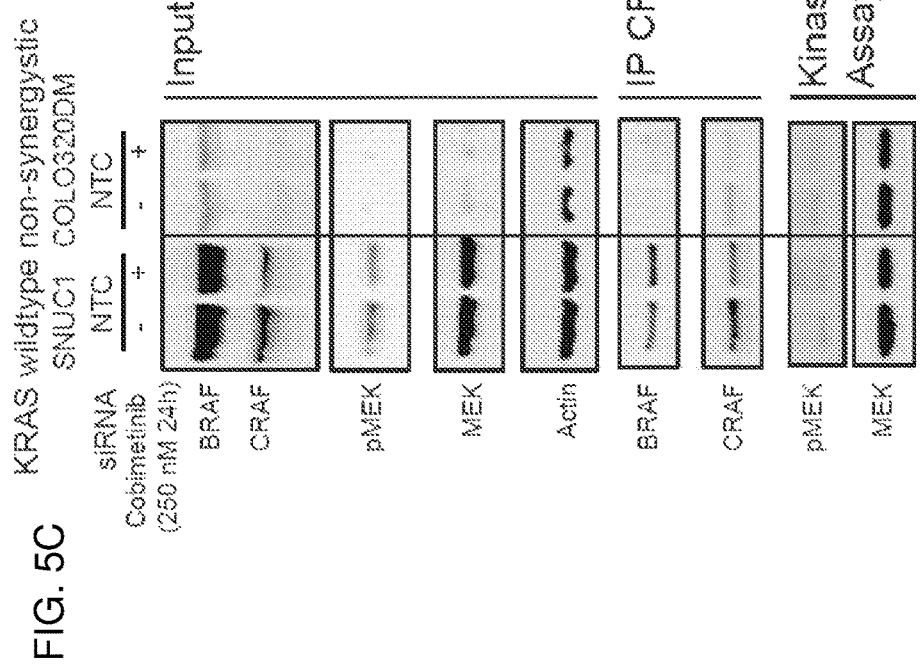
FIG. 5C is an immunoblot showing KRAS wild-type lines that were not synergistically inhibited. Cells were reverse-transfected with 20 nM si-KRAS (L-005069-00-0020) or si-NTC (D-001810-10-20) (Dharmacon On-TARGETplus® pool) in the presence of Lipofectamine RNAiMAX® reagent (Life Technologies), according to the manufacturer's instructions. The medium was changed the day after transfection, and knockdown efficiency was assessed on day 4. 250 nM cobimetinib was added to the cells for 24 hours. Protein lysates were analyzed by Western blotting for phospho- and/or total KRAS, BRAF, CRAF, MEK, ERK, and RSK, relative to control (actin). CRAF and RAF1-RBD were immunoprecipitated from the same lysates and analyzed by Western blotting. The CRAF immunoprecipitates were analyzed for kinase activity utilizing inactive MEK as the substrate.
FIG. 5D is a set of immunoblots showing that combination activity is observed for HM95573 (GDC-5573), a Type II pan-RAF inhibitor, and cobimetinib, a MEK inhibitor, in a A549 KRAS mutant cell line, as assessed by the levels of MAPK pathway markers (pMEK, pERK, and pRSK) following treatment with 1 µM HM95573 (GDC-5573), 250 nM cobimetinib, or both 1 µM HM95573 (GDC-5573) and 250 nM cobimetinib for the indicated time points.
Figure 5E:
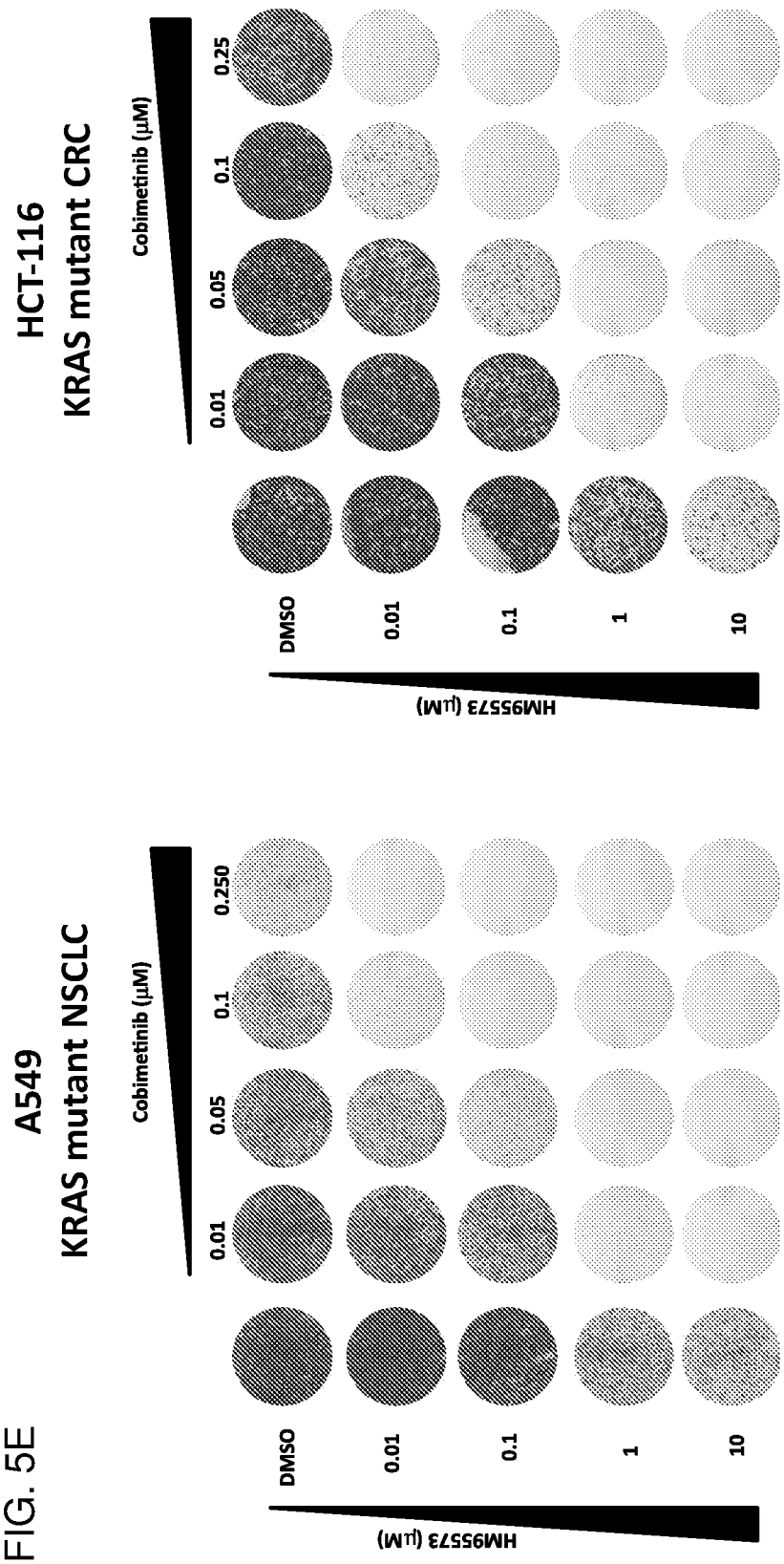
FIG. 5E is a set of images of colony growth assays, showing that type II RAF inhibitors exhibit synergistic activity with cobimetinib and enhance cell death even at sub-efficacious single agent concentrations. A549 cells (left) and HCT-116 cells (right) were treated with the indicated concentrations of RAF inhibitor HM95573 (GDC-5573), cobimetinib, or both HM95573 (GDC-5573) and cobimetinib. Media with appropriate compounds was replenished every 72 hours. Cells were cultured for 8 days and then stained with crystal violet.
Figure 5F:
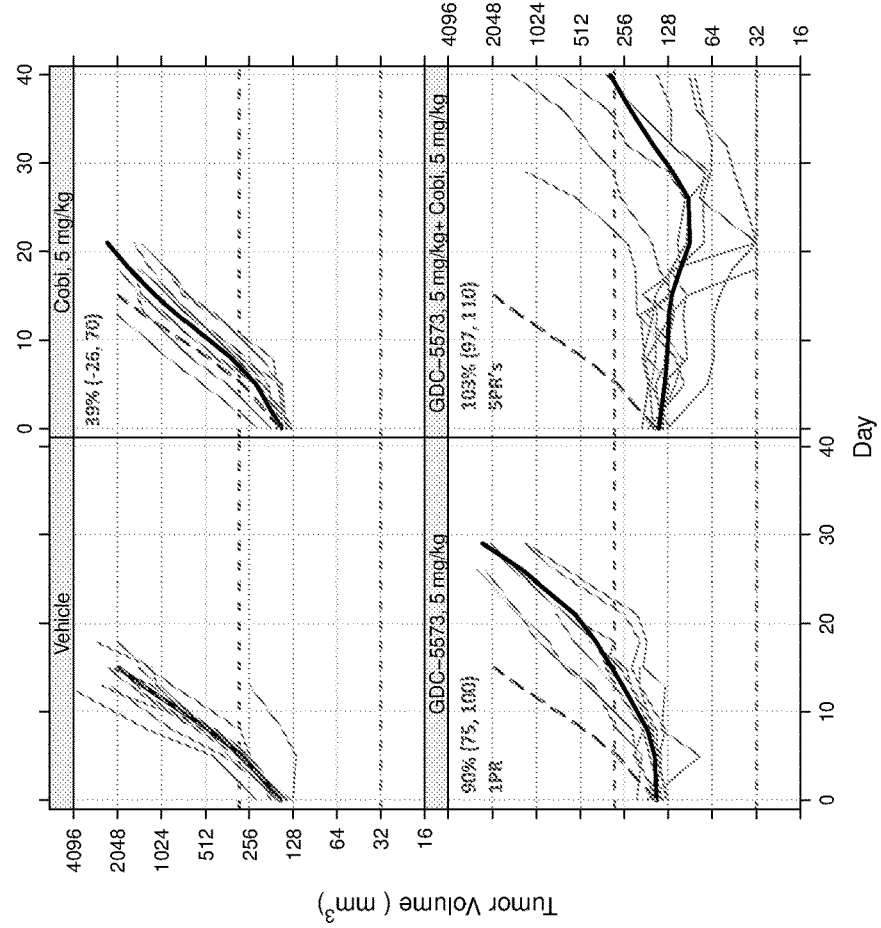
FIG. 5F is a set of graphs showing that treatment of HM95573 (GDC-5573) and cobimetinib resulted in improved tumor growth inhibition (TGI) in a KRAS mutant syngeneic colorectal cancer (CRC) xenograft model, CT26. Animals (n=10/group) were treated for 21 days with vehicle; HM95573 (GDC-5573) at 5 mg/kg (orally, once a day); cobimetinib at 5 mg/kg (orally, once a day); or both agents. Tumor growths of individual animals are shown along with bolded trend lines for each group, represented as tumor volume (mm$^3$) over time (days).
Figure 5G:
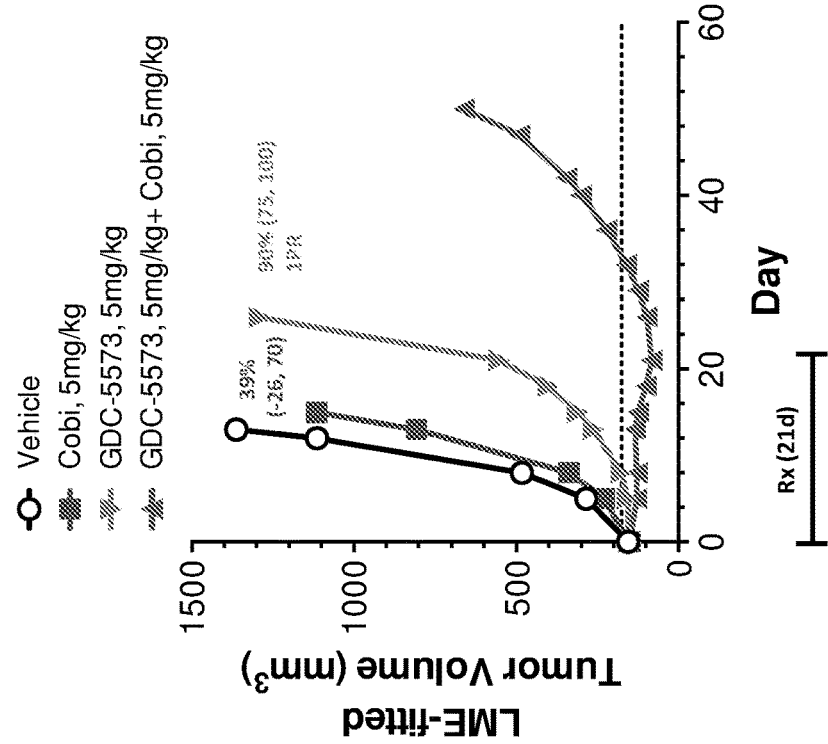
FIG. 5G is a graph showing fitted tumor volume curves for each treatment group described in FIG. 5F.

In a separate set of experiments, combination activity was also observed for HM95573 (GDC-5573), a different Type II pan-RAF inhibitor, with cobimetinib in both KRAS mutant non-small cell lung cancer (NSCLC) cells (A549) and KRAS mutant colorectal cancer (CRC) cells (HCT-116), as assessed by pMEK, pERK, and pRSK levels following treatment with HM95573, cobimetinib, or both agents (FIGS. 5D-5E). The combination of HM95573 (GDC-5573) and cobimetinib also improved tumor growth inhibition (TGI) in vivo in a KRAS mutant syngeneic CRC xenograft model CT26 as compared to treatment with either agent alone (FIGS. 5F-5G).

Figure 5H:
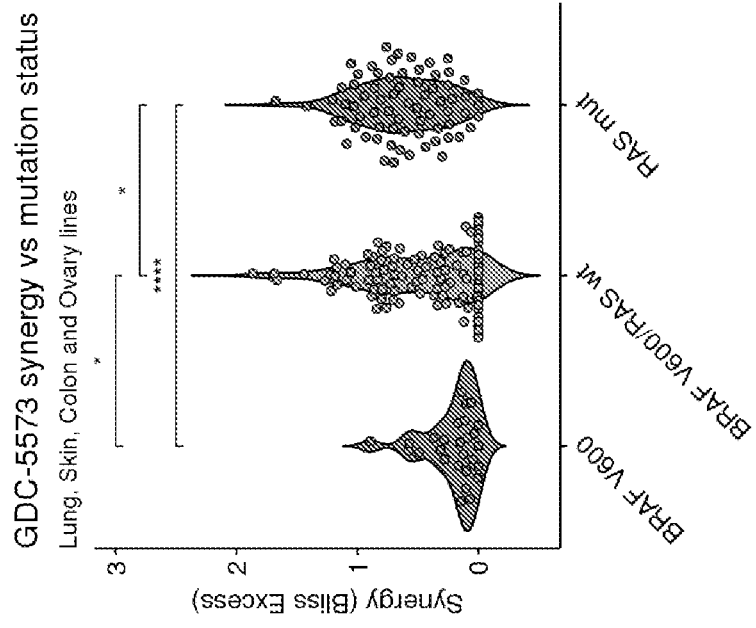
FIG. 5H is a graph showing that the combination of pan-RAF and MEK inhibitors resulted in greater synergy in RAS mutant cell lines and a subset of RAS/RAF wild-type cell lines relative to BRAF-V600 cell lines. Cell viability was assessed using CELLTITER-GLO® in a panel of 196 colon, lung, skin, and ovarian cancer cell lines treated with HM95573 (GDC-5573), cobimetinib, or co-dilution of both HM95573 (GDC-5573) and cobimetinib for three days. Synergy scores are the sum of the positive Bliss excess over the concentration combinations measured. Significance was assessed by two-sided t-test.

To determine whether the combination of HM95573 (GDC-5573) and cobimetinib showed similar synergy across cell lines, 196 lung, colon, skin, and ovarian cancer cell lines were screened with either HM95573 (GDC-5573), cobimetinib, or a co-dilution of both compounds. From these data, the positive Bliss excess over the co-dilution series as a measure of synergy was calculated, and significance was assessed by two-sided t-test. Similar to the combination of AZ-628 and cobimetinib, significantly higher synergy scores were observed in RAS mutant cell lines compared to either BRAF-V600 mutants or wild-type (non-RAS/BRAF-V600 mutants) cell lines (FIG. 5H).

Figure 5I:
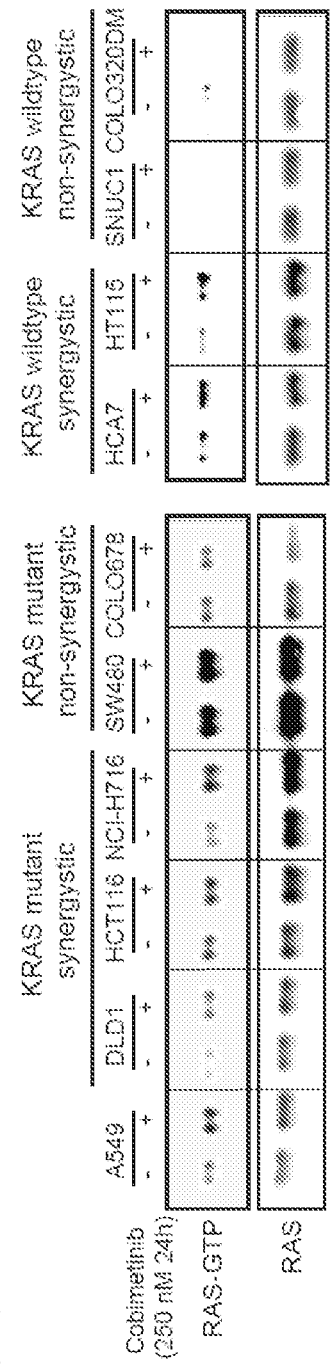
FIG. 5I is a set of immunoblots showing that combination activity of pan-RAF and MEK inhibition correlates with MEK inhibitor-induced RAS-GTP levels in a panel of colorectal cancer cell lines. Active RAS was immunoprecipitated utilizing the RAF1-RBD in the colorectal cell lines indicated, treated either with DMSO vehicle or cobimetinib.

Given the observation of greater synergy across RAS mutant and wild-type cell lines that exhibited increased RAF dimer formation upon cobimetinib treatment, whether these cell lines also exhibited elevated RAS-GTP levels upon treatment with cobimetinib was interrogated. Only cell lines showing synergy showed increased active RAS-GTP in response to cobimetinib treatment, regardless of RAS mutational status (FIG. 5I), consistent with the KRAS-dependent effect observed across cell lines that are synergistically inhibited by the RAF and MEK inhibitor combination.

Figure 6A:
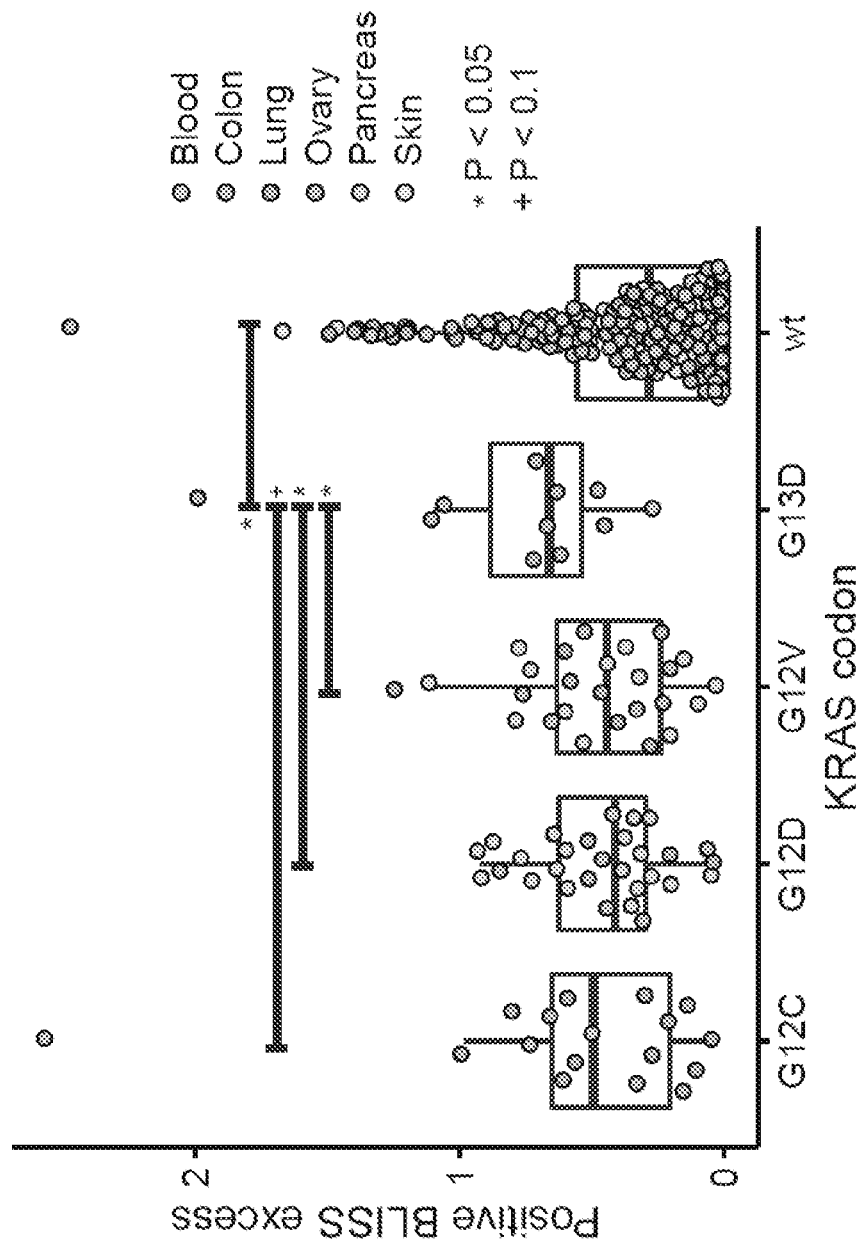
FIG. 6A is a graph showing that KRAS-G13D mutant cell lines are more sensitive to the combination of RAF and MEK inhibition. Positive Bliss excess for the AZ-628/cobimetinib combination for cell lines containing different RAS mutant codons is shown (P-values are two-sided Wilcoxon rank sum tests).
Figure 6B:
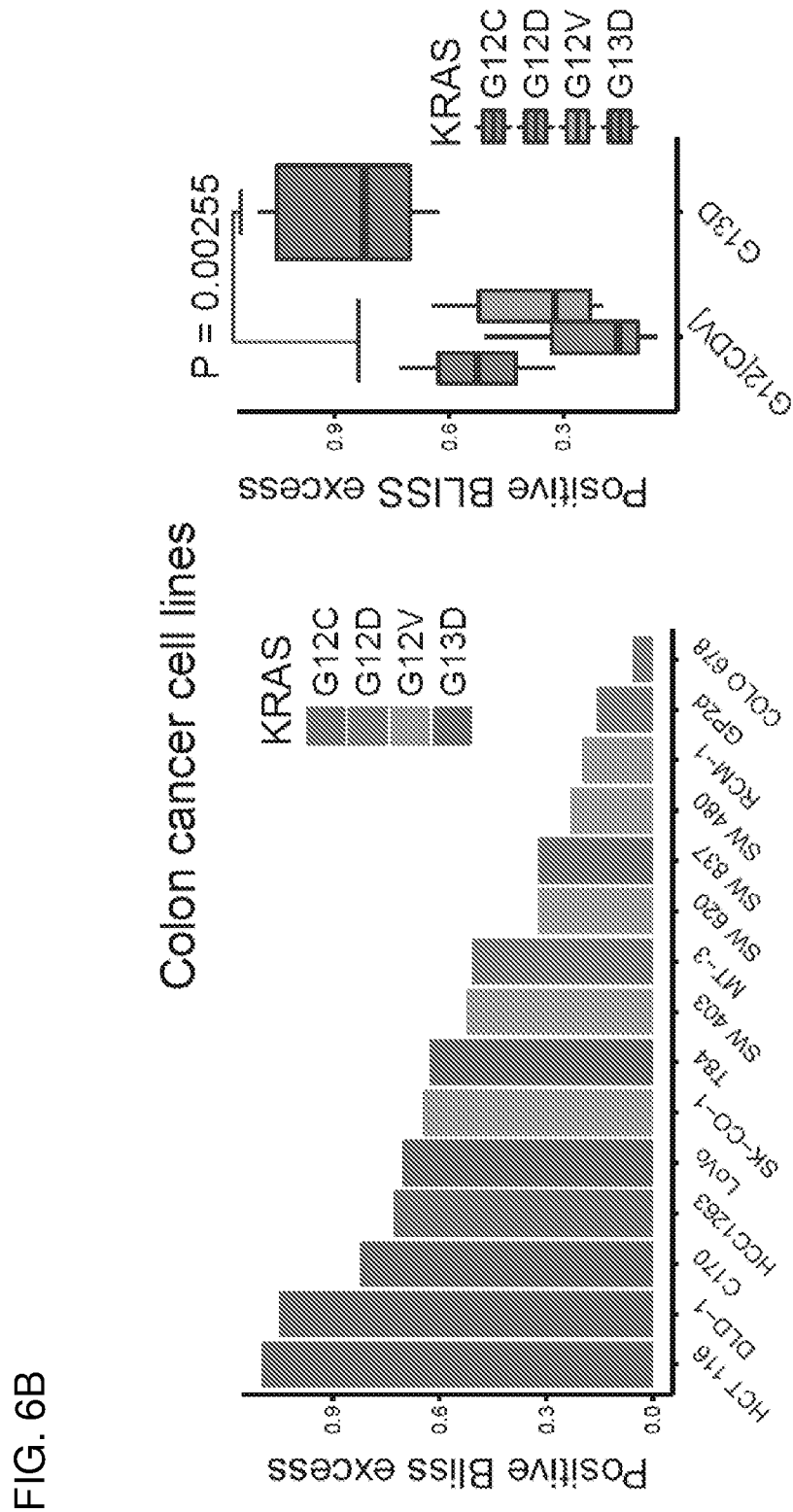
FIG. 6B is a graph showing that KRAS-G13D KRAS$^{G13D}$ mutant cell lines are more sensitive to the combination of RAF and MEK inhibition. Positive Bliss excess for the AZ-628/cobimetinib combination for cell lines containing different RAS mutant codons is shown (P-values are two-sided Wilcoxon rank sum tests).
Figure 6C:
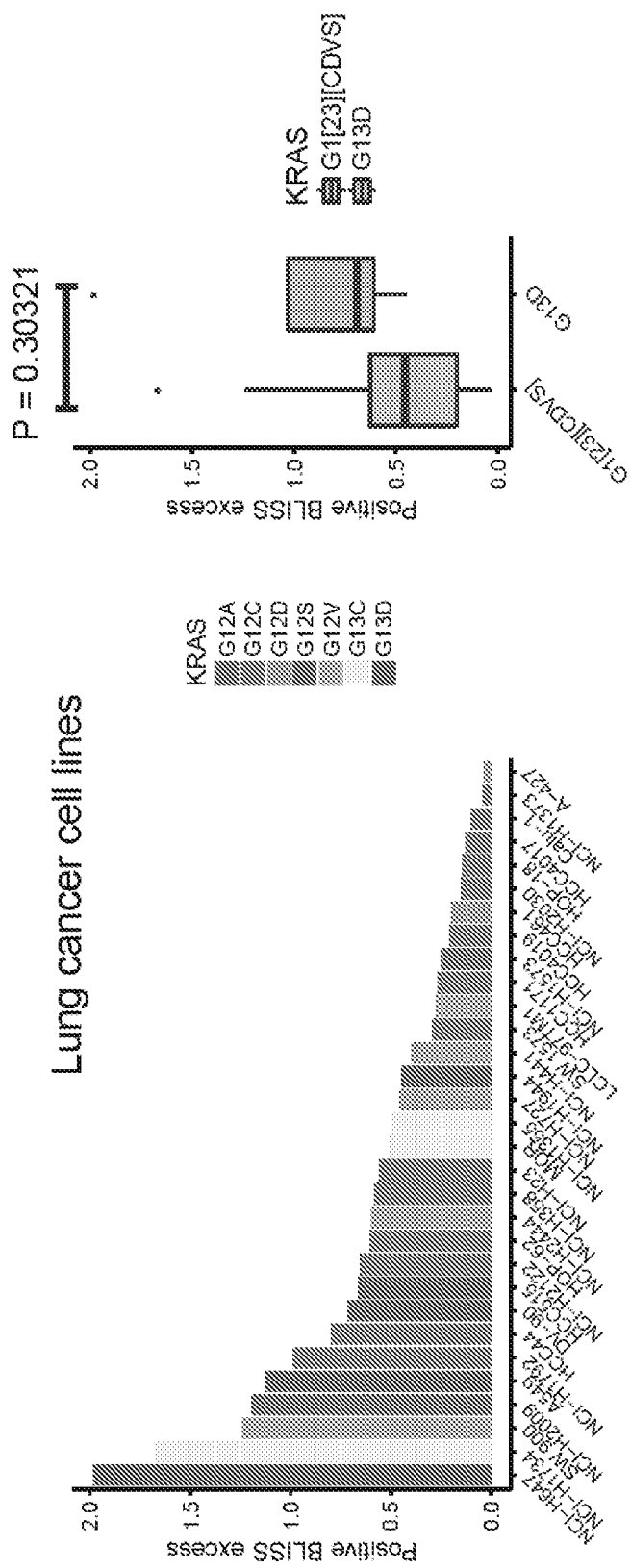
FIG. 6C is a bar graph and box plot showing the excess Bliss scores for lung cell lines (P-values are two-sided Wilcoxon rank sum tests).
Figure 6D:
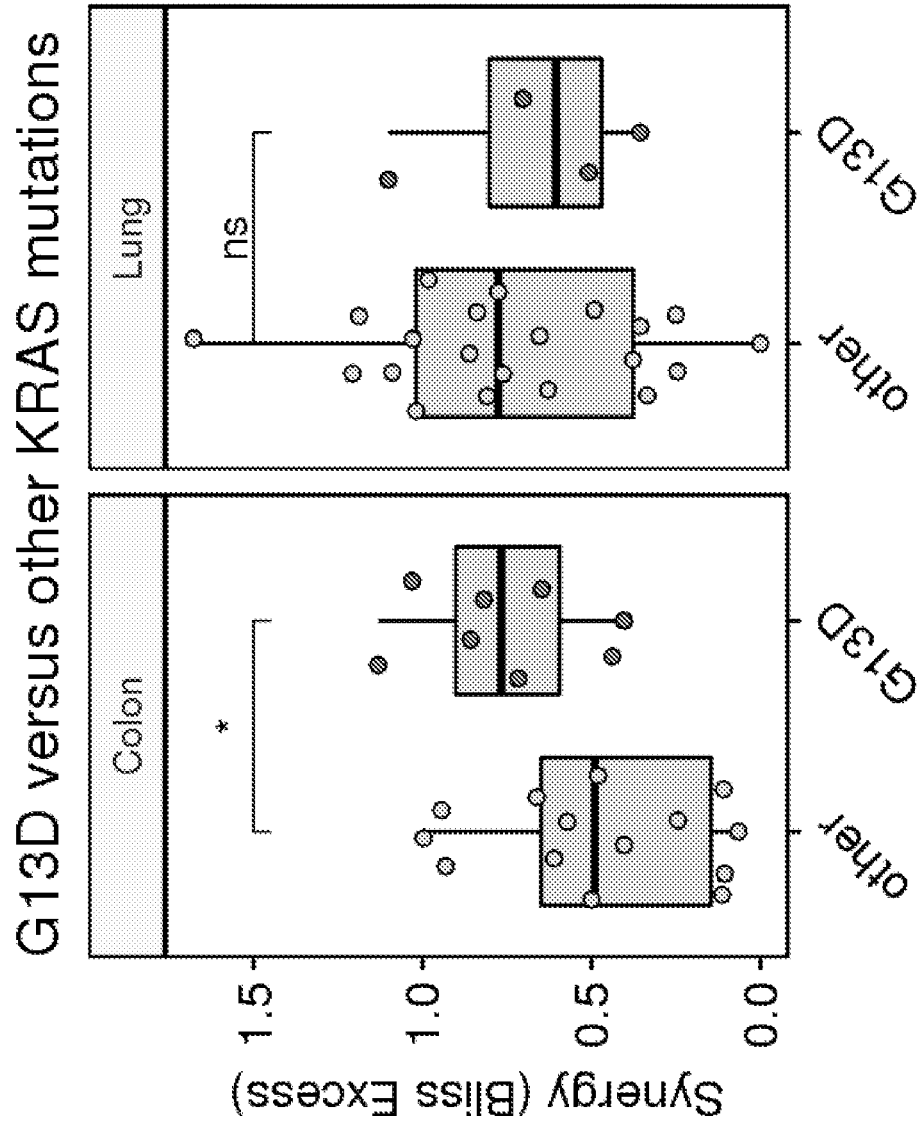
FIG. 6D is a set of box plots showing the excess Bliss scores for KRAS-G13D colorectal (left) and lung (right) cancer cell lines compared to other cell lines carrying non-KRAS-G13D mutations following treatment with HM95573 (GDC-5573) and cobimetinib by co-dilution for three days. Synergy scores are the sum of the positive Bliss excess over the concentration combinations measured. Significance was assessed by two-sided t-test.
Figure 6E:
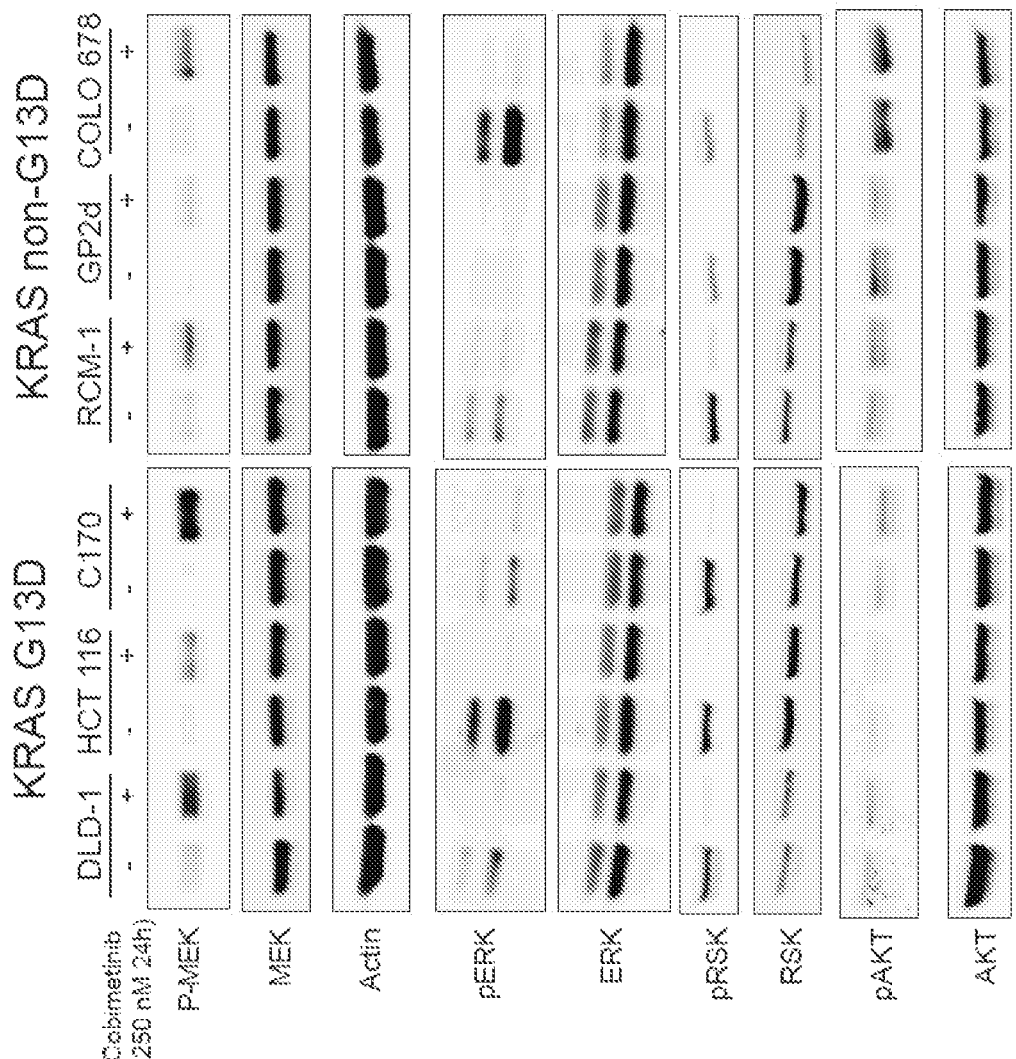
FIG. 6E is a set of immunoblots showing that KRAS-G13D mutant colorectal cell lines show more enhanced induction of pMEK following MEK inhibition relative to other KRAS mutants. The indicated colorectal cell lines were treated with either DMSO or cobimetinib (250 nM) for 24 hr followed by Western blot assessment of phospho- and total levels of MEK, ERK, RSK, and AKT, relative to control (actin).
Figure 6F:
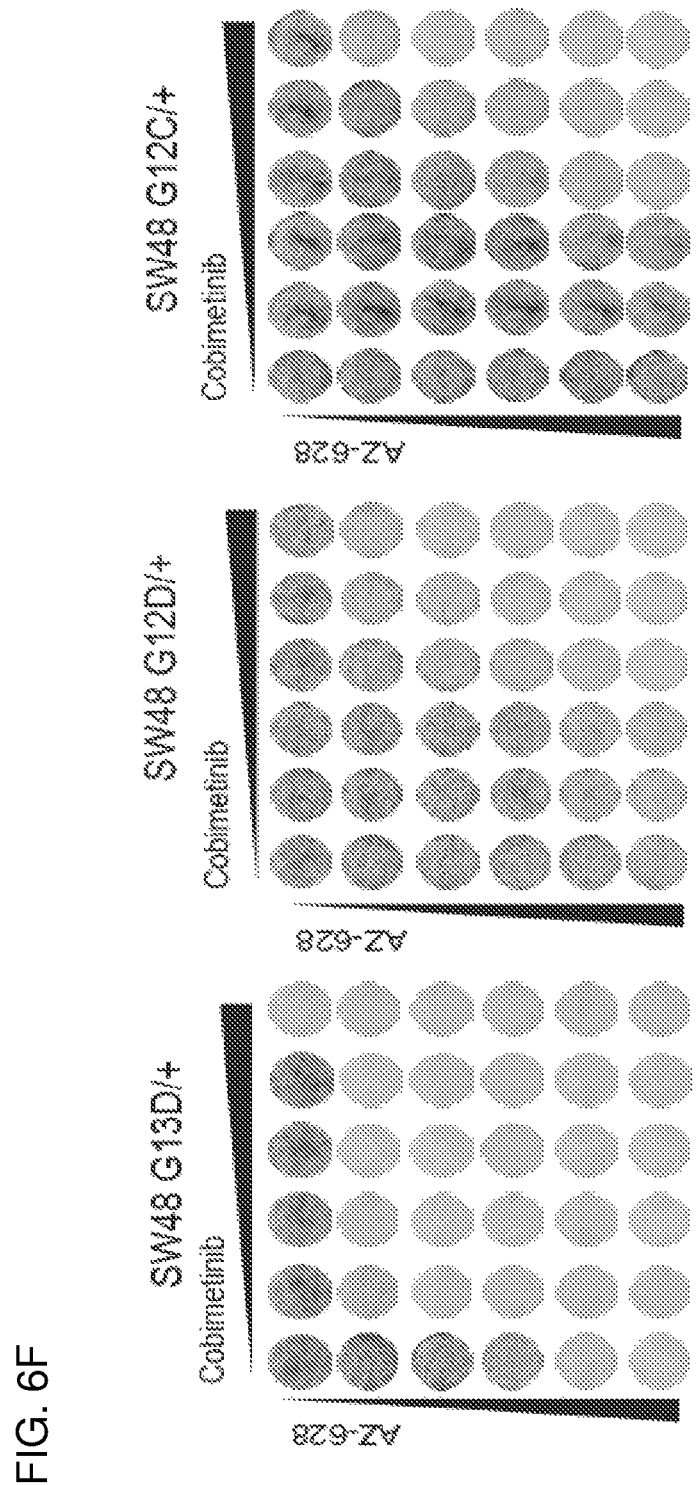
FIG. 6F is a set of images of colony growth assays showing that synergistic activity with type II RAF inhibitors and cobimetinib is greater in KRAS-G13D mutant SW48 cells compared to KRAS-G12D or KRAS-G12C mutant SW48 cells. Isogenic SW48 cells with KRAS-G13D (left), KRAS-G12D (center), or KRAS-G12C (right) knock-in were treated AZ-628, cobimetinib, or both AZ-628 and cobimetinib. Media with appropriate compounds was replenished every 72 hours. Cells were cultured for 8 days and then stained with crystal violet.
Figure 6G:
FIG. 6G is a set of immunoblots showing ERK and pERK levels in isogenic SW48 cells with KRAS-G13D (left), KRAS-G12D (center), or KRAS-G12C (right) knock-in following treatment with AZ-628, cobimetinib, or both agents at the indicated concentrations, relative to control (actin).
Figure 6H:
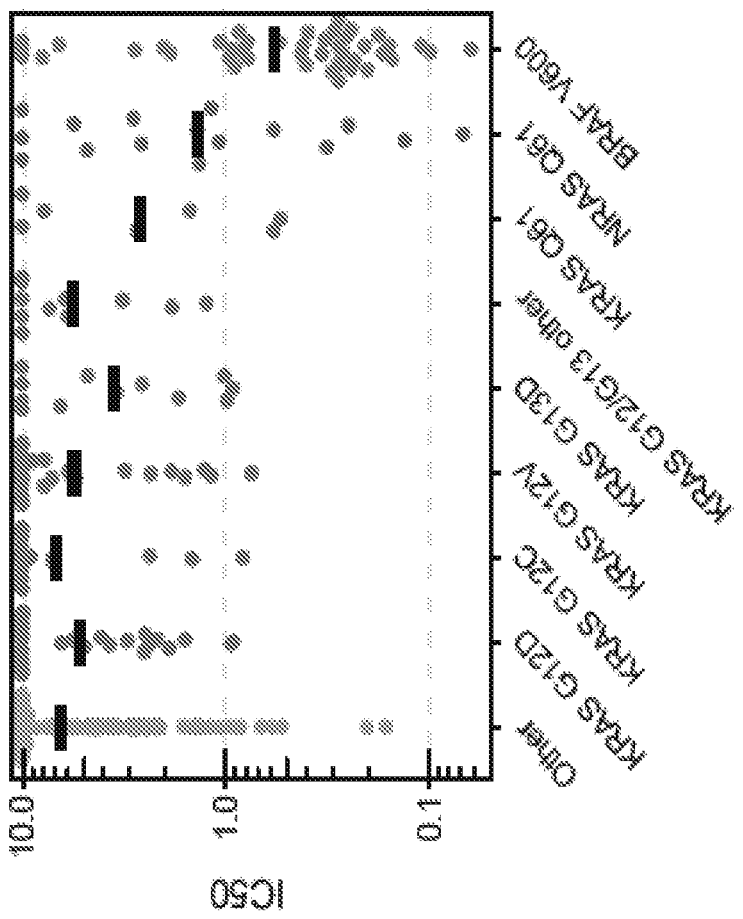
FIG. 6H is a graph showing the relative IC50 values (µM) for AZ-628 across 322 colon, lung, pancreas, ovary, blood, and skin cell lines, as determined by a 3-day CELLTITER-GLO® assay. IC50 curves were fitted using a nonlinear regression, four-parameter fit analysis.

As there is a known biochemical difference in the intrinsic nucleotide exchange between different RAS mutational isoforms depending upon alterations at position 12 or 13 (Hunter et al. *Molecular Cancer Research*. 13:1325-1335 (2015)), the differences in synergy in cell lines with mutations at G12 or G13 with a minimum of five representative cell lines were examined. Interestingly, a significant association between sensitivity to the RAF plus MEK inhibitor combination and presence of the G13D mutation was observed (FIG. 6A). This trend was most evident in colorectal cancer lines where KRAS-G13D mutations are most prevalent and trended in the same manner for lung adenocarcinoma where the prevalence is lower for both tested combinations of AZ-628 and cobimetinib (FIGS. 6B-6C) and HM95573 (GDC-5573) and cobimetinib (FIG. 6D). Analysis of pathway signaling in KRAS-G13D mutant colorectal cell lines versus non-KRAS-G13D revealed a stronger induction of pMEK in G13D cell lines (FIG. 6E). In a separate set of experiments using the SW48 isogenic cell line, KRAS-G13D knock-in cells treated with AZ-628 (starting at 0.1 µM) and cobimetinib (at 250 nM) displayed greater synergy than KRAS-G12D and KRAS-G12C knock-in cells treated with the same combination of AZ-628 and cobimetinib, as assessed by crystal violet staining (FIG. 6F) and Western blot analysis of pERK induction (FIG. 6G). An additional experiment profiling 322 cell lines against AZ-628 showed elevated single agent activity in KRAS-G13D cells as compared to KRAS-G12C, KRAS-G12D, and KRAS-G12V cells (FIG. 6H).

Figure 6I:
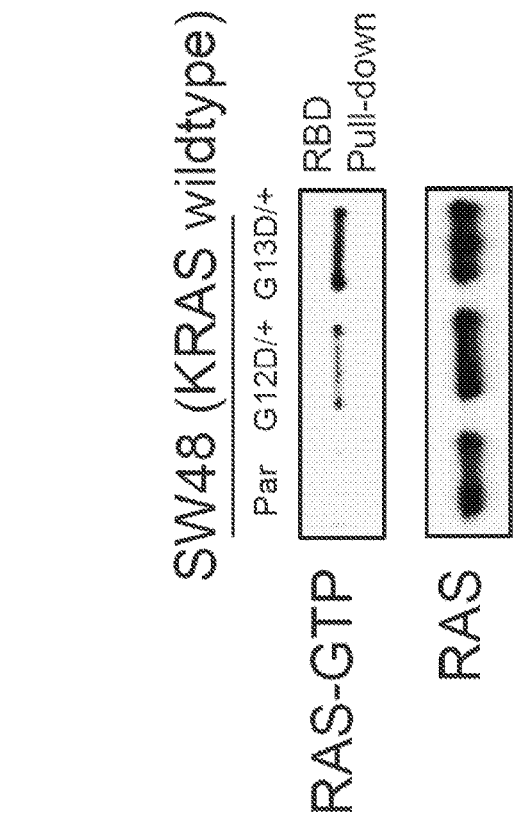
FIG. 6I is an immunoblot showing active RAS that was immunoprecipitated utilizing the RAF1-RBD in the lysate of three isogenic colorectal cell lines: SW48 parental with wild-type KRAS, SW48 with an introduced heterozygous KRAS G12D mutation and SW48 with an introduced heterozygous KRAS G13D mutation.
Figure 6J:
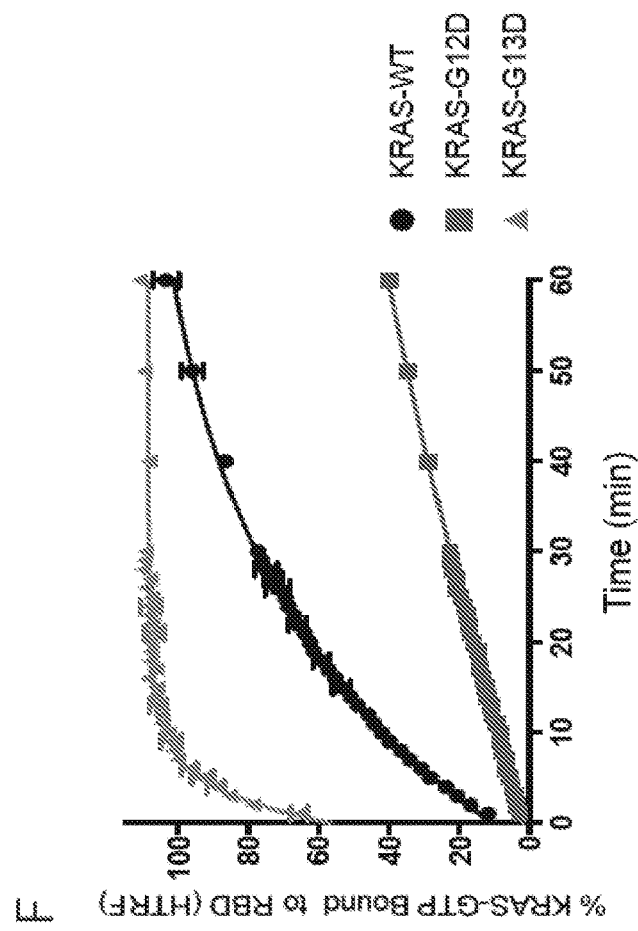
FIG. 6J is a graph showing greater KRAS-GTP levels in SW48 KRAS-G13D compared to SW48 KRAS-G12D and SW48 KRAS wild-type cells as assessed using a nucleotide exchange reaction by time-resolved fluorescence energy transfer (TR-FRET). 6x His-tagged KRAS wild-type, KRAS-G12D, and KRAS-G13D loaded with GDP was incubated with FLAG-tagged RAF1-RBD in the presence of anti-FLAG-Tb antibody and anti-6xHis-d2 antibody. GTP was added to initiate the nucleotide exchange reaction and TR-FRET was measured.

These effects could be directly attributed to the RAS-G13D isoform, as SW48 isogenic cell lines harboring KRAS-WT, KRAS-G12V, or KRAS-G13D demonstrated much higher RAS-GTP levels in the KRAS-G13D clone (FIG. 6I). The elevated nucleotide exchange rate reported for KRAS-G13D (Hunter et al. Molecular Cancer Research. 13:1325-1335 (2015)) could induce a larger dependency on RAF-heterodimer signaling, which is efficiently abrogated by the combination treatment of a MEK and Type II RAF inhibitor. Greater intrinsic nucleotide exchange for KRAS-G13D was confirmed in SW48 KRAS-G13D cells as assessed using a nucleotide exchange reaction by time-resolved fluorescence energy transfer (TR-FRET) (FIG. 6J).

Figure 6K:
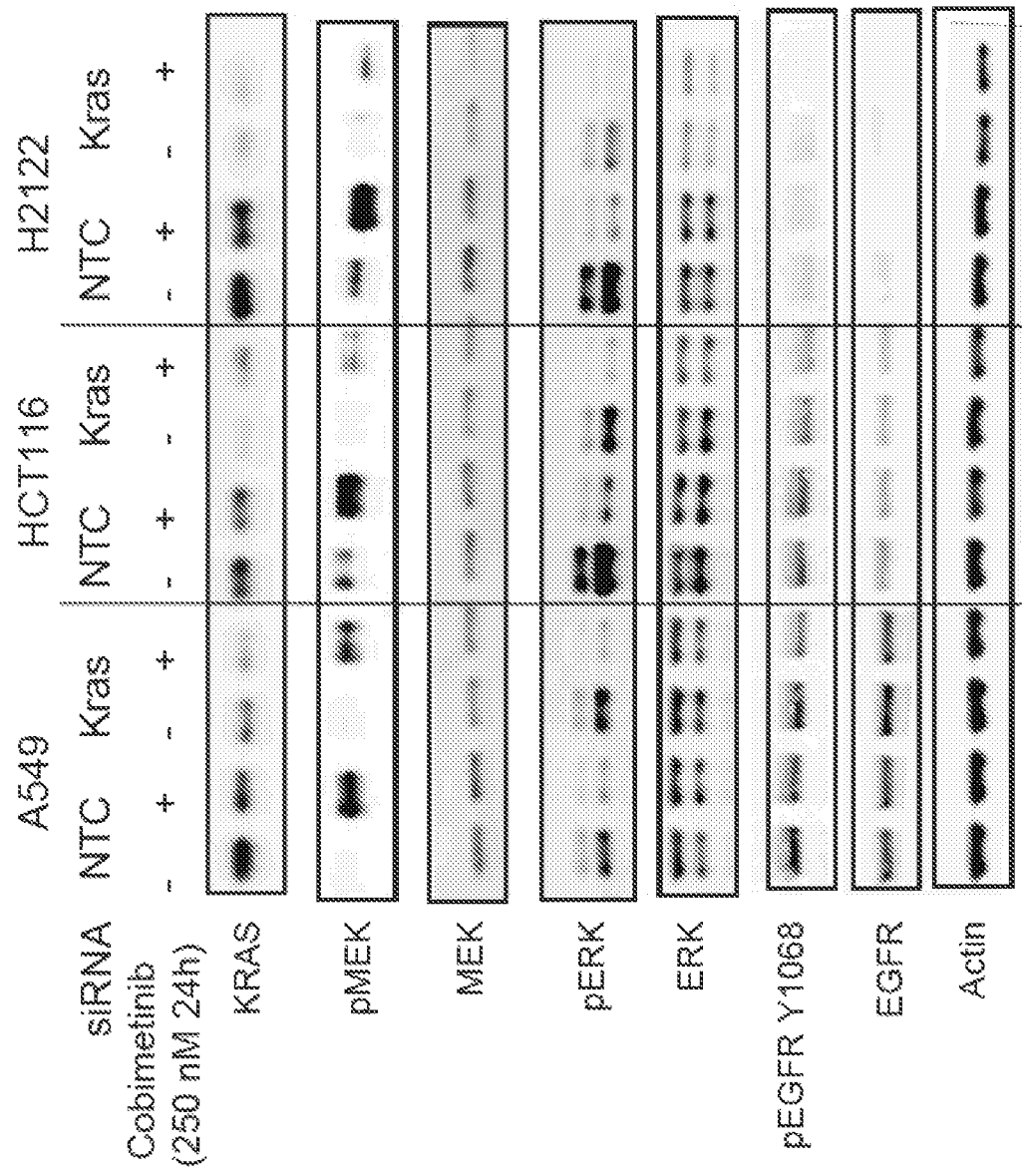
FIG. 6K is an immunoblot showing MAPK pathway protein levels, including total EGFR and P-EGFR at the Y1068 locus, following treatment of the indicated cell lines with either DMSO or cobimetinib at 250 nM for 24 hours.
Figure 6L:
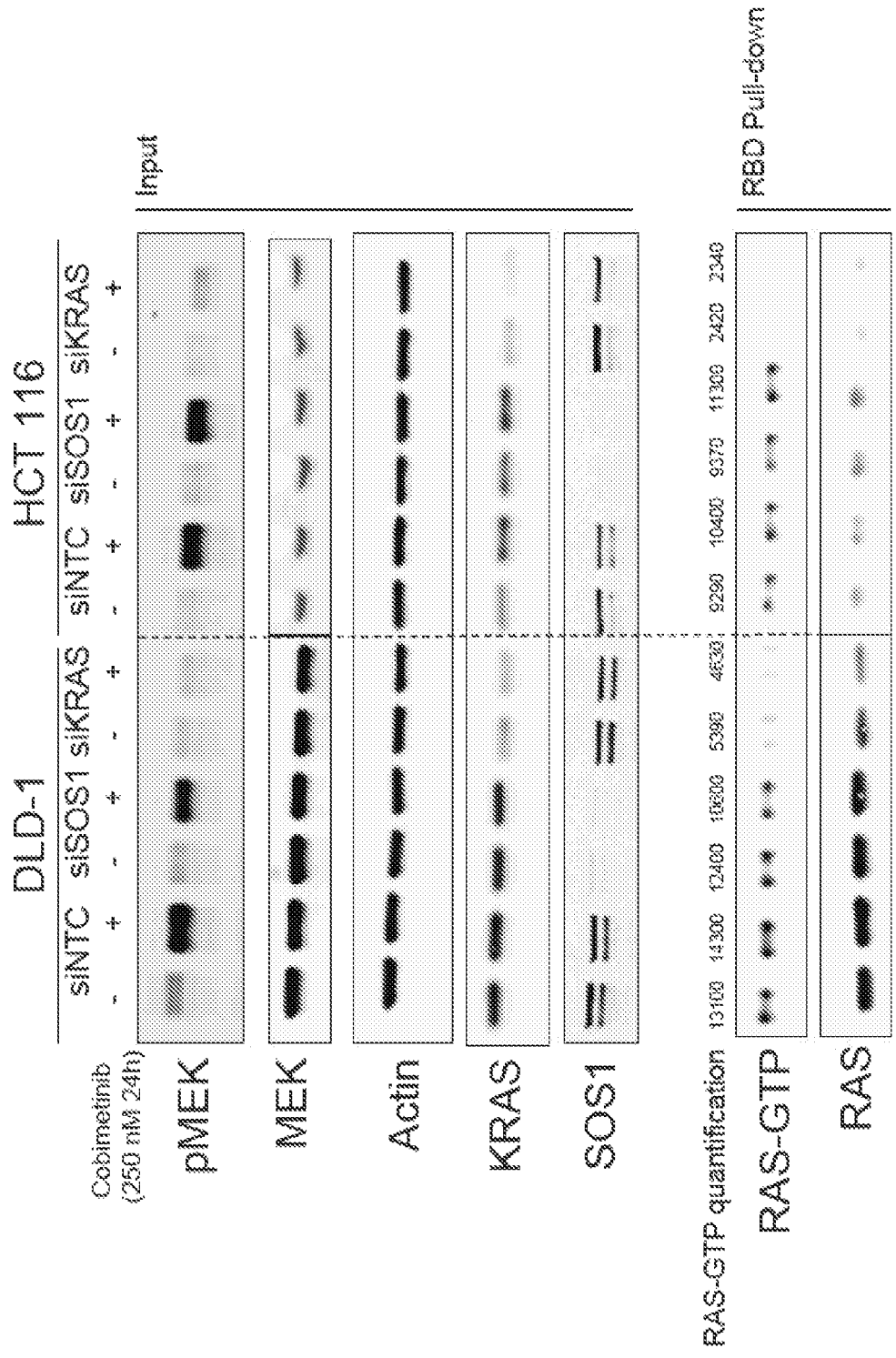
FIG. 6L is an immunoblot showing KRAS, SOS1, MEK, pMEK, and actin levels from the cell lysate following HCT 116 and DLD-1 cells being reverse transfected with si-SOS1 or si-NTC in the presence of lipofectamine RNAiMAX reagent (Life Technologies), according to the manufacturer's instructions, and treated with either DMSO or cobimetinib at 250 nM for 24 hours. RAS-GTP was immunoprecipitated from the lysate by RAF1-RBD from the lysate and analyzed alongside the other proteins.

An alternative explanation for RAS-GTP level increase is the induction as a result of adaptive reprogramming upon treatment with the MEK inhibitor either upstream of RAS via EGFR or downstream via SOS1 activation. To test this directly, pEGFR levels upon cobimetinib treatment were evaluated, but little evidence of EGFR activation was seen under conditions where elevated RAS-GTP levels were observed (FIG. 6K). Similarly, targeted knockdown of SOS1 had no effect on RAS-GTP levels (FIG. 6L), suggesting that neither of these mechanisms is responsible for elevation of RAS-GTP levels.

Example 7

Pan-RAF Inhibitors Also Synergize with Pan-PI3K Inhibition

Figure 7A:
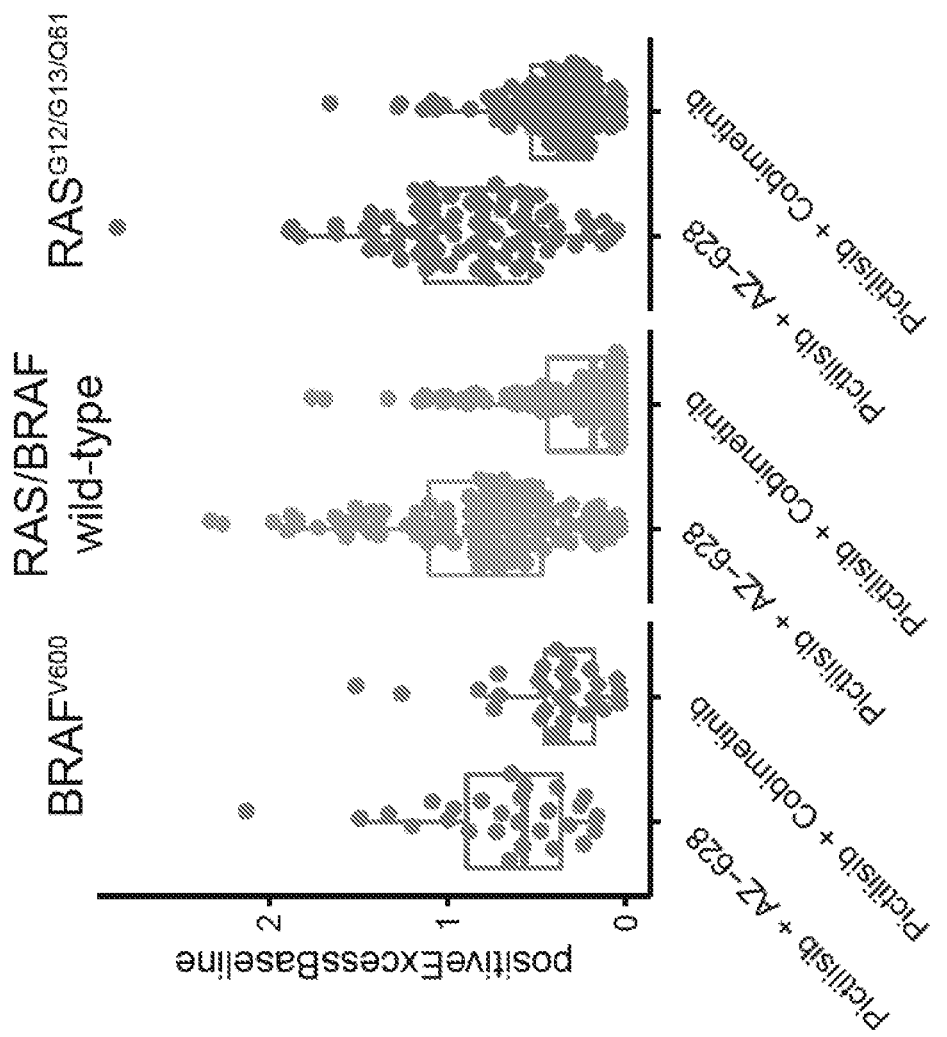
FIG. 7A is a graph showing that the pan-RAF inhibitor (AZ-628) synergizes with pan-PI3K inhibitor, pictilisib (GDC-0941). Cell viability was assessed by CELLTITER-GLO® in a panel of 213 tumor cell lines treated with a co-diluted dose of AZ-628/pictilisib, cobimetinib/pictilisib, or single-agent dose after 3 days. Synergy scores representing the sum of the positive Bliss excess over the concentration combinations measured is plotted.
Figure 7B:
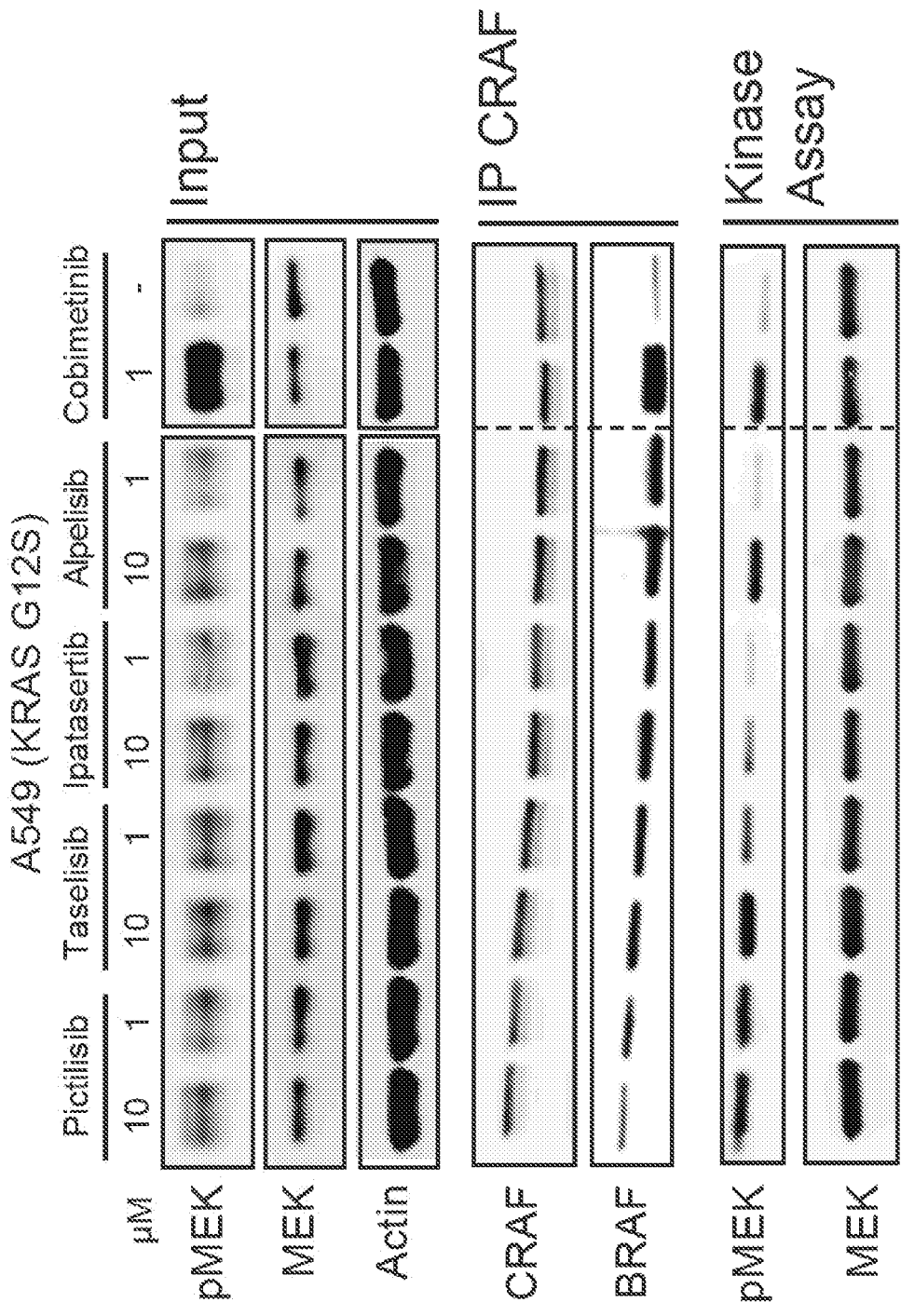
FIG. 7B is an immunoblot showing that the inhibition of KRAS-G12S A549 cells with multiple PI3K inhibitors results in the induction of MAPK pathway activity. A549 were treated with indicated concentrations of PI3K inhibitors or cobimetinib for 24 hours and were then processed for western blot analysis for phospho- and total levels of MEK, relative to control (actin). Lysates were also assessed by immunoprecipitation (IP) for CRAF and immunoblotted for CRAF and BRAF and processed for RAF kinase activity, as before.
Figure 7C:
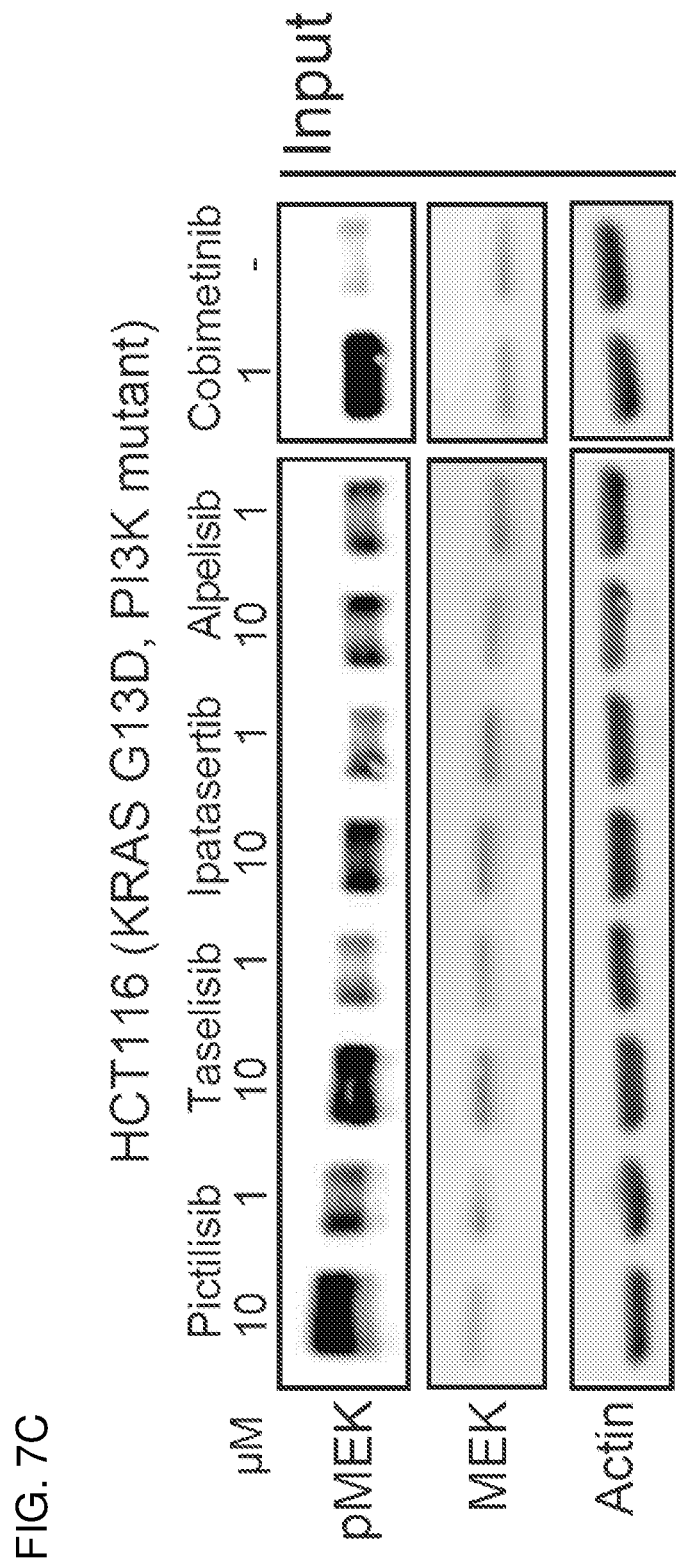
FIG. 7C is an immunoblot for the indicated proteins from lysates derived from HCT116 cells that were treated with the indicated concentrations of PI3K inhibitors or GDC-0973 for 24 hours.

The above data strongly suggest a MEK kinase inhibition-induced feedback, which is particularly potent in KRAS-G13D mutant tumors. In light of these results, the initial compound screen, in which A549 cells with a combination of AZ-628 and a library of 430 different small molecule inhibitors were screened, was reexamined. The presence of pan-PI3K inhibitor, pictilisib, among the top hits of the screen was noted. As A549 cells are PIK3CA wild-type, it was hypothesized that wild-type PI3K inhibition in this context could drive RAS activation through inhibition of negative feedback loops and subsequent activation of RAF. To examine this more broadly, a panel of 213 cell lines was screened with a combination of AZ-628 and pictilisib (FIG. 7A). Interestingly, a large general increased synergy in the AZ-628/pictilisib combination compared to the cobimetinib/pictilisib combination, which was independent of RAS/RAF mutation status, was observed. Next, A549 and HCT116 cells were treated with a panel of PI3K inhibitors and pMEK levels were examined post-treatment. All of the PI3K inhibitors tested were found to increase pMEK in both the A549 (KRAS-G12S) and HCT116 (KRAS-G13D/PIK3CA-H1047R) cells (FIGS. 7B and 7C), with pictilisib and taselisib doing so at lower concentrations. This suggests that the increased flux through the MAPK pathway after inhibition of PI3K is independent of PI3K mutational status. This heightened flux leads to greater downstream signaling as evidenced by increased pERK and pRSK levels and is dose-dependent on the concentration of the PI3K inhibitor pictilisib (FIG. 7D). To investigate whether the effect of inhibiting PI3K leads to increased RAS dependency and increased RAS-GTP levels, a RAF1-RBD pull-down for active RAS-GTP in cells treated with either pictilisib or cobimetinib was performed. Pictilisib was found to increase levels of RAS-GTP (albeit at higher concentrations) similar to that induced by cobimetinib (FIG. 7E).

Figure 7F:
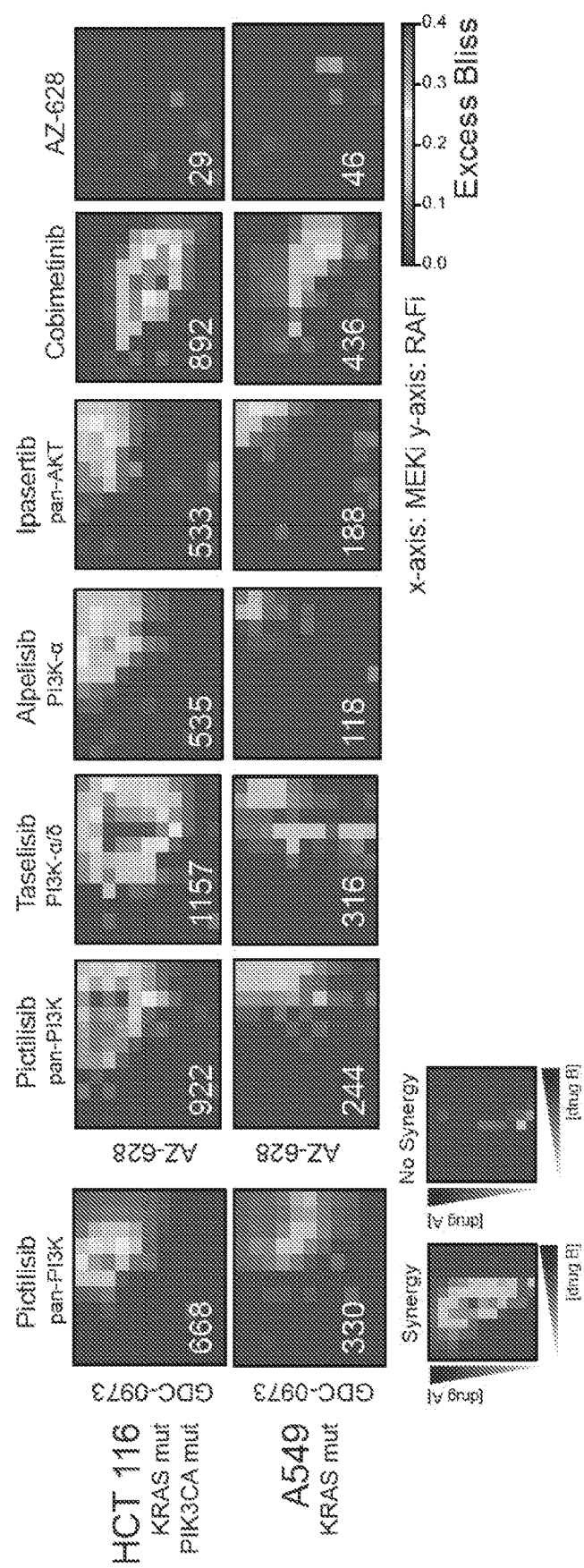
FIG. 7F is a set of images showing calculated Bliss excess scores for 12×12 matrix titrations of cobimetinib or the AZ-628 pan-RAF inhibitor in combination with and PI3K/AKT inhibitors, showing that the Type II pan-RAF inhibitor, AZ-628, synergizes with multiple PI3K/AKT inhibitors in KRAS mutant cell lines. Cell viability was assessed by CELLTITER-GLO® in A549 and HCT116 cells treated with a 12×12 matrix titration of cobimetinib or the AZ-628 pan-RAF inhibitor in combination with and PI3K/AKT inhibitors for 3 days.
Figure 7G:
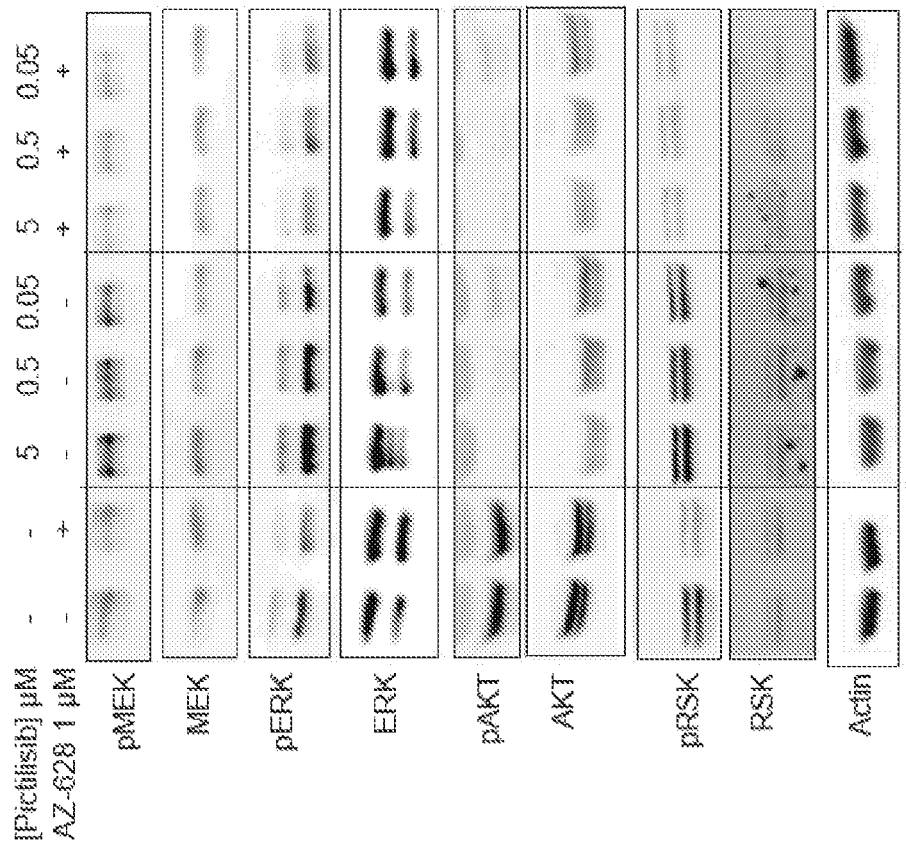
FIG. 7G is an immunoblot showing that the combination of Type II pan-RAF inhibitors with pan-PI3K inhibitors blocks MAPK pathway reactivation mediated by PI3K inhibition. A549 cells were treated with the indicated concentrations of pictilisib and/or AZ-628 for 24 hours and were then processed for Western blot analysis for phospho- and total levels of MEK, ERK, RSK, and AKT, relative to control (actin).

The PI3K synergy with pan-RAF inhibitors was confirmed using full dose matrix Bliss analyses. A panel of PI3K inhibitors was shown to synergize with pan-RAF inhibitor, AZ-628, generating excess Bliss scores similar to the AZ-628/cobimetinib combination (FIG. 7F) with alpelisib (BYL-719), a highly specific PIK3CA inhibitor, and ipatasertib (GDC-0068), an AKT inhibitor, showing 2-3-fold lower synergy. This indicates that broad, wild-type PI3K inhibition can drive RAS activation and may cause subsequent sensitization to RAF inhibition. When the effects on MAPK signaling for either AZ-628 or pictilisib alone or in combination were examined, PI3K inhibition on its own was observed to robustly inhibit pAKT, while the combination of the two agents was observed to prevent the accumulation of pMEK and abrogate downstream signaling to ERK (FIG. 7G).

Example 8

Type II RAF Inhibitors are Efficacious in NRAS Mutant Cell Lines

Figure 8A:
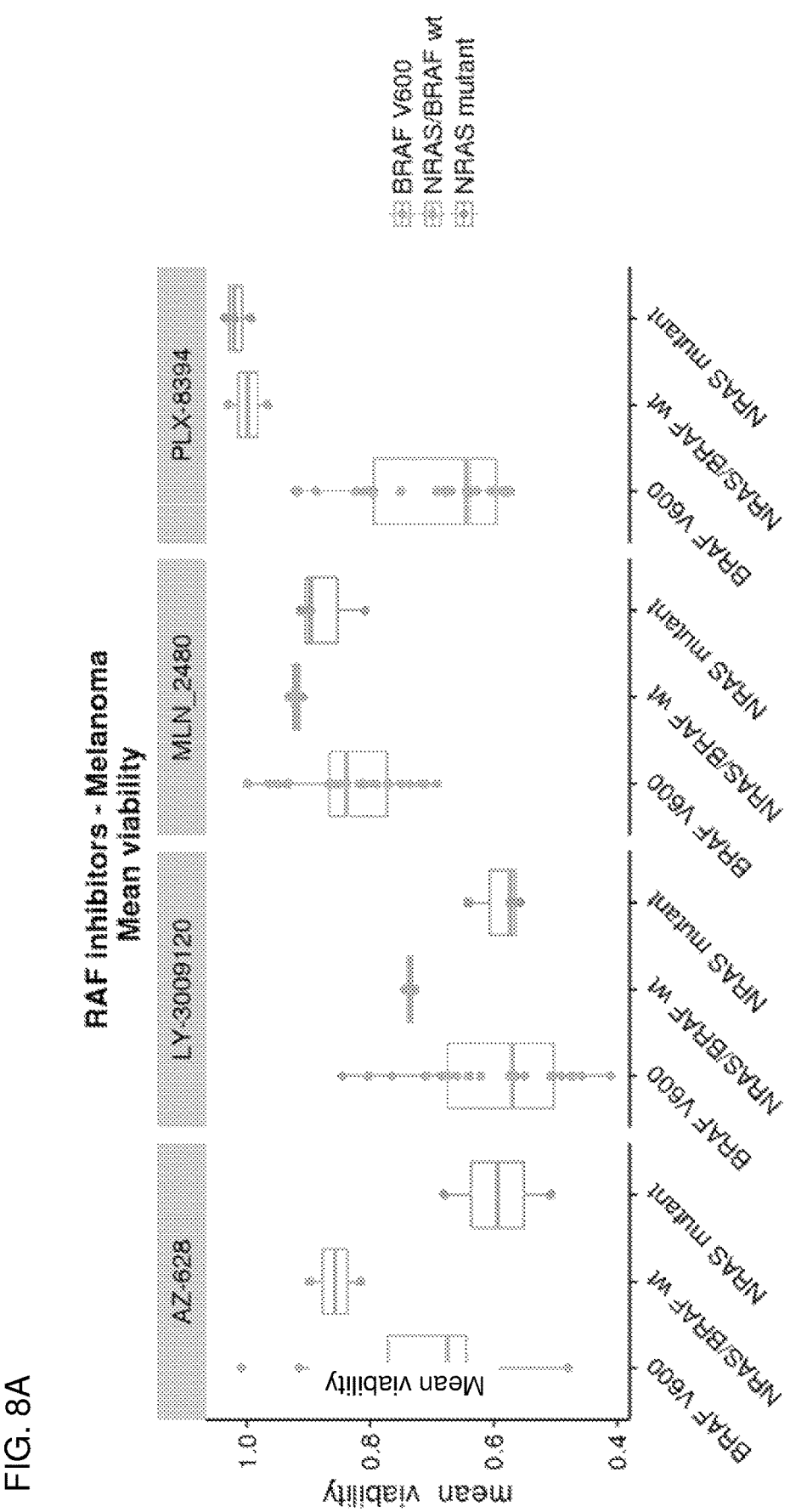
FIGS. 8A and 8B are a series of graphs profiling an NRAS mutant melanoma cell line to sensitivity to three Type II pan-RAF inhibitors (AZ-628, LY-3009120, and MLN-2480) and the Type 1.5 "paradox-breaker" RAF inhibitor, PLX-8394, as compared to BRAF-V600E and NRAS/BRAF wild-type cell lines in viability studies, showing respective mean viability (FIG. 8A) and calculated $IC_{50}$ values (µM) determined using a four-parameter fit using nonlinear regression analysis (FIG. 8B).
Figure 8B:
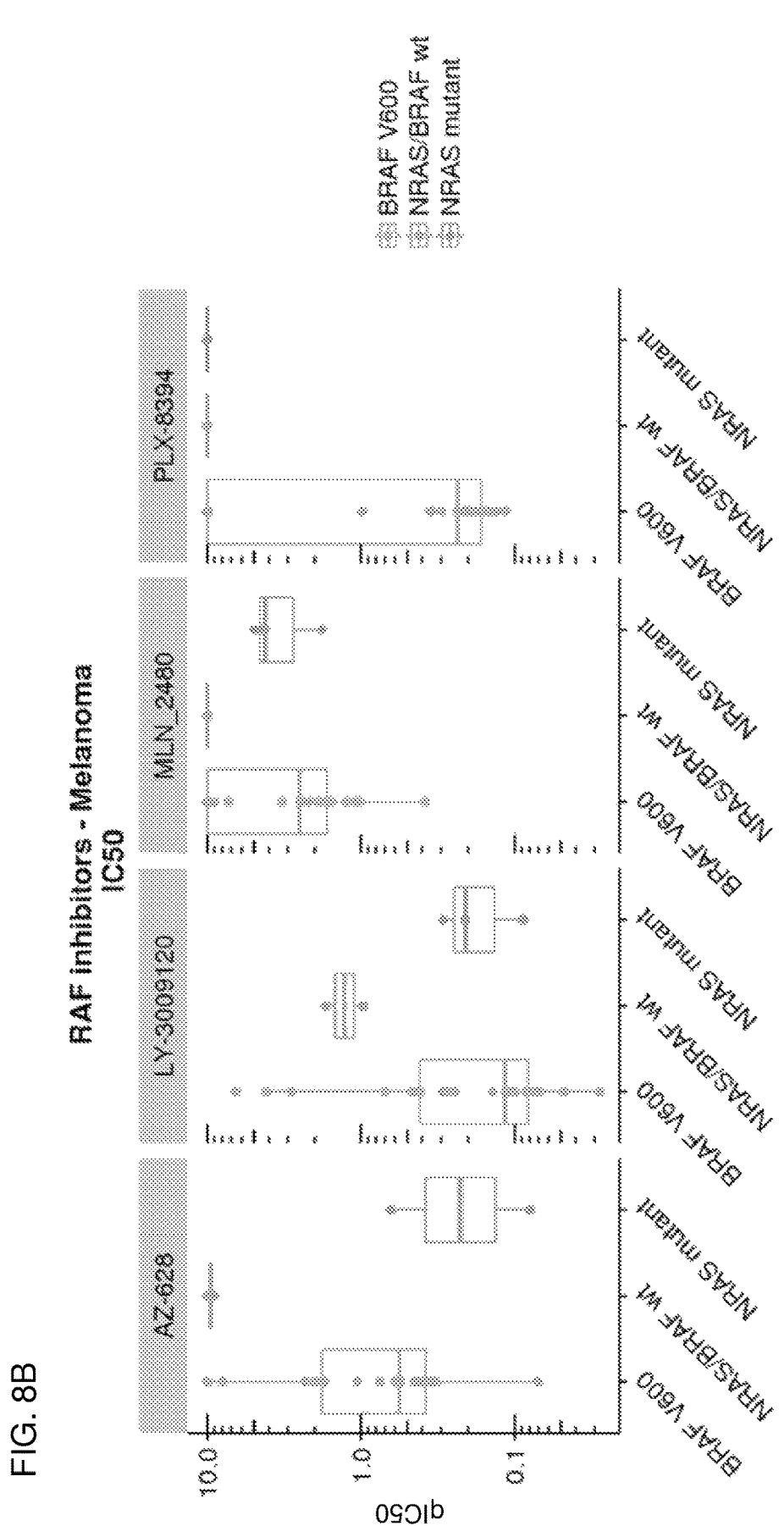
Figure 8C:
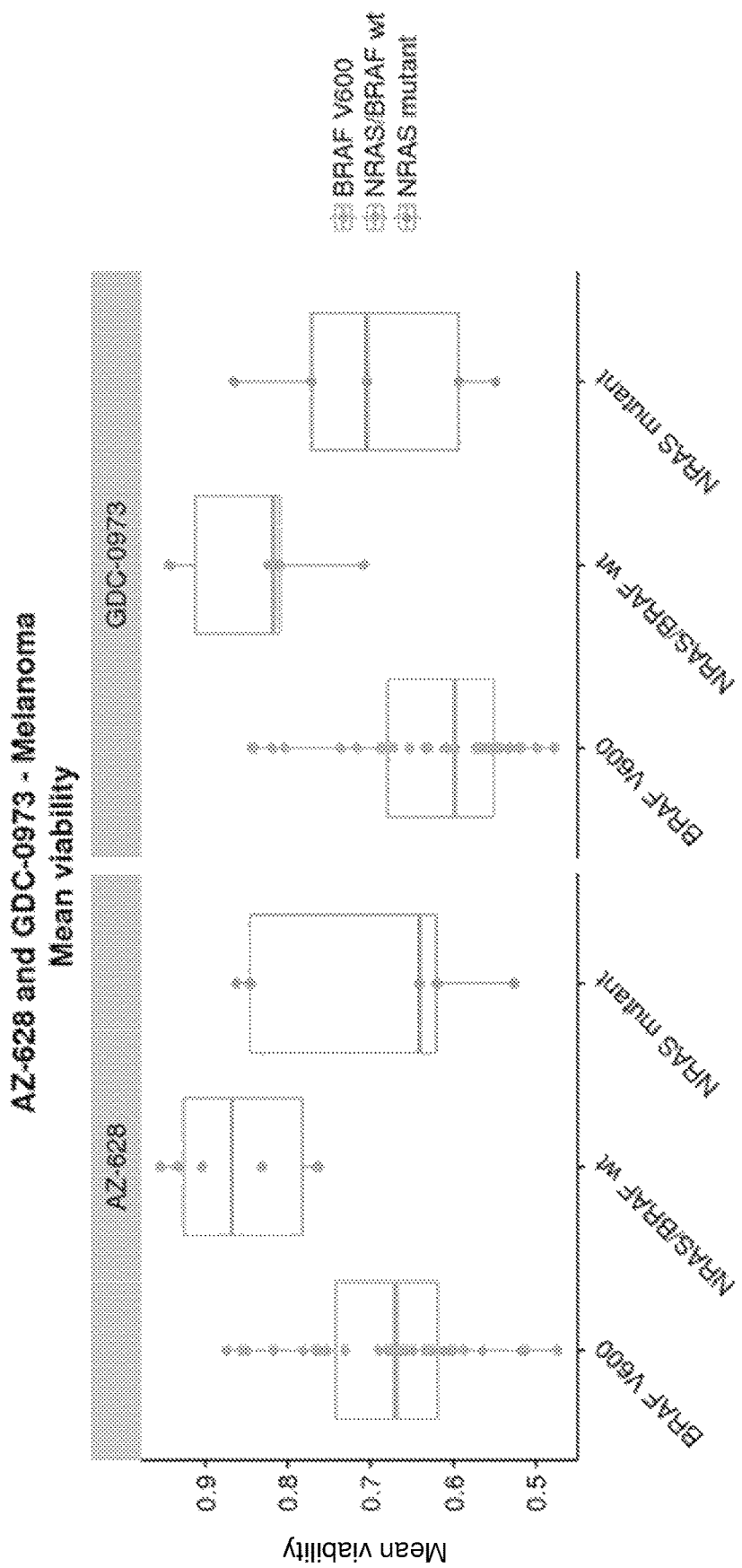
FIGS. 8C and 8D are a series of graphs profiling an NRAS mutant melanoma cell line to sensitivity to Type II pan-RAF inhibitor AZ-628 and MEK inhibitor cobimetinib, as compared to BRAF-V600E and NRAS/BRAF wild-type cell lines in viability studies, showing respective mean viability (FIG. 8C) and calculated $IC_{50}$ values (µM) determined using a four-parameter fit using nonlinear regression analysis (FIG. 8D).
Figure 8D:
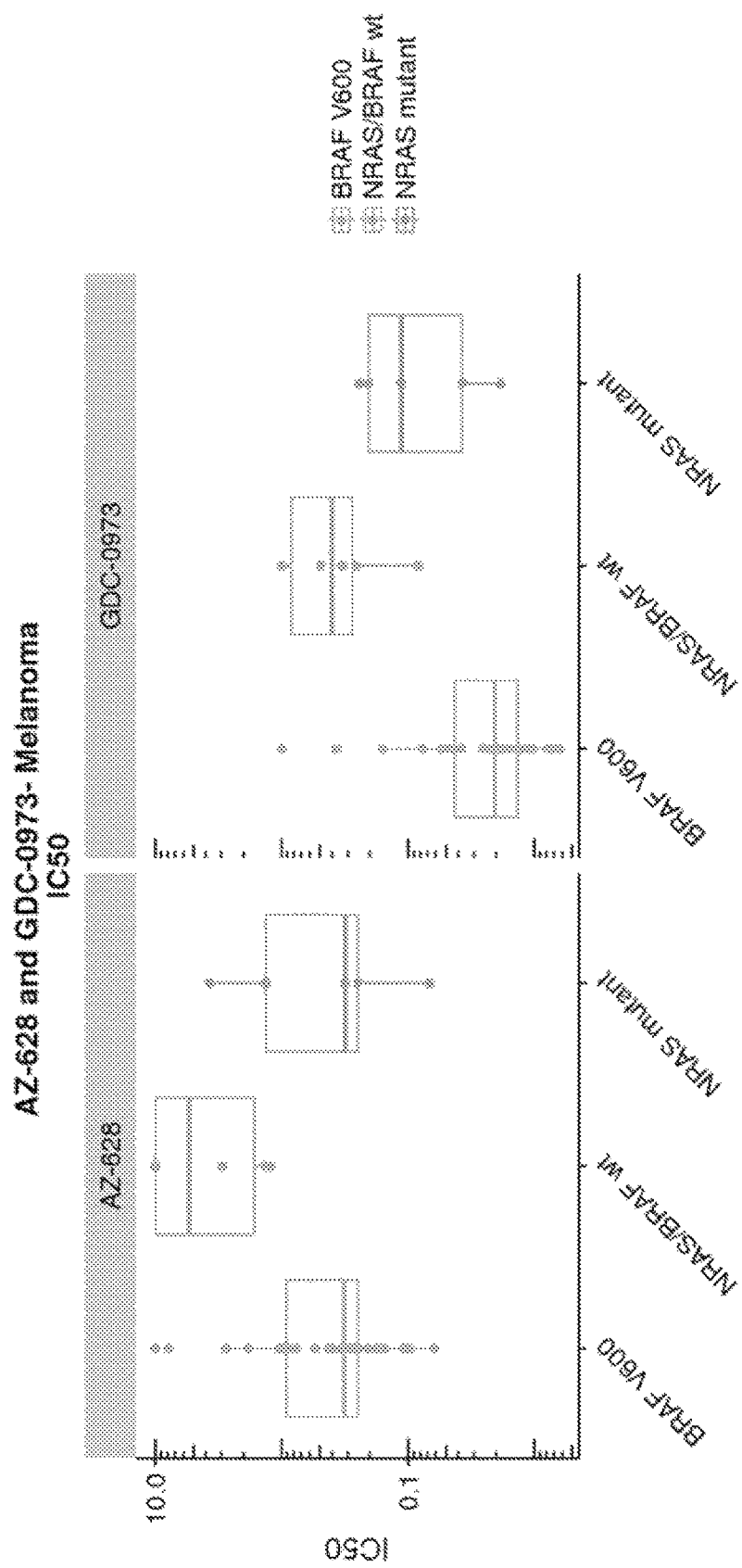

To investigate whether RAF inhibitors—and, in particular, Type II pan-RAF dimer inhibitors—are also efficacious in the context of other RAS gene mutations, cell viability was assessed in a panel of RAF inhibitors in an NRAS mutant melanoma cell line versus BRAF-V600E mutant and NRAS/BRAF wild-type cell lines with the Type II RAF inhibitors, AZ-628, LY-3009120, and MNL-2480, as well as the "paradox breaker" PLX-8394. Type II RAF inhibitors, AZ-628 and LY-3009120, showed approximately equivalent effects on mean viability (FIG. 8A) and inhibitory efficacy as measured by 1050 (FIG. 8B) in the tested NRAS mutant melanoma as compared to the tested BRAF-V600E mutant cell line. These results indicate that Type II pan-RAF dimer inhibitors, such as AZ-628 and LY-3009120, could be very effective alone, or in combination with a MEK inhibitor like cobimetinib, for the treatment of cancers, like melanomas, that have an NRAS activating mutation. The potency of Type II pan-RAF dimer inhibitors, such as AZ-628 and LY-3009120, for treating NRAS mutant cancers was further confirmed by a separate study assessing cell viability and 1050 for NRAS mutant, BRAF-V600E, and NRAS/BRAF wild-type cell lines treated with AZ-628 or cobimetinib (GDC-0973). The results showed that AZ-628 had an equivalent effect in NRAS mutant and BRAF-V600E mutant cell lines, as compared to cobimetinib, which showed greater efficacy in the BRAF-V600E cell line relative to the NRAS mutant cell line (FIGS. 8C and 8D).

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating an individual having melanoma, the method comprising:
   (a) screening a sample from the individual for a KRAS-G13D mutation, wherein the individual has been determined to have a KRAS-G13D mutation; and
   (b) administering a therapeutically effective amount of a pan-RAF dimer inhibitor and a MEK inhibitor to the individual based on the presence of a KRAS-G13D mutation determined in step (a),
   wherein the pan-RAF dimer inhibitor is HM95573 and the MEK inhibitor is cobimetinib (GDC-0973).

2. A method of treating an individual having a melanoma, the method comprising administering to the individual a therapeutically effective amount of a pan-RAF dimer inhibitor and a MEK inhibitor, wherein prior to treatment a sample from the individual has been screened for a KRAS-G13D mutation and the presence of a KRAS-G13D mutation in the sample has been determined, and wherein the pan-RAF dimer inhibitor is HM95573 and the MEK inhibitor is cobimetinib (GDC-0973).

3. The method of claim 1, wherein screening comprises amplifying and sequencing all or a portion of the KRAS gene.

4. The method of claim 1, wherein the sample is a tissue sample, a cell sample, a whole blood sample, a plasma sample, a serum sample, or a combination thereof.

5. The method of claim 2, wherein the sample is a tissue sample, a cell sample, a whole blood sample, a plasma sample, a serum sample, or a combination thereof.

* * * * *